(12) United States Patent
Coruzzi et al.

(10) Patent No.: US 9,464,296 B2
(45) Date of Patent: Oct. 11, 2016

(54) METHODS OF AFFECTING NITROGEN ASSIMILATION IN PLANTS

(75) Inventors: Gloria Coruzzi, New York, NY (US); Rodrigo A. Gutierrez, Santiago (CL); Damion C. Nero, Woodside, NY (US)

(73) Assignee: New York University, New York, NY (US)

( * ) Notice: Subject to any disclaimer, the term of this patent is extended or adjusted under 35 U.S.C. 154(b) by 1267 days.

(21) Appl. No.: 13/044,142

(22) Filed: Mar. 9, 2011

(65) Prior Publication Data

US 2011/0179519 A1    Jul. 21, 2011

Related U.S. Application Data

(62) Division of application No. 12/079,001, filed on Mar. 24, 2008, now Pat. No. 8,153,863.

(60) Provisional application No. 60/919,818, filed on Mar. 23, 2007.

(51) Int. Cl.
| | | |
|---|---|---|
| *A01H 5/00* | (2006.01) | |
| *C12N 15/82* | (2006.01) | |
| *C07K 14/415* | (2006.01) | |

(52) U.S. Cl.
CPC ......... *C12N 15/8243* (2013.01); *C07K 14/415* (2013.01); *C12N 15/8261* (2013.01); *C12N 15/8222* (2013.01)

(58) Field of Classification Search
None
See application file for complete search history.

(56) References Cited

U.S. PATENT DOCUMENTS

| | | |
|---|---|---|
| 3,674,821 A | 7/1972 | Gooding |
| 4,407,956 A | 10/1983 | Howell |
| 4,684,611 A | 8/1987 | Schilperoort et al. |
| 4,945,050 A | 7/1990 | Sanford et al. |
| 5,023,179 A | 6/1991 | Lam et al. |
| 5,100,792 A | 3/1992 | Sanford et al. |
| 5,110,732 A | 5/1992 | Benfey et al. |
| 5,240,855 A | 8/1993 | Tomes |
| 5,256,558 A | 10/1993 | Coruzzi et al. |
| 5,322,783 A | 6/1994 | Tomes et al. |
| 5,324,646 A | 6/1994 | Buising et al. |
| 5,380,831 A | 1/1995 | Adang et al. |
| 5,391,725 A | 2/1995 | Coruzzi et al. |
| 5,401,836 A | 3/1995 | Baszczynski et al. |
| 5,428,148 A | 6/1995 | Reddy et al. |
| 5,436,391 A | 7/1995 | Fujimoto et al. |
| 5,459,252 A | 10/1995 | Conkling et al. |
| 5,565,350 A | 10/1996 | Kmiec |
| 5,595,896 A | 1/1997 | Coruzzi et al. |
| 5,612,472 A | 3/1997 | Wilson et al. |
| 5,633,363 A | 5/1997 | Colbert et al. |
| 5,689,044 A | 11/1997 | Ryals et al. |
| 5,744,334 A | 4/1998 | Dobres et al. |
| 5,750,386 A | 5/1998 | Conkling et al. |
| 5,789,156 A | 8/1998 | Bujard et al. |
| 5,814,618 A | 9/1998 | Bujard et al. |
| 5,824,857 A | 10/1998 | Beachy et al. |
| 5,824,867 A | 10/1998 | Coruzzi et al. |
| 5,837,876 A | 11/1998 | Conkling et al. |
| 5,898,096 A | 4/1999 | Klee et al. |
| 5,907,086 A | 5/1999 | Neill et al. |
| 5,955,651 A | 9/1999 | Coruzzi et al. |
| 5,959,174 A | 9/1999 | Coruzzi et al. |
| 5,959,176 A | 9/1999 | Torikai et al. |
| 5,981,703 A | 11/1999 | Coruzzi et al. |
| 6,028,250 A | 2/2000 | Ohba et al. |
| 6,031,156 A | 2/2000 | Coruzzi et al. |
| 6,107,547 A | 8/2000 | Coruzzi et al. |
| 6,137,031 A * | 10/2000 | Zhang ................ C12N 15/8279 435/468 |
| 6,177,275 B1 | 1/2001 | Coruzzi et al. |
| 6,388,172 B1 | 5/2002 | Tobin et al. |
| 6,451,546 B1 | 9/2002 | Coruzzi et al. |
| 6,664,446 B2 | 12/2003 | Heard et al. |
| 6,822,079 B2 | 11/2004 | Coruzzi et al. |
| 6,864,405 B1 | 3/2005 | Coruzzi et al. |
| 8,153,863 B2 | 4/2012 | Coruzzi et al. |
| 2003/0061637 A1 | 3/2003 | Jiang et al. |
| 2006/0150283 A1 | 7/2006 | Alexandrov et al. |
| 2009/0094711 A1 | 4/2009 | Coruzzi et al. |

(Continued)

FOREIGN PATENT DOCUMENTS

| | | |
|---|---|---|
| DE | 4005152 | 8/1991 |
| EP | 116718 | 8/1984 |
| EP | 175966 | 4/1986 |

(Continued)

OTHER PUBLICATIONS

Fitter et al (The Plant Journal (2002) 31(6): 713-727).*
Tamai et al (Plant Cell Physiol.(2002) 43(1): 99-107).*
Friedberg (Brief Bioinformatics (2006) 7: 225-242).*
Lacombe et al (Science (2001) vol. 292, pp. 1486-1487).*
Fitter et al (The Plant Journal (2002) 31 (6): 713-727).*
Jakoby et al (Trends in Plant Science vol. 7 No. 3 Mar. 2002).*
Tamai et al (Plant Cell Physiol.(2002) 43(1 ): 99-107).*
Accession No. Poptrl#552368, dated Apr. 27, 1993.
Accession No. Poptrl#731468, dated Jun. 28, 2011.
Accession No. Poptrl#654401 dated Jan. 28, 2011.
Accession No. At2g20570.
Accession No. At2g46830.
Accession No. At5g49450.
Accession No. 0s06g24070.

(Continued)

*Primary Examiner* — Lee A Visone
(74) *Attorney, Agent, or Firm* — Jones Day

(57) ABSTRACT

Provided herein are compositions and methods for producing transgenic plants. In specific embodiments, transgenic plants comprise a construct comprising a polynucleotide encoding CCA1, GLK1 or bZIP1, operably linked to a plant-specific promote, wherein the CCA1, GLK1 or bZIP1 is ectopically overexpressed in the transgenic plants, and wherein the promoter is optionally a constitutive or inducible promoter. In other embodiments, transgenic plants in which express a lower level of CCA1, GLK1 or bZIP1 are provided. Also provided herein are commercial products (e.g., pulp, paper, paper products, or lumber) derived from the transgenic plants (e.g., transgenic trees) produced using the methods provided herein.

20 Claims, 14 Drawing Sheets

(56) References Cited

U.S. PATENT DOCUMENTS

Figure 1:
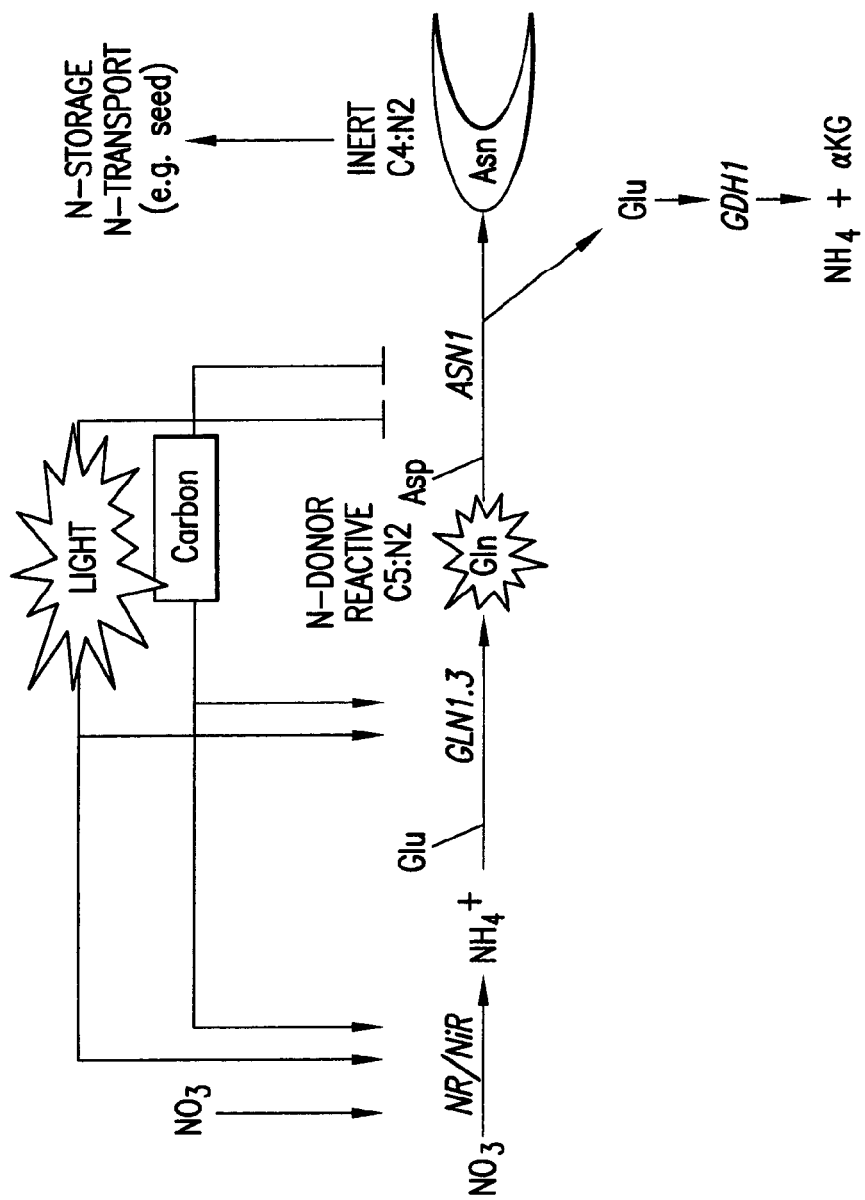

| | | | |
|---|---|---|---|
| 2012/0151635 | A1 | 6/2012 | Coruzzi et al. |
| 2015/0067923 | A1* | 3/2015 | Coruzzi ............ C12N 15/8212 800/298 |

FOREIGN PATENT DOCUMENTS

| | | |
|---|---|---|
| EP | 270355 | 6/1988 |
| EP | 290395 | 11/1988 |
| EP | 331083 | 9/1989 |
| EP | 434616 | 6/1991 |
| EP | 444882 | 9/1991 |
| EP | 486233 | 5/1992 |
| EP | 486234 | 5/1992 |
| WO | WO 87/06614 | 11/1987 |
| WO | WO 90/12096 | 10/1990 |
| WO | WO 92/09696 | 6/1992 |
| WO | WO 92/14828 | 9/1992 |
| WO | WO 93/22443 | 11/1993 |
| WO | WO 94/00583 | 1/1994 |
| WO | WO 99/46976 | 9/1999 |
| WO | WO 99/50428 | 10/1999 |
| WO | WO 00/01832 | 1/2000 |
| WO | WO 00/03012 | 1/2000 |
| WO | WO 00/03017 | 1/2000 |
| WO | WO 00/11175 | 3/2000 |
| WO | WO 00/12713 | 3/2000 |
| WO | WO 00/12714 | 9/2000 |
| WO | WO 2005/017114 | 2/2005 |

OTHER PUBLICATIONS

Alcoz et al., 1993, "Nitrogen Fertilization Timing Effect on Wheat Production. Nitrogen Uptake Efficiency, and Residual Soil Nitrogen ", Agronomy J. 85:1198-1203.

Allison et al. 1986, "The nucleotide sequence of the coding region of tobacco etch virus genomic RNA: evidence for the synthesis of a single polyprotein", Virology 154:9-20.

Anjorin and Obigbesan, 1985, "", International Cooperation for Effective Plantain and Banana Research, Proceedings of the 3$^{rd}$ Meeting, Abidjan. Ivory Coast, pp. 115-117.

Arcondeguy et al., 2001, "P(II) signal transduction proteins, pivotal players in microbial nitrogen control", Microhiol. Mol. Biol. Rev. 6580-105.

Asoegwu, 1987, "Effect of Irrigation and Nitrogen on the Growth and Yield of Pineapples (*Aunas cobosus*) cv Smooth Cayenne.", Fruits 42:505-509.

Asoegwu, 1988, "Nitrogen and potassium requirement of pineapple in relation to irrigation in Nigeria", Fertilizer Res. 15:203-210.

Ballas et al., 1989, "Elfficient functioning of plant promoters and poly(A) sites in Xenopus oocytes", Nucl. Acids Res. 17:7891-7903.

Bates, 1999, "Plant transformation via protoplast electroporation", Methods Mol. Biol. 111:359-366.

Bechtold et al., 1993, "In planta Agrobacterium gene transfer by infiltration of adult Arahidopsis thaliana plants", C.R. Acad. Sci. Paeis, Life Sciences 316:1194-1199.

Berry-Lowe et al., 1982, "The nucleotide sequence, expression, and evolution of one member of a multigene family encoding the small subunit of ribulose-1,5-bisphosphate carboxylase in soybean", J. Mol. Appl. Genet. 1483-498.

Bevan, 1984, "Binary *Agrobacterium* vectors for plant transformation ", Nucleic Acids Res. 12:8711-8721.

Binford et al., 1992, "Relationships between Corn Yields and Soil Nitrate in Late Spring", Agron. J. 84:53-59.

Bogusz et al., 1990, "Nonlegume hemoglobin genes retain organ-specific expression in heterologous transgenic plants", Plant Cell 2:633-641.

Bollig et al., 1978, "Effects of cAMP, theophylline, imidazole, and 4-(3,4-dimethoxybenzyI)-2-imidazolidone on the leaf movement hythm of *Trifolium repens* —a test of the cAMP-hypothesis of circadian rhythms", Planta 141:225-230.

Bonke et al., 2003, "APL regulates vascular tissue identity in Arabidopsis", Nature 426:181-186.

Bradshaw et al., 1995, "A new vector for recombination-based cloning of large DNA fragments from yeast artificial chromosomes", Nuel. Acids Res. 23:4850-4856.

Brenner et al., 2000, "Arabidopsis mutants resistant to S(+)-beta-methyl-alpha, beta-diaminopropionic acid, a cycad-derived glutamate receptor agonist", Plant Physiol. 124:1615-1624.

Brisson et al., 1984, "Expression of a bacterial gene in plants by using a viral vector", Nature 310:511-514.

Broglie et al., 1984, "Light-regulated expression of a pea ribulose-I,5-bisphosphate carboxylase small subunit gene in transformed plant c", Science 224:838-843.

Bunning and Moser, 1973, "Light-induced phase shills of circadian leaf movements of Phaseolus: Comparison with the effects of potassium and of ethyl alcohol", Proc. Natl. Acad. Sci. USA 70:3387-3389.

Burke et al., 1987, "Cloning of large segments of exogenous DNA into yeast by means of artificial chromosome vectors", Science 236:806-812.

Bytebier et al., 1987, "T-DNA organization in tumor cultures and transgenic plants of the monocotyledon *Asparagus officinalis*", Proc. Natl. Acad. Sci. USA 84:5345-5349.

Canevascini et al., 1996, "Tissue-specific expression and promoter analysis of the tobacco ltp1 gene", Plant Physiol. 112:513-524.

Cao et al., 1992, "Regeneration of herbicide resistant transgenic rice plants following microprojectile-mediated transformation of suspension culture cells", Plant Cell Rep. 11:585-591.

Capone et al., 1994, "Expression in different populations of cells of the root meristem is controlled by different domains of the rolB promoter", Plant Mol. Biol. 25:681-691.

Cashmore, 1983, "Nuclear genes encoding the small subunit of ribulose-1,5-bisphosphate carboxylase", in: Genetic Engineering of Plants: An Agricultural Perspective, Kosuge et al., eds., Plenum, NY, pp. 29-38.

Cerne, 1990, "Different kinds and levels of nitrogen nutrition in tomatoes", Acta Hort. 277:179-182.

Chen et al., 1992, "Soybean nodulation and grain yield as influenced by N-fertilizer rate, plant population density and cultivar in southern Quebec ", Can. J. Plant Science 72:1049-1056.

Chen et al., 1996, "The promoter of a H2O2-inducible, Arabidopsis glutathione S-transferase gene contains closely linked OBF- and OBP1-binding sites", Plant J. 10:955-966.

Christou et al., 1988, "Stable transformation of soybean callus by DNA-coated gold particles", Plant Physiol. 87:671-674.

Chiristou et al., 1989, "Production of Transgenic Rice (*Oryzu Sutiva* L.) Plants from Agronomically Important Indica and Japonica Varieties via Electric Discharge Particle Acceleration of Exogenous DNA into Immature Zygotic Embryos", Bio/Technology 9:957-962.

Chiristou and Ford, 1995, "Parameters influencing stable transformation of rice immature embryos and recovery of transgenic plants using electric discharge psrticle acceleration", Annals Botany 75:407-413.

Cordero et al., 1992, "Induction of PR proteins in germinating maize seeds infected with the fungus *Fusarium moniliforme*", Physiol. Mol. Plant Pathol. 41:189-200.

Cordero et al., 1994, "Expression of a maize proteinase inhibitor gene is induced in response to wounding and fungal infection: systemic wound-response of a monocot gene", Plant J. 6:141-150.

Coruzzi et al., 1983, "Nucleotide sequences of two pea cDNA clones encoding the small subunit of ribulose 1,5-bisphosphate carboxylase and the major chlorophyll a/b-binding thylakoid polypeptide", J. Biol. Chem. 258:1399-1402.

Coruzzi et al., 1984, "Tissue-specific and light-regulated expression of a pea nuclear gene encoding the small subunit of ribulose-1,5-bisphosphate carboxylase", EMBO J. 3:1671-1679.

Covington et al., 2001, "ELF3 modulates resetting of the circadian clock in Arabidopsis", Plant Cell 131305-1315.

Datta et al., 1990, "Genetically Engineered Fertile Indica-Rice Recovered from Protoplasts", Bio/Technology 8:736-740.

Davuluri et al., 2003, "AGRIS: Arabidopsis gene regulatory information server, an information resource of Arabidopsis cis-regulatory elements and transcription factors", BMC Bioinformatics 4:25.

(56) References Cited

OTHER PUBLICATIONS

De Framond et al., 1983, "Mini-Ti: A New Vector Strategy for Plant Genetic Engineering", Bio/Technology 1:262-269.
Della-Cioppa et al., 1987, "Protein Trafficking in Plant Cells", Plant Physiol. 84:965-968
De Wet et al., 1985, in: The Experimental Manipulation of Ovule Tissues, Chapman et al., eds. Longman, MY, pp. 197-209.
D'Halluin et al., 1992, "Transgenic Maize Plants by Tissue Electroporation", Plant Cell 4:1495-1505.
Diepenbrock and Porksen, 1992, "Effect of stand establishment and nitrogen fertilization on yield and yield physiology of linseed (*Linum usitatissimum* L.)", Industrial Crops and Products 1:165-173.
Draycott et al., 1983, "", Symposium Nitrogen and Sugar Beet, International Institute for Sugar Beet Research, Brussels, Belgium. pp. 293-303.
Duan et al., 1996, "Transgenic rice plants harboring an introduced potato proteinase inhibitor II gene are insect resistant", Nature Biotechnol. 14:494-498.
Dunsmuir et al., 1983, "The major chlorophyll a/b binding protein of petunia is composed of several polypeptides encoded by a number of distinct nuclear genes", J. Mol. Appl. Genet. 2:285-300.
Eckelkamp et al., 1993, "Wound-induced systemic accumulation of a transcript coding for a Bowman-Birk trypsin inhibitor-related protein in maize (*Zea mays* L.) seedlings", FEBS Lett. 323:73-76.
Edwards et al., 1990, "Cell-specitic expression in transgenic plants reveals nonoverlapping roles for chloroplast and cytosolic glutamine synthetase", Proc. Natl. Acad.: Sci. USA 87:3459-3463.
Elroy-Stein et al., 1989, "Cap-independent translation of mRNA conferred by encephalomyocarditis virus 5' sequence improves the performance of the vaccinia virus/bacteriophage T7 hybrid expression system", Proc. Natl. Acad. Sci. USA 86:6126-6130.
Evans et al., 1983, "Protoplasts, isolation and culture", in: Handbook of Plant Cell Culture, Macmillan Publishing Co., New York, pp. 124-176.
Feillet et al., 2006, "Lack of bod anticipation in Per2 mutant mice", Curr. Biol. 16:2016-2022.
Finer and McMullen, 1991, "Transformation of soybean via particle bombardment of embryogenic suspension culture tissue", In Vitro Cell and Develop. Biol-Plant 27P:175-182.
Finer et al., 1999, "Particle bombardment mediated transformation", Curr. Top. Microbiol. Immunol. 240:59-80.
Fitter et al., 2002, "GLK gene pairs regulate chloroplast development in diverse plant species", The Plant J. 31:713-727.
Forde, 2002, "Local and long-range signaling pathways regulating plant responses to nitrate", Ann. Rev. Plant Biol. 53:203-224.
Fraley et al., 1981, "New generation liposomes: the engineering of an efficient vchicle for intracellular delivery of nucleic acids", Trends Biochem. Sci. 6:77-80.
Fraley et al., 1983. "Expression of bacterial genes in plant cells", Proc. Natl. Acad. Sci. USA 80:4803-4807.
Freeman et al., 1984, "A comparison of methods for plasmid delivery into plant protoplasts", Plant Cell Physiol. 25:1353-1365.
Frischauf et al., 1983, "Lambda replacement vectors carrying poly linker sequences", J. Mol. Biol. 170:827- 842.
Fromm et al., 1990, "Inheritance and expression of chimeric genes in the progeny of transgenic maize plants", Bio/Technology 8:833-839.
Fromm et al., 1985, "Expression of genes transferred into monocot and dicot plant cells by electroporation", Proc. Natl. Acad. Sci. USA 82:5824-5828.
Gallie et al., 1989, in: Molecular Biology of RNA, Cech, ed., Liss, NY, pp. 237-256.
Gatz et al., 1991, "Regulation of a modified CaMV 35S promoter by the Tn10-encoded Tet repressor in transgenic tobacco", Mol. Gen Genet. 227:229-237.
Gibon et al., 2006, "Integration of metabolite with transcript and enzyme activity profiling during diurnal cycles in Arabidopsis rosettes", Genome Biol. 7R76.
Goff et al., 1990, "Transactivation of anthocyanin biosynthetic genes following transfer of B regulatory genes into maize tissues", EMBO J. 9:2517-2522.
Gordon-Kamm et al., 1990, "Transformation of Maize Cells and Regeneration of Fertile Transgenic Plants", The Plant Cell 2:603-618.
Gregoriadis, 1985, "Liposomes for drugs and vaccines", Trends Biotechnol. 3:235-241.
Gruber et al., 1993, "Vectors for plant transformation", in: Methods in Plant Molecular Biology & Biotechnology, Glich et al., eds., CRC Press, pp. 89-119.
Grubinger et al., 1993, "Tomato Response to Starter Fertilizer, Polyethylene Mulch, and Level of Soil Phosphorus", J. Am. Soc. Hort. Sci. 118:212-216.
Guerineau et al., 1991, "Effect of deletions in the cauliflower mosaic virus polyadenylation sequence on the choice of the polyadenylation sites in tobacco protoplasts ", Mol. Gen. Genet. 262:141-144.
Guevara-Garcia et al., 1993, "Tissue-specific and wound-inducible pattern of expression of the mannopine synthase promoter is determined by the interaction between positive and negative cis-regulatory elements", Plant J. 4:495-505.
Guo et al., 2005, "DATF: a database of Arabidopsis transcription factors", Bioinformatics 21:2568-2569.
Gurley et al., 1986, "Upstream sequences required for efficient expression of a soybean heat shock gene", Mol. Cell. Biol. 6:559-565.
Gutierrez et al., 2007, "Qualitative network models and genome-wide expression data define carbon/nitrogenresponsive molecular machines in Arabidopsis", Genome Biol. 8R7.
Hamilton et al., 1996, "Stable transfer of intact high molecular weight DNA into plant chromosomes.", Proc. Acad. Sci. USA 93:9975-9979.
Hansen et al., 1997, "Wound-inducible and organ-specific expression of ORF13 from Agrobacterium rhizogenes 8196 F-DNA in transgenic tobacco plants", Mol. Gen. Genet 354:337-343.
Harmer et al., 2000, "Orchestrated transcription of key pathways in Arabidopsis by the circadian clock", Science 290:2110-2113.
Haseeoff et al., 1997, "Removal of a cryptic intron and subcellular localization of green fluorescent protein are required to mark transgenic Arabidopsis plants brightly", Proc. Natl. Acad. Sci. USA 94:2122-2127.
Hegde and Srinivas, 1991, "", Tropical Agriculture 68:331-334.
Hershey and Stoner, 1991, "Isolation and characterization of cDNA clones for RNA species induced by substituted benzenesullonamides in corn", Plant Mol. Biol. 17:679-690.
Hiei et al., 1994, "Efficient transformation of rice (*Oryza sativa* L.) mediated by Agrobacterium and sequence analysis of the boundaries of the T-DNA", The Plant J. 6:271-282.
Hirel et al., 1992, "Forcing expression of a soybean root glutamine synthetase gene in tobacco leaves induces a native gene encoding cytosolic enzyme", Plant Mol. Biol. 20:207-218.
Hoekema et al., 1983, "A binary plant vector strategy based on separation of vir- and T-region of the *Agrobacterium tumefaciens* Ti-plasmid", Nature 303:179-180.
Hooykaas-Van Slogteren et al., 1984, "Expression of Ti plasmid genes in monocotyledonous plants infected with *Agrobacterium turnefaciens*", Nature 311:763-764.
Horsch et al., 1985, "Simple and General Method for Transferring Genes into Plants", Science 227:1229-1231.
Howard and Lessman, 1991, "Nitrogen Fertilization of heat Double-Cropped Following Grain Sorghum in a No-Tillage System", Agron. J. 83:208-211.
Hsieh et al., 1998. "A PII-like protein in Arabidopsis: putative role in nitrogen sensing", Proc. Natl. Acad. Sci. USA 95:13965-13970.
Human and Kotze, 1990, "", Communications in Soil Science and Plant Analysis 21:771-782.
Huynh et al., 1985, "", in: DNACloning, A Practical Approach, vol. 1, Glover, ed Oxford: IRL Press, p. 49-78.
Ishida et al., 1996, "High efficiency transformation of maize (*Zea mays* L.) mediated by Agrobacterium tumefaciens", Nature Biotechnol. 14:745-750.

(56) References Cited

OTHER PUBLICATIONS

Jakoby et al., 2002, "bZIP transcription factors in Arabidopsis", Trends Plant Sci. 7:106-111.
Jefferson, 1987, "Assaying chimeric genes in plants: The GUS gene fusion system", Plant Molec. Biol.Rep. 5:387-405.
Jobling and Gherke, 1987, "Enhanced translation of chimaeric messenger RNAs containing a plant viral untranslated leader sequence", Nature 325:622-625.
Joshi, 1987, "Putative polyadenylation signals in nuclear genes of higher plants: a compilation and analysis", Acids Res. 15:9627-9640.
Kaeppler et al., 1990, "Silicon carbide liber-mediated DNA delivery into plant cells", Plant Cell Reports 9:415-418.
Kaeppler et al., 1992, "Silicon carbide fiber-mediated stable transformation of plant cells", Theor. Appl. Genet. 84:560-566.
Kawamata et al., 1997, "Temporal and spatial pattern of expression of the pea phenylalanine ammonia-lyase genel promoter in transgenic tobacco", Plant Cell Physiol. 38:792-803.
Keller and Baumgartner, 1991, "Vascular-specific expression of the bean GRP 1.8 gene is negatively regulated", Plant Cell 3:1051-1061.
King et al., 1993, "Feedback Regulation of Nitrate Influx in Barley Roots by Nitrate, Nitrite, and Ammonium", Plant Physiol. 102:1279-1286.
Klee et al., 1987, "Transactivation of anthocyanin biosynthetic genes following transfer of B regulatory genes into maize tissues", Annu. Rev. Plant Physiol. 38:467-486.
Klein et al., 1989 "Genetic transformation of maize cells by particle bombardment", Plant Physiol. 91:440-444.
Klein et al., 1988, "Transfer of foreign genes into intact maize cells with high-velocity microprojectiles", Proc. Natl. Acad. Sci. USA 85:4305-4309.
Klein et al., 1988, "Factors Influencing Gene Delivery into *Zea Mays* Cells by High-Velocity Microprojectiles", Bio/Technology 6:559-563.
Klein et al., 1992, "Transformation of Microbes, Plants and Animals by Particle Bombardment", Bio/Technology 10:286-291.
Komari et al. 1998, "Advances in cereal gene transfer", Curr. Opin. Plant Biol. 1:161-165.
Kondo, 1983, "Phase Shifts of Potassium Uptake Rhythm in *Lemna gibba* G3 Due to Light, Dark or Temperature Pulses", Plant Cell Physiol. 24:659-665.
Koziel et al., 1993, "Field Performance of Elite Transgenic Maize Plants Expressing an Insecticidal Protein Derived from *Bacillus thuringiensis*", Biotechnology 11:194-200.
Küster et al., 1993, "The sucrose synthase gene is predominantly expressed in the root nodule tissue of *Vicia faba*", Mol. Plant Microb. Interact. 6:507-514.
Këster et al., 1995, "The promoter of the *Vicia faba* L. VfENOD-GRP3 gene encoding a glycine-rich early nodulin mediates a predominant gene expression in the interzone II-III region of transgenic Vicia hirsuta root nodules", Plant Mol. Biol. 29:759-772.
Lacombe et al., 2001, "The identity of plant glutamate receptors", Science 292:1486-1487.
Lam et al., 1994, "Metabolic regulation of the gene encoding glutamine-dependent asparagine synthetase in Arabidopsis thaliana", Plant Physiol. 106:1347-1357.
Lam, 1994, "Analysis oftissue-specific elements in the CaMV 35S promoter", Results Probl. Cell Differ. 20:181-196.
Lam et al., "Reciprocal regulation ofdistinct asparagine synthetase genes by light and metabolites in Arabidopsis thaliana", Plant J. 16:345-353.
Langenegger and Smith, 1988, "Nitrogen requirements of bananas in South Africa", Fruits 43:639-643.
Leach and Aoyagi, 1991, "Promoter analysis of the highly expressed rolC and rolD root-inducing genes of Agrobacterium rhizogenes: enhancer and tissue-specific DNA determinants are dissociated", Plant Sci. 79:69-76.

Letchamo, 1992, "A comparative study of camomile yield, essential oil and flavonoids content under two sowing seasons and nitrogen levels", Acta Hort. 306:375-384.
Li et al., 1993, "An improved rice transformation system using the biolistic method", Plant Cell Rep. 12:250-255.
Lippman et al., 2005, "Profiling DNA methylation patterns using genomic tiling microarrays", Nature Meth. 2:219-224.
Little et al., 2005, "The putative high-affinity nitrate transporter NRT2.I represses lateral root initiation in response to nutritional cues", Proc. Natl. Acad. Sci. USA 102:13693-13698.
Lommel et al., 1991, "Identification of the maize chlorotic mottle virus capsid protein cistron and characterization of its subgenomic messenger RNA", Virology 181:382-385.
Lopez-Bucio et al., 2003, "The role of nutrient availability in regulating root architecture", Curr. Opin. Plant Biol. 6:280-287.
Macejak and Sarnow, 1991, "Internal initiation of translation mediated by the 5' leader of a cellular mRNA", Nature 353:90-94.
Magistad et al., 1932, "Yields of Pineapples as Inflenced by Fertilization and Conformity to the Law of Diminishing Increment", J. Am. Soc. Agron. 24:610-622.
Mahalle and Seth, 1989, "", Indian J. Agr. Sci. 59:395-397.
Malamy, 2005, "Intrinsic and environmental response pathways that regulate root system architecture", Plant Cell Environ, 2867-77.
Marineau et al., 1987, "Differential accumulation of potato tuber mRNAs during the hypersensitive response induced by arachidonic acid", Plant Mol. Biol. 9:335-342 1.
Matsuoka et al., 1993, "Tissue-specific light-regulated expression directed by the promoter of a C4 gene, maize pyruvate,orthophosphate dikinase, in a C3 plant, rice", Proc. Natl. Acad. Sci. USA 90:9586.
Matton and Brisson, 1989, "Cloning, expression, and sequence conservation of pathogenesis-related gene transcripts of potato", Molecular Plant-Microbe Interactions 2:325-331.
McCabe et al., 1988, "Stable Transformation of Soybean (*Glycine Max*) by Particle Acceleration", Bio/Technology 6:923-926.
McClung, 2001, "Circadian rhythms in plants", Ann. Rev. Plant thysiol. Plant Mo. Biol. 52:139-162.
McClung, 2006, "Plant circadian rhythms", Plant Cell 18:792-803.
McGurl et al., 1992, "Structure, expression, and antisense inhibition of the systemin precursor gene" Science 225:1570-1573.
McNellis et al., 1998, "Glucocorticoid-inducible expression of a bacterial avirulence gene in transgenic Arabidopsis induces hypersensitive cell death", Plant J. 14:247-257.
Mett et al., 1993, "Copper-controllable gene expression system for whole plants", Proc. Natl. Acad. Sci. USA 90:4567-4571.
Miao et al., 1991, "Ammonia-regulated expression of a soybean gene encoding cytosolic glutamine synthetase in transgenic Lotus comiculatus", Plant Cell 3:11-22.
Miles, 1934, "The Use of Small Amounts of Nitrogen for Corn in Addition to Phosphorus and Potassium", J. Am. Soc. Agronomy 26:129-137.
Millar, 2004, "Input signals to the plant circadian clock", J. Exp. Bot. 55:277-283.
Mogen et al., 1990. "Upstream sequences other than AAUAAA are required for efficient messenger RNA 3'- end formation in plants", Plant Cell 2:1261-1272.
Munroe and Jacobson, 1990, "Tales of poly(A): a review", Gene 91:151-158.
Munsi, 1992, "Nitrogen and phosphorus nutrition response in Japanese mint cultivation", Acta Horticulturae 306 :436-443.
Murashige et al., 1962, "", Plant Physiol. 15:473-497.
Murray et al., 1989, "Codon usage in plant genes", Nucl. Acids Res. 17:477-498.
Oard, 1991, "Physical methods for the transformation of plant cells", Biotech. Adv. 9:1-11.
Odell et al., 1985, "Identification of DNA sequences required for acticity of the cauliflower mosaic virus 35S promoter", Nature 313:810-812.
Oliviera and Coruzzi, 1999, "Carbon and amino acids reciprocally modulate the expression of glutamine synthetase in Arabidopsis", Plant Physiol. 121:301-310.

(56) References Cited

OTHER PUBLICATIONS

Oliviera et al., 2001, "Metabolite and light regulation of metabolism in plants: lessons from the study of a single biochemical pathway", Braz. J. Med. Biol. Res. 34:567-575.
Oritani and Yoshida, 1984, "Studies on Nitrogen Metabolism in Crop Plants : XVIII. Utilization of nitrogen fertilizer on leaf area growth, protein synthesis and sink formation in the rice plant", Japanese J. Crop Sci. 53:204-212.
Orozco and Ogren, 1993, "Localization of light-inducible and tissue-spccitic regions of the spinach ribulose hisphosphate carboxylaseioxyenase (rubisco) activase promoter in transgenic tobacco plants", Plant Mol. Biol. 23:1129-1138.
Ow et al., 1986, "Transient and Stable Expression of the Firefly Luciferase Gene Plant Cells and Transgenic Plants", Science 234:856-859.
Paszkowski et al., 1994, "Direct gene transte to plants", EMBO J. 3:2717-2722.
Zhang and Wu, 1988, "Efficient regeneration of transgenic rice plants from rice protoplasts and correctly regulated expression of foreign genes in the plants", Theor. Appl. Genet. 76:835-840.
Pilgrim et al., 1993, "Circadian and light-regulated expression of nitrate reductase in Arabidopsis", Plant Mol. Biol. 23:349-364.
Plautz et al., 1997, "Quantitative analysis of *Drosophila* period gene transcription in living animals", J. Biol. Rhythms 12:204-217.
Porta and Lomonossoff, 1996, "Use of viral replicons for the expression of genes in plants", Mol. Biotechnol. 5:209-221.
Porter and Sisons, 1991, "Petiole nitrate content of Maine-grown Russet Burbank and Shepody potatoes in response to varying nitrogen rate", Am. Potato J. 68:493-505.
Proudfoot, 1991, "Poly(A) signals", Cell 64:671-674.
Rahn et al., 1992, "Improving the prediction of fertiliser nitrogen for brassica crops", Proceedings of the 2nd Congress of the European Society, of Agronomy, Warwick, 1992, pp. 424-425.
Rao and Dao, 1992, "Fertilizer Placement and Tillage Effects of Nitrogen Assimilation by Wheat", Agron. J, 84:1028-1032.
Rathore et al., 1993, "Use of bar as a selectable marker gene and for the production of herbicide-resistant rice plants from protoplasts", Plant Mol. Biol. 21:871-884.
Rawat et al., 1999, "AtAMT1 gene expression and NH4+ uptake in roots of Arabidopsis thaliana: evidence for regulation by root glutamine levels", Plant J. 19:143-152.
Redolfi et al., 1983, "Occurrence of pathogenesis-related (b) and similar proteins in different plant species", Neth. J. Plant Pathol. 89:245-254.
Remans et al., 2006, "The Arabidopsis NRT1.1 transporter participates in the signaling pathway triggering root colonization of nitrate-rich patches", Proc. Natl. Acad. Sci. USA 103:19206-19211.
Richardson and Hargrave, 1992, "Effect of temperature, carbon dioxide enrichment, nitrogen form and rate of nitrogen fertiliser on the yield and nitrate content of two varieties of glasshouse lettuce", J. Sci. Food Agric. 59:345-349.
Riggs and Bates, 1986, "Stable transformation of tobacco by electroporation: evidence for plasmid concatenation", Proc. Natl. Acad. Sci. USA 83:5602-5606.
Rinehart et al., 1996, "Tissue-specific and developmental regulation of cotton gene FbL2A. Demonstration of promoter activity in transgenic plants", Plant Physiol. 112:1331-1341.
Rohrmeier and Lehle, 1993, "WIP1, a wound-inducible gene from maize with homology to Bowman-Birk proteinase inhibitors", Plant Mol. Biol. 22:783-792.
Rook et al., 1998, "Sucrose-specitic signalling represses translation of the Arabidopsis ATB2 bZIP transcription factor gene", Plant J. 15:253-263.
Ryan, 1990, "Protease Inhibitors in Plants: Genes for Improving Defenses Against Insects and Pathogens", Ann. Rev. Phytopath. 28:425-449.
Salome et al., 2002, "The out of phase I mutant defines a role for PHYB in circadian phase control in Arabidopsis", Plant Physiol. 129:1674-1685.

Sanfacon et al., 1991, "A dissection of the cauliflower mosaic virus polyadenylation signal", Genes Dev. 5:141-149.
Sanford et al., 1987, "Delivery of substances into cells and tissues using a particle bombardment process", Particulate Science and Technology 5:27-37.
Sanford et al., 1991, "An improved, helium driven biolistic device", Technique 3:3-16.
Sanger et al., 1990, "Characteristics of a strong promoter from figwort mosaic virus: comparison with the analogous 35S promoter from cauliflower mosaic virus and the regulated mannopine synthase promoter", Plant Mol. Biol. 14:433-443.
Scheible et al., 1997, "Nitrate Acts as a Signal to Induce Organic Acid Metabolism and Repress Starch Metabolism in Tobacco", Plant Cell 9:783-798.
Scheible et al., 2004, "Genome-wide reprogramming of primary and secondary metabolism, protein synthesis, cellular growth processes, and the regulatory infrastructure of Arabidopsis in response to nitrogen", Plant Physiol. 136:2483-2499.
Scfiena et al., 1991, "A steroid-inducible gene expression system for plant cells", Proc. Natl. Acad. Sci. USA 88:10421-10425.
Severn and Schöffl, 1991, "Heat-inducible hygromycin resistance in transgenic tobacco", Plant Mol. Biol. 15:827-833.
Shimamoto et al., 1989, "Fertile transgenic rice plants regenerated from transformed protoplasts", Nature 338:274-276.
Shimamoto, 1994, "Gene expression in transgenic monocots ", Curr. Opin. Biotechnology 5:158-162.
Shizuya et al., 1992, "Cloning and stable maintenance of 300-kilobase-pair fragments of human DNA in *Escherichia coli* using an F-factor-based vector", Proc. Natl. Acad. Sci. USA 89:8794-8797.
Siebertz et al., 1989, "cis-analysis of the wound-inducible promoter wun1 in transgenic tobacco plants and histochemical localization of its expression", Plant Cell 1:961-968.
Singh et al. 1998, "Cytological haracteriz ion of transgenic soybean", Theor. Appl. Genet. 96:319-324.
Sisson et al., 1991, "Nitrogen-Use Efficiency among Flue-Cured Tobacco Genotypes", Crop Sci. 31:1615-1620.
Somers et al., 1992, "Transgenic Oat Plants", Bio/Technology 10:1589-1594.
Somssich et al., 1986, "Rapid activation by fungal elicitor of genes encoding "pathogenesis-related" proteins in cultured parsley cells", Proc. Natl. Acad. Sci. USA 83:2427-2430.
Somssich et al., 1988, "Gene structure and in situ transcript localization of pathogenesis-related protein 1 in parsley", Mol. Gen. Genet. 213:93-98.
Stanford et al., 1989, "Differential expression within a family of novel wound-induced genes in potato", Mol. Gen Genet. 215:200-208.
Stephan, 2002, "The "other" circadian system: food as a Zeitgeber", J. Biol. Rhythms 17:284-292.
Sternberg, 1990, "Bacteriophage P1 cloning system for the isolation, amplification, and recovery of DNA fragments as large as 100 kilobase pairs", Proc. Natl. Acad. Sci. USA 87:103-107.
Straw et al, 1993, "", Tennessee Farm and Home Science: Progress Report 166:20-24.
Sykova, 2004, "Extrasynaptic volume transmission and diffusion parameters of the extracellular space", Neuroscience 129:861-876.
Takamatsu et al., 1987, "Expression of bacterial chloramphenicol acetyltransferase gene in tobacco plants mediated by TMV-RNA", EMBO J. 6:307-311.
Teeri et al., 1989, "Gene fusions to lacZ reveal new expression patterns of chimeric genes in transgenic plants", EMBO J. 8:343-350.
Thum et al., 2003, "Light- and carbon-signaling pathways. Modeling circuits of interactions", Plant Physiol. 132:440-452.
Tian et al., 2004, "High-throughput fluorescent tagging of full-length Arabidopsis gene products in planta", Plant Physiol. 135:25-38.
Tingly et al., 1987, "Glutamine synthetase genes of pea encode distinct polypeptides which are differentially expressed in leaves, roots and nodules", EMBO J. 6:1-9.
Tollenaar and Mihajlovic, 1993, "Corn Growth Following Cover Crops: Intluence of Cereal Cultivar, Cereal Removal, and Nitrogen Rate", Agron. J. 85:251-255.

(56) References Cited

OTHER PUBLICATIONS

Tomes et al., 1995, "Direct DNA transfer into intact plant cells via microprojectile bombardment", in: Plant Cell, Tissueand Organ Culture: Fundamental Methods, Ganborg and Phillips, eds., Springer-Verlag, Berlin.
Toriyama et al., 1988, "Transgenic Rice Plants After Direct Gene Transfer into Protoplasts", Biotechnology 6:1072-1074.
Uknes et al., 1992, "Acquired resistance in Arabidopsis", Plant Cell 4:645-656.
Vain et al., 1995, "Foreign gene delivery into monocotyledonous species", Biotechnol. Adv. 13:653-671.
Van Camp et al., 1996, "Tissue-specitic activity of two manganese superoxide dismutase promoters in transgenic tobacco", Plant Phsiol. 112:525-535.
Van Helden, 2003, "Regulatory sequence analysis tools", Nucl. Acids Res. 31:3593-3596.
Van Loon, 1985, "Pathogenesis-related proteins", Plant Mol. Biol. 4:111-116.
Vasii et al., 1992, "Herbicide Resistant Fertile Transgenic Wheat Plants Obtained by Microprojectile Bombardment of Regenerable Embryogenic Callus", Bio/Technology 10:667-674.
Vasil, 1994, "Molecular improvement of cereals", Plant Mol. Biol. 25 925-937.
Vasil, 1996, "Milestones in crop biotechnology?Transgenic cassava and Agrobacterium-mediated transformation of maize", Nature Biotechnology 14:702-703.
Velten et al;, 1984, "Isolation of a dual plant promoter fragment from the Ti plasmid of *Agrobacterium tumefaciens*", EMBO J. 3:2723-2730.
Wallace et al., 1990, "Influence of nitrogen fertilization on morphological development of indeterminate and determinate soybeans", J. Plant Nutrition 13:1523-1537.
Walch-Liu et al., 2006, "Nitrogen regulation of root branching", Ann Bot (lond) 97:875-881.
Walden et al. 1990, "", Meth. Mol. Cell Biol. 1:175-194.
Walters et al., 1992, "Transformation and inheritance of a hygromycin phosphotransferase gene in maize plants", Plant Mol. Biol. 18:189-200.
Wang and Tobin, 1998, "Constitutive expression of the circadian clock associated 1 (CCA1) gene disrupts circadian rhythms and suppresses its own expression", Cell 93:1207-1217.
Wang et al., 2003, "Microarray analysis of the nitrate response in Arabidopsis roots and shoots reveals over 1,000 rapidly responding genes and new linkages to glucose, trehalose-6-phosphate, iron, and sulfate metabolism", Plant Physiol. 132:556-567.
Wang et al., 2004, "Genomic analysis of the nitrate response using a nitrate reductase-null mutant of Arabidopsis", Plant Physol. 136:2512-2522.
Warner et al., 1993, "Isolation of an asparagus intracellular PR gene (AoPRI) wound-responsive promoter by the inverse polymerase chain reaction and its characterization in transgenic tobacco", Plant J. 3:191-201.
Weeks et al., 1993, "Rapid Production of Multiple Independent Lines of Fertile Transgenic Wheat (*Triticum aestivum*)", Plant Physiol. 102:1077-1084.
Weising et al., 1988, "Foreign genes in plants: transfer, structure, expression, and applications", Ann. Rev. Genetics 22:421-477.
Wong et al., 2004, "Correlation of ASN2 gene expression with ammonium metabolism in Arabidopsis", Plant Physiol, 134:332-338.
Xu et al., 1995, "Characterization or a rice gene family ncoding root-specific proteins", Plant Mol. Biol. 27:237-248.
Yadav and Sharma, 1983, "", Indian J. Agr. Sci. 53:38-43.
Yamamoto et al., 1991, "Characterization of cis-acting sequences regulating root-specific gene expression in tobacco", Plant Cell 3:371-382.
Yamamoto et al., 1994, "The promoter of a pine photosynthetic gene allows expression of a beta-glucuronidase reporter gene in transgenic rice plants in a light-independent but tissue-specific manner", Plant Cell Physiol. 35:773-778.
Yamamoto et al., 1997, "Light-responsive elements of the tobacco PSI-D gene are located both upstream and within the transcribed region", Plant J. 12:255-265.
Yang and Klessig, 1996, "Isolation and characterization of a tobacco mosaic virus-inducible myb oncogene homolog from tobacco", Proc. Natl. Acad. Sci. USA 93:14972-14977.
Yasumura et al., 2005 "A Conserved Transcription Factor Mediates Nuclear Control of Organelle Biogenesis in Anciently Diverged Land Plants" Plant Cell. 17:1894-1907.
Zhang et al., 1988, "Transgenic rice plants produced by electroporation-mediated plasmid uptake into protoplasts", Plant Cell Rep. 7:379-384.
Zhang and Singh, 1994, "ocs element promoter sequences are activated by auxin and salicylic acid in Arabidopsis", Proc. Natl. Acad. Sci. USA 91:2507-2511.

\* cited by examiner

| TRANSGENE | TARGET 1 | TARGET 2 | TARGET 3 | N-assimilation GLN1 Gln synthesis | N-storage ASN1 Asn synthesis | Recycle N GDH1 Glu degradation | CROP | Examples |
|---|---|---|---|---|---|---|---|---|
| | GLN1.3 | BZIP/ASN1 | GDH1 | | | | | |
| GLN GROUP | | | | | | | | |
| CCA1-UP | UP | DOWN | DOWN | MORE GLN | less Asn | more Glu | VEGETATIVE | trees, tobacco, lettuce, potato, |
| GLK1-UP | UP | DOWN | DOWN | MORE GLN | less Asn | more Glu | VEGETATIVE | as above |
| BZIP-DOWN | NC | DOWN | NC | | less Asn | | VEGETATIVE | as above |
| ASN GROUP | | | | | | | | |
| CCA1-DOWN | DOWN | UP | UP | less Gln | MORE ASN | less Glu | FRUIT/SEED | Brassica (including canola), corn, soybean, cotton, rice, wheat, safflower, sunflower, tomato |
| GLK1-DOWN | DOWN | UP | UP | less Gln | MORE ASN | less Glu | FRUIT/SEED | as above |
| BZIP-UP | NC | UP | NC | | MORE ASN | | FRUIT/SEED | as above |

Genes for 3 sequential REACTIONS in N-assimilation whose genes are reciprocally regulated by CCA1 and GLK1:

GLN1.3 gene (GLUTAMINE SYNTHETASE) functions in assimilating inorganic N (ammonium) into glutamine (primary n-assimilation).
Reaction: NH4 + GLU = GLN (reactive, N-donor in synthesis of all DNA, amino acids, chlorophyll, etc)

ASN1 gene (ASPARAGINE SYNTHETASE) functions to convert assimilated GLN to ASN (inert, for N-transport to seed & N-storage):
Reaction: GLN + ASP = ASN + GLU GDH1 gene (GLUTAMATE DEHYDROGENASE) functions to deaminate the GLU by-product of ASN1 reaction
Reaction: Glu = NH4 + alpha Ketoglutarate

FIG. 2

SEQUENCE LISTING

```
<160> NUMBER OF SEQ ID NOS: 14

<210> SEQ ID NO 1
<211> LENGTH: 16
<212> TYPE: DNA
<213> ORGANISM: Artificial Sequence
<220> FEATURE:
<223> OTHER INFORMATION: TAZ forward primer used for RT-qPCR

<400> SEQUENCE: 1
tcctcgtctc ggtctt                                                        16

<210> SEQ ID NO 2
<211> LENGTH: 16
<212> TYPE: DNA
<213> ORGANISM: Artificial Sequence
<220> FEATURE:
<223> OTHER INFORMATION: TAZ reverse primer used for RT-qPCR

<400> SEQUENCE: 2
caaccaccag ggattc                                                        16

<210> SEQ ID NO 3
<211> LENGTH: 19
<212> TYPE: DNA
<213> ORGANISM: Artificial Sequence
<220> FEATURE:
<223> OTHER INFORMATION: bZIP forward primer used for RT-qPCR
```

```
<400> SEQUENCE: 3
tcaggttccg acatagatg                                                  19

<210> SEQ ID NO 4
<211> LENGTH: 18
<212> TYPE: DNA
<213> ORGANISM: Artificial Sequence
<220> FEATURE:
<223> OTHER INFORMATION: bZIP reverse primer used for RT-qPCR

<400> SEQUENCE: 4
ccacggtgta cgtctaca                                                   18

<210> SEQ ID NO 5
<211> LENGTH: 22
<212> TYPE: DNA
<213> ORGANISM: Artificial Sequence
<220> FEATURE:
<223> OTHER INFORMATION: Primer 1 sequence used to amplify CCA1 binding
      site of the bZIP1 gene

<400> SEQUENCE: 5
gatcgaaaat aaggaaagtg gg                                              22

<210> SEQ ID NO 6
<211> LENGTH: 21
<212> TYPE: DNA
<213> ORGANISM: Artificial Sequence
<220> FEATURE:
<223> OTHER INFORMATION: Primer 2 sequence used to amplify CCA1 binding
      site of the bZIP1 gene

<400> SEQUENCE: 6
actggtcacc tattaaggaa c                                               21

<210> SEQ ID NO 7
<211> LENGTH: 20
<212> TYPE: DNA
<213> ORGANISM: Artificial Sequence
<220> FEATURE:
<223> OTHER INFORMATION: Primer 1 sequence used to amplify CCA1 binding
      site of the TOC1 gene

<400> SEQUENCE: 7
tggacggtgg agattaagtc                                                 20

<210> SEQ ID NO 8
<211> LENGTH: 20
<212> TYPE: DNA
<213> ORGANISM: Artificial Sequence
<220> FEATURE:
<223> OTHER INFORMATION: Primer 2 sequence used to amplify CCA1 binding
      site of the TOC1 gene

<400> SEQUENCE: 8
acgaaacgaa gccgaatcct                                                 20

<210> SEQ ID NO 9
<211> LENGTH: 24
<212> TYPE: DNA
<213> ORGANISM: Artificial Sequence
<220> FEATURE:
<223> OTHER INFORMATION: Primer 1 sequence used to amplify CCA1 binding
      site of the ZTL gene

<400> SEQUENCE: 9
```

```
agtcgccgga gattatgaag acgg                                            24

<210> SEQ ID NO 10
<211> LENGTH: 24
<212> TYPE: DNA
<213> ORGANISM: Artificial Sequence
<220> FEATURE:
<223> OTHER INFORMATION: Primer 2 sequence used to amplify CCA1 binding
      site of the ZTL gene

<400> SEQUENCE: 10
ggttttatct acttgacccg acag                                            24

<210> SEQ ID NO 11
<211> LENGTH: 23
<212> TYPE: DNA
<213> ORGANISM: Artificial Sequence
<220> FEATURE:
<223> OTHER INFORMATION: Primer 1 sequence used to amplify CCA1 binding
      site of the GDH1 gene

<400> SEQUENCE: 11
tgtttcaata gcattagcct cca                                             23

<210> SEQ ID NO 12
<211> LENGTH: 23
<212> TYPE: DNA
<213> ORGANISM: Artificial Sequence
<220> FEATURE:
<223> OTHER INFORMATION: Primer 2 sequence used to amplify CCA1 binding
      site of the GDH1 gene

<400> SEQUENCE: 12
tggggaatgt gacacacata atc                                             23

<210> SEQ ID NO 13
<211> LENGTH: 21
<212> TYPE: DNA
<213> ORGANISM: Artificial Sequence
<220> FEATURE:
<223> OTHER INFORMATION: Primer 1 sequence used to amplify CCA1 binding
      site of the GLN1.3 gene

<400> SEQUENCE: 13
ttgaatccga agaggggaaa a                                               21

<210> SEQ ID NO 14
<211> LENGTH: 23
<212> TYPE: DNA
<213> ORGANISM: Artificial Sequence
<220> FEATURE:
<223> OTHER INFORMATION: Primer 2 sequence used to amplify CCA1 binding
      site of the GLN1.3 gene

<400> SEQUENCE: 14
aacaactgct accaatttcc ttg                                             23
```

METHODS OF AFFECTING NITROGEN ASSIMILATION IN PLANTS

This application is a divisional application of U.S. application Ser. No. 12/079,001 filed Mar. 28, 2008, now U.S. Pat. No. 8,153,862 B2, which claims the benefit of U.S. Provisional Application No. 60/919,818 filed Mar. 23, 2007, the disclosure of each of which is incorporated by reference herein in its entirety.

This invention was made with U.S. government support under National Institutes of Health Grant ROI GM032877, Department of Energy Grant DEFG02-92ER20071, National Science Foundation Arabidopsis Grant IOB 0519985 (to G.M.C.), and National Science Foundation Grant MCB-0343887 (to C.R.M.). The U.S. government has certain rights in the invention.

1. INTRODUCTION

Provided herein are compositions and methods for affecting nitrogen assimilation, usage and storage by overexpressing or underexpressing certain genes in plants. Such genes include nitrogen-responsive master regulatory control genes CCA1, GLK1 and bZIP1. In some embodiments, provided herein are compositions and methods for genetically engineering plants to increase CCA1 or GLK1 expression or decrease bZIP1 expression, or any combination thereof. In other embodiments, provided herein are compositions and methods for genetically engineering plants to decrease CCA1 or GLK1 expression or increase bZIP1 expression, or any combination thereof. In certain embodiments, the overexpression or underexpression is in a tissue- or cell-specific manner, e.g., in vegetative tissue or in leaves or in fruit or seeds, or in specific cell types (e.g., mesophyll, phloem, etc. In certain specific embodiments, a plant or tree is genetically engineered to increase or constitutively express CCA1 and GLK1 and to decrease expression of bZIP1 in vegetative (growing) tissues of the plant. Such genetically engineered plants are able to assimilate more nitrogen into Gln, such that more nitrogen is available for biosynthesis, and thereby grow larger, more efficiently or rapidly, and/or have increased biomass. Alternatively, the engineered plants may be used to achieve faster growing or maturing crops or, higher crop yields and/or more nutritious products. In certain embodiments, the engineered plants and methods thereof are used in the production of commercial products. Some non-limiting example include genetically engineered trees for e.g., the production of pulp, paper, paper products or lumber; tobacco, e.g., for the production of cigarettes, cigars, or chewing tobacco; crops, e.g., for the production of fruits, vegetables and other food, including grains, e.g., for the production of wheat, bread, flour, rice, corn; and soybean, canola, e.g., for the production of oils or biofuels. In other specific embodiments, a plant or tree is genetically engineered to increase or constitutively express bZIP1 and to decrease expression of CCA1 and GLK1 in leaves, fruit and/or seed tissues of the plant. This would serve to increase N-assimilation into Asn, an inert N-storage compound used to transport N to seed, for example.

2. BACKGROUND

Nitrate is a key required nutrient for the synthesis of amino acids, nucleotides and vitamins and is commonly considered to be the most limiting for normal plant growth (Vitousek et al., 2004, Biogeochemistry 13). Nitrogenous fertilizer is usually supplied as ammonium nitrate, potassium nitrate, or urea. Plants are keenly sensitive to nitrogen levels in the soil and, atypically of animal development, adopt their body plan to cope with their environment (Lopez-Bucio et al., 2003, Curr Opin Plant Biol 6:280-287; Malamy et al., 2005, Plant Cell Environ 28:67-77; Walch-Liu et al., 2006, Ann Bot (Lond) 97:875-81). For example, mutants in several general nitrogen (N)-assimilation genes affect root architecture (Little et al., 2005, Proc Natl Acad Sci USA 102:13693-13698; Remans et al., 2006, Proc Natl Acad Sci USA 103:19206-19211). Transduction of this nitrogen signal is linked to a massive and concerted gene expression response in the root (Gutierrez et al., 2007, Genome Biol 8:R7; Wang et al., 2003, Plant Physiol 132: 556-67).

Studies on the regulation of genes involved in the N-assimilatory pathway have shown that genes involved in N-assimilation are regulated transcriptionally by both inorganic and organic forms of nitrogen (FIG. 1). Genes involved in the uptake and reduction of nitrate (NIA, NIR) are transcriptionally induced by nitrate. By contrast, the glutamine synthetase gene (GLN1.3) involved in assimilating inorganic N into organic form (Gln), is transcriptionally repressed by the endproducts of N-assimilation (Glu/Gln) (FIG. 1). The repression of GLN1.3 expression by the product of the GS enzyme reaction serves as a negative feedback loop, that shuts off further assimilation of inorganic N into Gln, when levels of Gln are abundant. As GS is and ATP dependent enzyme, this is likely to be an energy conservation mechanism. By contrast, Gln/Glu levels activate the expression of the ASN1 gene (asparagine synthetase) which serves to transfer the amide N from Gln onto Asp to make Asn and Glu as a by-product. Asn is an inert amino acid used to store N and used for long distance N-transport (e.g., to seed). The induction of ASN1 by Glu/Gln is a mechanism that serves to store excess N as Asn, which is used to transport N to seed.

It would be advantageous to produce plants that would continue to assimilate and utilize N or to store N depending on whether a vegetative plant part or seed is the product, respectively, making N-assimilation independent of the Glu/Gln biofeedback pathway. N-assimilated into Glu/Gln by GS is used in the biosynthesis of all N-containing compounds including essentially all other amino acids, nucleic acids and chlorophyll. By contrast, the conversion of Gln to Asn (an inert N source) is used to transport and store N in seed.

3. SUMMARY

Master control genes (CCA1, GLK1, and bZIP1) that control N-assimilation in response to Glu sensing have been identified in the present invention. As these genes are transcription factor hubs, they coordinate the N-regulation of the N-assimilatory gene network, with genome-wide responses associated with growth and development in plants. Thus, effecting genome-wide changes in N-assimilation, plant growth and development, by the transgenic manipulation of these master control genes in plants will effect nitrogen use efficiency in vegetative tissues (leaves & roots) and also in seed. Changes in levels of N-assimilated into Gln effect changes in growth of vegetative tissues, while changes in levels of Asn affect seed development and nitrogen content.

Figure 12:
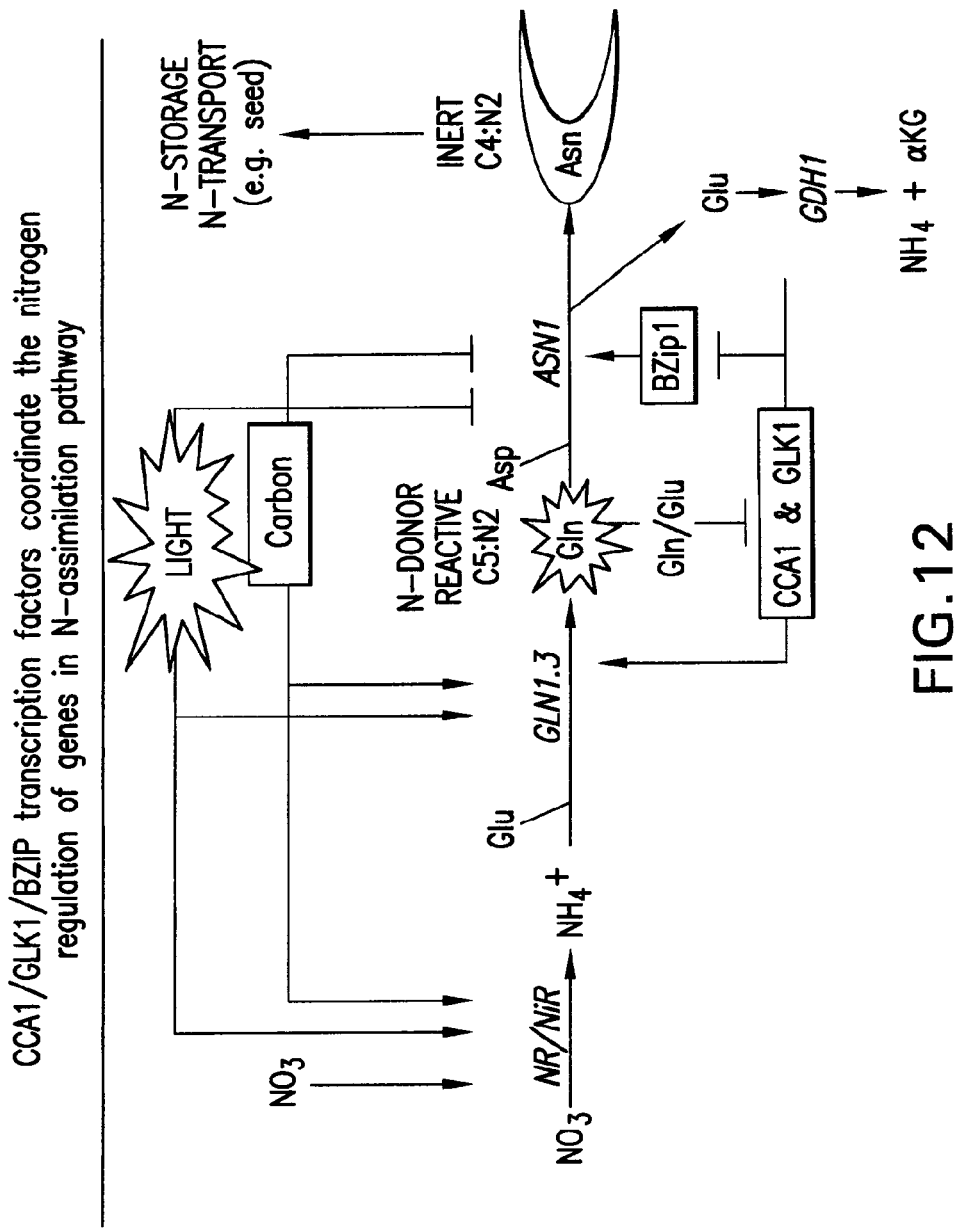

Thus, the present invention relates to the transgenic manipulation of these N-responsive master regulatory genes (CCA1, GLK1, and bZIP1) that control N-assimilation, and other related processes in response to N treatments, so as to increase the overall N-assimilation capacity, whether for increased N usage or N storage. The overexpression of these master control genes (e.g., uncoupled from Glu repression) effectively releases N-assimilation from the feedback repression loop by Glu-leading to increased N-assimilation and usage. As these regulatory genes serve to respond to Glu levels by reciprocally regulating the amount of N-assimilated into Gln versus the amount of Gln metabolized to Asn (for N-storage and transport), the manipulation of these genes in transgenic plants can be used to optimize N-assimilation into Gln versus Asn (FIG. 2, FIG. 12). Increased N-assimilation is advantageous in all crops. Additionally, in seed crops, the increased synthesis of Asn increases N-transported and stored in seed. The genes, CCA1, GLK1 and/or bZIP1, can be expressed using constitutive promoters. Alternately, developmentally regulated promoters can be used to over express CCA1 and/or GLK1 that favors Gln production early in the life cycle, while switching to overexpressing bZIP1 which favors Asn production later in the life cycle (e.g., during seed set). Further, underexpressing CCA1 and/or GLK1 favors Asn production and underexpressing bZIP1 favors Gln production.

As CCA1/GLK1 and bZIP1 are master regulatory genes controlling genes in the N-assimilatory pathway as well as other processes, the manipulation of these genes in transgenic plants can coordinate an increase in N-assimilation and usage (increased Gln synthesis), and/or an increase in stored N (increased Asn synthesis) with genes controlling aspects of growth and development, that are also targets for these master regulatory genes.

Thus, in one embodiment, the present invention is directed to a method for improving nitrogen assimilation and usage in a plant in which more nitrogen is available for biosynthesis, said method comprising overexpressing GLK1 in the plant. In another embodiment, the present invention is directed to a method for improving nitrogen assimilation and usage in a plant in which more nitrogen is available for biosynthesis, said method comprising overexpressing CCA1 in the plant. In yet another embodiment, the present invention is directed to a method for improving nitrogen assimilation and usage in a plant in which more nitrogen is available for biosynthesis, said method comprising underexpressing bZIP1 in the plant.

In another embodiment, the method for improving nitrogen assimilation and usage in a plant in which more nitrogen is available for biosynthesis comprises overexpressing CCA1 and GLK1 in the plant. In another embodiment, the method for improving nitrogen assimilation and usage in a plant in which more nitrogen is available for biosynthesis comprises overexpressing CCA1 and underexpressing bZIP1 in the plant, or overexpressing GLK1 and underexpressing bZIP1 in the plant. In yet another embodiment, the method for improving nitrogen assimilation and usage in a plant in which more nitrogen is available for biosynthesis comprises overexpressing CCA1, overexpressing GLK1 and underexpressing bZIP1 in the plant.

The present invention is also directed to methods for altering nitrogen assimilation and storage, e.g., increasing nitrogen storage, in a plant. In one embodiment, the method comprises overexpressing bZIP1 in the plant. In another embodiment, the method comprises underexpressing CCA1 in the plant and/or underexpressing GLK1 in the plant. In another embodiment, the method overexpressing bZIP1 and underexpressing CCA1 and/or GLK1 in the plant. In yet another embodiment, the method comprises overexpressing bZIP1, and underexpressing CCA1 and underexpressing GLK1 in the plant.

In certain embodiments, the plant is species of woody, ornamental, decorative, crop, cereal, fruit, or vegetable. In other embodiments, the plant is a species of one of the following genuses: *Acorus, Aegilops, Allium, Amborella, Antirrhinum, Apium, Arabidopsis, Arachis, Beta, Betula, Brassica, Capsicum, Ceratopteris, Citrus, Cryptomeria, Cycas, Descurainia, Eschscholzia, Eucalyptus, Glycine, Gossypium, Hedyotis, Helianthus, Hordeum, Ipomoea, Lactuca, Linum, Liriodendron, Lotus, Lupinus, Lycopersicon, Medicago, Mesembryanthemum, Nicotiana, Nuphar, Pennisetum, Persea, Phaseolus, Physcomitrella, Picea, Pinus, Poncirus, Populus, Prunus, Robinia, Rosa, Saccharum, Schedonorus, Secale, Sesamum, Solanum, Sorghum, Stevia, Thellungiella, Theobroma, Triphysaria, Triticum, Vitis, Zea*, or *Zinnia*.

The overexpression of a particular gene can be accomplished by any method known in the art, for example, by transforming a plant cell with a nucleic acid vector comprising the coding sequences of the desired gene operably linked to a promoter active in a plant cell such that the desired gene is expressed at levels higher than normal, i.e., levels found in a control/nontransgenic plant. Such promoters can be constitutively active in all or some plant tissues or can be inducible.

The underexpression of a desired gene can be accomplished by any method known in the art, such as knocking out the gene or mutating the gene transgenically such that lower than normal levels of the gene product is produced in the transgenic cells or plant. For example, such mutations include frame-shift mutations or mutations resulting in a stop codon in the wild-type coding sequence, thus preventing expression of the gene product. Another exemplary mutation would be the removal of the transcribed sequences from the plant genome, for example, by homologous recombination. Another method for underexpressing a gene is transgenically introducing an insertion or deletion into the transcribed sequence or an insertion or deletion upstream or downstream of the transcribed sequence such that expression of the gene product is decreased as compared to wild-type or appropriate control. Additionally, microRNA can be used to target a particular encoding mRNA for degradation, thus reducing the level of the expressed gene product in the transgenic plant cell.

The present invention is also directed to a transgenic plant produced by any of the foregoing methods.

The present invention is also directed to compositions for modulating gene expression in plants. The compositions comprise constructs for the expression of CCA1, GLK1 or bZIP1. In certain embodiments, a construct of the invention comprises a promoter, such as a tissue specific promoter, which is expressed in a plant cell, such as a leaf cell, and promotes the expression of CCA1, GLK1 or bZIP1.

Any of a variety of promoters can be utilized in the constructs of the invention depending on the desired outcome. Tissue-specific or tissue-preferred promoters, inducible promoters, developmental promoters, constitutive promoters and/or chimeric promoters can be used to direct expression of the gene product in specific cells or organs the plant, when fused to the appropriate cell or organ specific promoter.

Chimeric constructs expressing CCA1, GLK1 or bZIP1 in transgenic plants (using constitutive or inducible promoters) can be used in the compositions and methods provided herein to enhance nitrogen assimilation and usage or increase nitrogen storage.

The present invention is also directed to a transgenic plant-derived commercial product. In one embodiment, the transgenic plant is a tree, and said commercial product is pulp, paper, a paper product, or lumber. In another embodiment, the transgenic plant is tobacco, and said commercial product is a cigarette, cigar, or chewing tobacco. In yet another embodiment, the transgenic plant is a crop, and said commercial product is a fruit or vegetable. In yet another embodiment, the transgenic plant is a grain, and said commercial product is bread, flour, cereal, oat meal, or rice. In another embodiment, the product is a biofuel or a plant oil.

4. TERMINOLOGY

Units, prefixes, and symbols may be denoted in their SI accepted form. Unless otherwise indicated, nucleic acids are written left to right in 5' to 3' orientation; amino acid sequences are written left to right in amino to carboxyl orientation, respectively. Numeric ranges recited within the specification are inclusive of the numbers defining the range and include each integer within the defined range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5th edition, 1993). The terms defined below are more fully defined by reference to the specification as a whole.

As used herein, the term "agronomic" includes, but is not limited to, changes in root size, vegetative yield, seed yield or overall plant growth. Other agronomic properties include factors desirable to agricultural production and business.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., Diagnostic Molecular Microbiology: Principles and Applications, D. H. Persing et al., Ed., 1993, American Society for Microbiology, Washington, D.C. The product of amplification is termed an amplicon.

As used herein, "antisense orientation" includes reference to a duplex polynucleotide sequence that is operably linked to a promoter in an orientation where the antisense strand is transcribed. The antisense strand is sufficiently complementary to an endogenous transcription product such that translation of the endogenous transcription product is often inhibited.

In its broadest sense, a "delivery system," as used herein, is any vehicle capable of facilitating delivery of a nucleic acid (or nucleic acid complex) to a cell and/or uptake of the nucleic acid by the cell.

The term "ectopic" is used herein to mean abnormal subcellular (e.g., switch between organellar and cytosolic localization), cell-type, tissue-type and/or developmental or temporal expression (e.g., light/dark) patterns for the particular gene or enzyme in question. Such ectopic expression does not necessarily exclude expression in tissues or developmental stages normal for said enzyme but rather entails expression in tissues or developmental stages not normal for the said enzyme.

By "endogenous nucleic acid sequence" and similar terms, it is intended that the sequences are natively present in the recipient plant genome and not substantially modified from its original form.

The term "exogenous nucleic acid sequence" as used herein refers to a nucleic acid foreign to the recipient plant host or, native to the host if the native nucleic acid is substantially modified from its original form. For example, the term includes a nucleic acid originating in the host species, where such sequence is operably linked to a promoter that differs from the natural or wild-type promoter.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate Macronucleus, may be used when the nucleic acid is expressed therein.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al., 1989, Nucl. Acids Res. 17: 477-498). Thus, the maize preferred codon for a particular amino acid may be derived from known gene sequences from maize. Maize codon usage for 28 genes from maize plants is listed in Table 4 of Murray et al., supra.

By "fragment" is intended a portion of the nucleotide sequence. Fragments of the modulator sequence will generally retain the biological activity of the native suppressor protein. Alternatively, fragments of the targeting sequence may or may not retain biological activity. Such targeting sequences may be useful as hybridization probes, as antisense constructs, or as co-suppression sequences. Thus, fragments of a nucleotide sequence may range from at least about 20 nucleotides, about 50 nucleotides, about 100 nucleotides, and up to the full-length nucleotide sequence of the invention.

As used herein "full-length sequence" in reference to a specified polynucleotide or its encoded protein means having the entire amino acid sequence of, a native (non-synthetic), endogenous, biologically active form of the specified protein. Methods to determine whether a sequence is full-length are well known in the art including such exemplary techniques as northern or western blots, primer extension, S1 protection, and ribonuclease protection. See, e.g., Plant Molecular Biology: A Laboratory Manual, Clark, Ed., 1997, Springer-Verlag, Berlin. Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNN-NAUGG, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

The term "gene activity" refers to one or more steps involved in gene expression, including transcription, translation, and the functioning of the protein encoded by the gene.

The term "genetic modification" as used herein refers to the introduction of one or more exogenous nucleic acid sequences, e.g., CCA1, GLK1 or bZIP1 encoding sequences, as well as regulatory sequences, into one or more plant cells, which in certain cases can generate whole, sexually competent, viable plants. The term "genetically modified" or "genetically engineered" as used herein refers to a plant which has been generated through the aforementioned process. Genetically modified plants of the invention are capable of self-pollinating or cross-pollinating with other plants of the same species so that the foreign gene, carried in the germ line, can be inserted into or bred into agriculturally useful plant varieties.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell that contains a vector and supports the replication and/or expression of the vector. Host cells may be prokaryotic cells such as *E. coli*, or eukaryotic cells such as yeast, plant, insect, amphibian, or mammalian cells. Preferably, host cells are monocotyledonous or dicotyledonous plant cells. A particularly preferred monocotyledonous host cell is a maize host cell.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The term "isolated" refers to material, such as a nucleic acid or a protein, which is: (1) substantially or essentially free from components which normally accompany or interact with it as found in its natural environment. The isolated material optionally comprises material not found with the material in its natural environment; or (2) if the material is in its natural environment, the material has been synthetically altered or synthetically produced by deliberate human intervention and/or placed at a different location within the cell. The synthetic alteration or creation of the material can be performed on the material within or apart from its natural state. For example, a naturally-occurring nucleic acid becomes an isolated nucleic acid if it is altered or produced by non-natural, synthetic methods, or if it is transcribed from DNA which has been altered or produced by non-natural, synthetic methods. See, e.g., Compounds and Methods for Site Directed Mutagenesis in Eukaryotic Cells, Kmiec, U.S. Pat. No. 5,565,350; In vivo Homologous Sequence Targeting in Eukaryotic Cells; Zarling et al., PCT/US93/03868.

The isolated nucleic acid may also be produced by the synthetic re-arrangement ("shuffling") of a part or parts of one or more allelic forms of the gene of interest. Likewise, a naturally-occurring nucleic acid (e.g., a promoter) becomes isolated if it is introduced to a different locus of the genome. Nucleic acids which are "isolated," as defined herein, are also referred to as "heterologous" nucleic acids.

As used herein, the term "marker" refers to a gene encoding a trait or a phenotype which permits the selection of, or the screening for, a plant or plant cell containing the marker.

As used herein, "nucleic acid" includes reference to a deoxyribonucleotide or ribonucleotide polymer, or chimeras thereof, in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules which comprise and substantially represent the entire transcribed fraction of a genome of a specified organism or of a tissue from that organism. Construction of exemplary nucleic acid libraries, such as genomic and cDNA libraries, is taught in standard molecular biology references such as Berger and Kimmel, Guide to Molecular Cloning Techniques, Methods in Enzymology, Vol. 152, Academic Press, Inc., San Diego, Calif. (Berger); Sambrook et al., 1989, Molecular Cloning—A Laboratory Manual, 2nd ed., Vol. 1-3; and Current Protocols in Molecular Biology, F. M. Ausubel et al., Eds., 1994, Current Protocols, a joint venture between Greene Publishing Associates, Inc. and John Wiley & Sons, Inc.

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

The term "orthologous" as used herein describes a relationship between two or more polynucleotides or proteins. Two polynucleotides or proteins are "orthologous" to one another if they are derived from a common ancestral gene and serve a similar function in different organisms. In general, orthologous polynucleotides or proteins will have similar catalytic functions (when they encode enzymes) or will serve similar structural functions (when they encode proteins or RNA that form part of the ultrastructure of a cell).

The term "overexpression" is used herein to mean above the normal expression level in the particular tissue, all and/or developmental or temporal stage for said enzyme/expressed protein product.

As used herein, the term "plant" is used in its broadest sense, including, but is not limited to, any species of woody, ornamental or decorative, crop or cereal, fruit or vegetable plant, and algae (e.g., *Chlamydomonas reinhardtii*). Non-limiting examples of plants include plants from the genus *Arabidopsis* or the genus *Oryza*. Other examples include plants from the genuses *Acorus, Aegilops, Album, Amborella, Antirrhinum, Apium, Arachis, Beta, Betula, Brassica, Capsicum, Ceratopteris, Citrus, Cryptomeria, Cycas, Descurainia, Eschscholzia, Eucalyptus, Glycine, Gossypium, Hedyotis, Helianthus, Hordeum, Ipomoea, Lactuca, Linum, Liriodendron, Lotus, Lupinus, Lycopersicon, Medicago, Mesembryanthemum, Nicotiana, Nuphar, Pennisetum, Per-* sea, *Phaseolus, Physcomitrella, Picea, Pinus, Poncirus, Populus, Prunus, Robinia, Rosa, Saccharum, Schedonorus, Secale, Sesamum, Solanum, Sorghum, Stevia, Thellungiella, Theobroma, Triphysaria, Triticum, Vitis, Zea,* or *Zinnia.*" Plants included in the invention are any plants amenable to transformation techniques, including gymnosperms and angiosperms, both monocotyledons and dicotyledons. Examples of monocotyledonous angiosperms include, but are not limited to, asparagus, field and sweet corn, barley, wheat, rice, sorghum, onion, pearl millet, rye and oats and other cereal grains. Examples of dicotyledonous angiosperms include, but are not limited to tomato, tobacco, cotton, rapeseed, field beans, soybeans, peppers, lettuce, peas, alfalfa, clover, cole crops or *Brassica oleracea* (e.g., cabbage, broccoli, cauliflower, brussel sprouts), radish, carrot, beets, eggplant, spinach, cucumber, squash, melons, cantaloupe, sunflowers and various ornamentals. Examples of woody species include poplar, pine, *sequoia*, cedar, oak, etc. Still other examples of plants include, but are not limited to, wheat, cauliflower, tomato, tobacco, corn, petunia, trees, etc. As used herein, the term "cereal crop" is used in its broadest sense. The term includes, but is not limited to, any species of grass, or grain plant (e.g., barley, corn, oats, rice, wild rice, rye, wheat, millet, sorghum, triticale, etc.), non-grass plants (e.g., buckwheat flax, legumes or soybeans, etc.). As used herein, the term "crop" or "crop plant" is used in its broadest sense. The term includes, but is not limited to, any species of plant or algae edible by humans or used as a feed for animals or used, or consumed by humans, or any plant or algae used in industry or commerce. As used herein, the term "plant" also refers to either a whole plant, a plant part, or organs (e.g., leaves, stems, roots, etc.), a plant cell, or a group of plant cells, such as plant tissue, plant seeds and progeny of same. Plantlets are also included within the meaning of "plant." The class of plants which can be used in the methods of the invention is generally as broad as the class of higher plants amenable to transformation techniques, including both monocotyledonous and dicotyledonous plants.

The term "plant cell" as used herein refers to protoplasts, gamete producing cells, and cells which regenerate into whole plants. Plant cell, as used herein, further includes, without limitation, cells obtained from or found in: seeds, suspension cultures, embryos, meristematic regions, callus tissue, leaves, roots, shoots, gametophytes, sporophytes, pollen, and microspores. Plant cells can also be understood to include modified cells, such as protoplasts, obtained from the aforementioned tissues.

As used herein, "polynucleotide" includes reference to a deoxyribopolynucleotide, ribopolynucleotide, or chimeras or analogs thereof that have the essential nature of a natural deoxy- or ribo-nucleotide in that they hybridize, under stringent hybridization conditions, to substantially the same nucleotide sequence as naturally occurring nucleotides and/ or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically-, enzymatically- or metabolically-modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally-occurring amino acid, as well as to naturally-occurring amino acid polymers. The essential nature of such analogues of naturally-occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. Further, this invention contemplates the use of both the methionine-containing and the methionine-less amino terminal variants of the protein of the invention.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells whether or not its origin is a plant cell. Exemplary plant promoters include, but are not limited to, those that are obtained from plants, plant viruses, and bacteria which comprise genes expressed in plant cells such *Agrobacterium* or *Rhizobium*. Examples of promoters under developmental control include promoters that preferentially initiate transcription in certain tissues, such as leaves, roots, or seeds. Such promoters are referred to as "tissue preferred." Promoters which initiate transcription only in certain tissue are referred to as "tissue specific." A "cell type" specific promoter primarily drives expression in certain cell types in one or more organs, for example, vascular cells in roots or leaves. An "inducible" or "repressible" promoter is a promoter which is under environmental control. Examples of environmental conditions that may effect transcription by inducible promoters include anaerobic conditions or the presence of light. Tissue specific, tissue preferred, cell type specific, and inducible promoters represent the class of "non-constitutive" promoters. A "constitutive" promoter is a promoter which is active under most environmental conditions.

As used herein "recombinant" includes reference to a cell or vector that has been modified by the introduction of a heterologous nucleic acid, or to a cell derived from a cell so modified. Thus, for example, recombinant cells express genes that are not found in identical form within the native (non-recombinant) form of the cell, or exhibit altered expression of native genes, as a result of deliberate human intervention. The term "recombinant" as used herein does not encompass the alteration of the cell or vector by events (e.g., spontaneous mutation, natural transformation, transduction, or transposition) occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "regulatory sequence" as used herein refers to a nucleic acid sequence capable of controlling the transcription of an operably associated gene. Therefore, placing a gene under the regulatory control of a promoter or a regulatory element means positioning the gene such that the expression of the gene is controlled by the regulatory sequence(s). Because a microRNA binds to its target, it is a post transcriptional mechanism for regulating levels of mRNA. Thus, an miRNA can also be considered a "regulatory sequence" herein. Not just transcription factors.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "tissue-specific promotor" is a polynucleotide sequence that specifically binds to transcription factors expressed primarily or only in such specific tissue.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

As used herein, a "stem-loop motif" or a "stem-loop structure," sometimes also referred to as a "hairpin structure," is given its ordinary meaning in the art, i.e., in reference to a single nucleic acid molecule having a secondary structure that includes a double-stranded region (a "stem" portion) composed of two regions of nucleotides (of the same molecule) forming either side of the double-stranded portion, and at least one "loop" region, comprising uncomplemented nucleotides (i.e., a single-stranded region).

The term "stringent conditions" or "stringent hybridization conditions" includes reference to conditions under which a probe will selectively hybridize to its target sequence, to a detectably greater degree than to other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1× SSC at 55 to 60° C. Exemplary high stringency conditions include hybridization in 50% formamide, 1 M NaCl, 1% SDS at 37° C., and a wash in 0.1× SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, 1984, Anal. Biochem., 138:267-284: $T_m=81.5°$ C.$+16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York; and Current Protocols in Molecular Biology, Chapter 2, Ausubel et al., Eds., 1995, Greene Publishing and Wiley-Interscience, New York. Hybridization and/or wash conditions can be applied for at least 10, 30, 60, 90, 120, or 240 minutes.

As used herein, "transcription factor" includes reference to a protein which interacts with a DNA regulatory element to affect expression of a structural gene or expression of a second regulatory gene. "Transcription factor" may also refer to the DNA encoding said transcription factor protein. The function of a transcription factor may include activation or repression of transcription initiation.

The term "transfection," as used herein, refers to the introduction of a nucleic acid into a cell, for example, a nucleotide sequence able to be transcribed to produce CCA1, GLK1 or BZIP1 protein.

As used herein, the term "transformation" means alteration of the genotype of a host plant by the introduction of a CCA1, GLK1 or BZIP1 nucleic acid sequence.

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

The term "underexpression" is used herein to mean below the normal expression level in the particular tissue, all and/or developmental or temporal stage for said enzyme/expressed protein product.

As used herein, "vector" includes reference to a nucleic acid used in introduction of a polynucleotide of the present invention into a host cell. Vectors are often replicons. Expression vectors permit transcription of a nucleic acid inserted therein.

The following terms are used to describe the sequence relationships between a polynucleotide/polypeptide of the present invention with a reference polynucleotide/polypeptide: (a) "reference sequence", (b) "comparison window", (c) "sequence identity", and (d) "percentage of sequence identity".

(a) As used herein, "reference sequence" is a defined sequence used as a basis for sequence comparison with a polynucleotide/polypeptide of the present invention. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide/polypeptide sequence, wherein the polynucleotide/polypeptide sequence may be compared to a reference sequence and wherein the portion of the polynucleotide/polypeptide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides/amino acids residues in length, and optionally can be 30, 40, 50, 100, or longer. Those of skill in the art understand that to avoid a high similarity to a reference sequence due to inclusion of gaps in the polynucleotide/polypeptide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, 1981, Adv. Appl. Math. 2: 482; by the homology alignment algorithm of Needleman and Wunsch, 1970, J. Mol. Biol. 48: 443; by the search for similarity method of Pearson and Lipman, 1988, Proc. Natl. Acad. Sci. 85: 2444; by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, 1988, Gene 73: 237-244; Higgins and Sharp, 1989, CABIOS 5: 151-153; Corpet et al., 1988, Nucleic Acids Research 16: 10881-90; Huang et al., 1992, Computer Applications in the Biosciences 8: 155-65; and Pearson et al., 1994, Methods in Molecular Biology 24: 307-331.

The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel et al., Eds., 1995, Greene Publishing and Wiley-Interscience, New York.

Software for performing BLAST analyses is publicly available, e.g., through the National Center for Biotechnology Information (world-wide web at ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, 1989, Proc. Natl. Acad. Sci. USA 89:10915).

In addition to calculating percent sequence identity, the BLAST algorithm also performs a statistical analysis of the similarity between two sequences (see, e.g., Karlin & Altschul, 1993, Proc. Natl. Acad. Sci. USA 90:5873-5877). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, 1993, Comput. Chem., 17:149-163) and XNU (Claverie and States, 1993, Comput. Chem., 17:191-201) low-complexity filters can be employed alone or in combination.

Unless otherwise stated, nucleotide and protein identity/similarity values provided herein are calculated using GAP (GCG Version 10) under default values.

GAP (Global Alignment Program) can also be used to compare a polynucleotide or polypeptide of the present invention with a reference sequence. GAP uses the algorithm of Needleman and Wunsch (J. Mol. Biol. 48: 443-453, 1970) to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 100. Thus, for example, the gap creation and gap extension penalties can each independently be: 0, 1, 2, 3, 4, 5, 6, 7, 8, 9, 10, 15, 20, 30, 40, 50, 60 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff & Henikoff, 1989, Proc. Natl. Acad. Sci. USA 89:10915).

Multiple alignment of the sequences can be performed using the CLUSTAL method of alignment (Higgins and Sharp, 1989, CABIOS. 5:151-153) with the default parameters (GAP PENALTY=10, GAP LENGTH PENALTY=10). Default parameters for pairwise alignments using the CLUSTAL method are KTUPLE 1, GAP PENALTY=3, WINDOW=5 and DIAGONALS SAVED=5.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, 1988, Computer Applic. Biol. Sci., 4:11-17, e.g., as implemented in the program PC/GENE (Intelligenetics, Mountain View, Calif., USA).

Polynucleotide sequences having "substantial identity" are those sequences having at least about 50%, 60% sequence identity, generally 70% sequence identity, preferably at least 80%, more preferably at least 90%, and most preferably at least 95%, compared to a reference sequence using one of the alignment programs described above. Preferably sequence identity is determined using the default parameters determined by the program. Substantial identity of amino acid sequences generally means sequence identity of at least 50%, more preferably at least 70%, 80%, 90%, and most preferably at least 95%. Nucleotide sequences are generally substantially identical if the two molecules hybridize to each other under stringent conditions.

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

As used herein, the term "transgenic," when used in reference to a plant (i.e., a "transgenic plant") refers to a plant that contains at least one heterologous gene in one or more of its cells.

As used herein, "substantially complementary," in reference to nucleic acids, refers to sequences of nucleotides (which may be on the same nucleic acid molecule or on different molecules) that are sufficiently complementary to be able to interact with each other in a predictable fashion, for example, producing a generally predictable secondary structure, such as a stem-loop motif. In some cases, two sequences of nucleotides that are substantially complementary may be at least about 75% complementary to each other, and in some cases, are at least about 80%, at least about 85%, at least about 90%, at least about 95%, at least about 96%, at least about 97%, at least about 98%, at least about 99%, at least about 99.5%, or 100% complementary to each other. In some cases, two molecules that are sufficiently complementary may have a maximum of 40 mismatches (e.g., where one base of the nucleic acid sequence does not have a complementary partner on the other nucleic acid sequence, for example, due to additions, deletions, substitutions, bulges, etc.), and in other cases, the two molecules may have a maximum of 30 mismatches, 20 mismatches, 10 mismatches, or 7 mismatches. In still other cases, the two sufficiently complementary nucleic acid sequences may have a maximum of 0, 1, 2, 3, 4, 5, or 6 mismatches.

By "variants" is intended substantially similar sequences. For "variant" nucleotide sequences, conservative variants include those sequences that, because of the degeneracy of the genetic code, encode the amino acid sequence of the modulator of the invention. Variant nucleotide sequences include synthetically derived sequences, such as those generated, for example, using site-directed mutagenesis. Generally, variants of a particular nucleotide sequence of the invention will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters. By "variant" protein is intended a protein derived from the native protein by deletion or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or human manipulation. Conservative amino acid substitutions will generally result in variants that retain biological function As used herein, the term "yield" or "plant yield" refers to increased plant growth, and/or increased biomass. In one embodiment, increased yield results from increased growth rate and increased root size. In another embodiment, increased yield is derived from shoot growth. In still another embodiment, increased yield is derived from fruit growth.

5. DESCRIPTION OF THE FIGURES

FIG. 1. Schematic diagram of the nitrogen assimilation pathway.

FIG. 2. Schematic diagram of the effects of transgenic overexpression or underexpression of master regulators CCA1/GLK1/bZIP1 on nitrogen assimilation, usage and storage.

Figure 3:
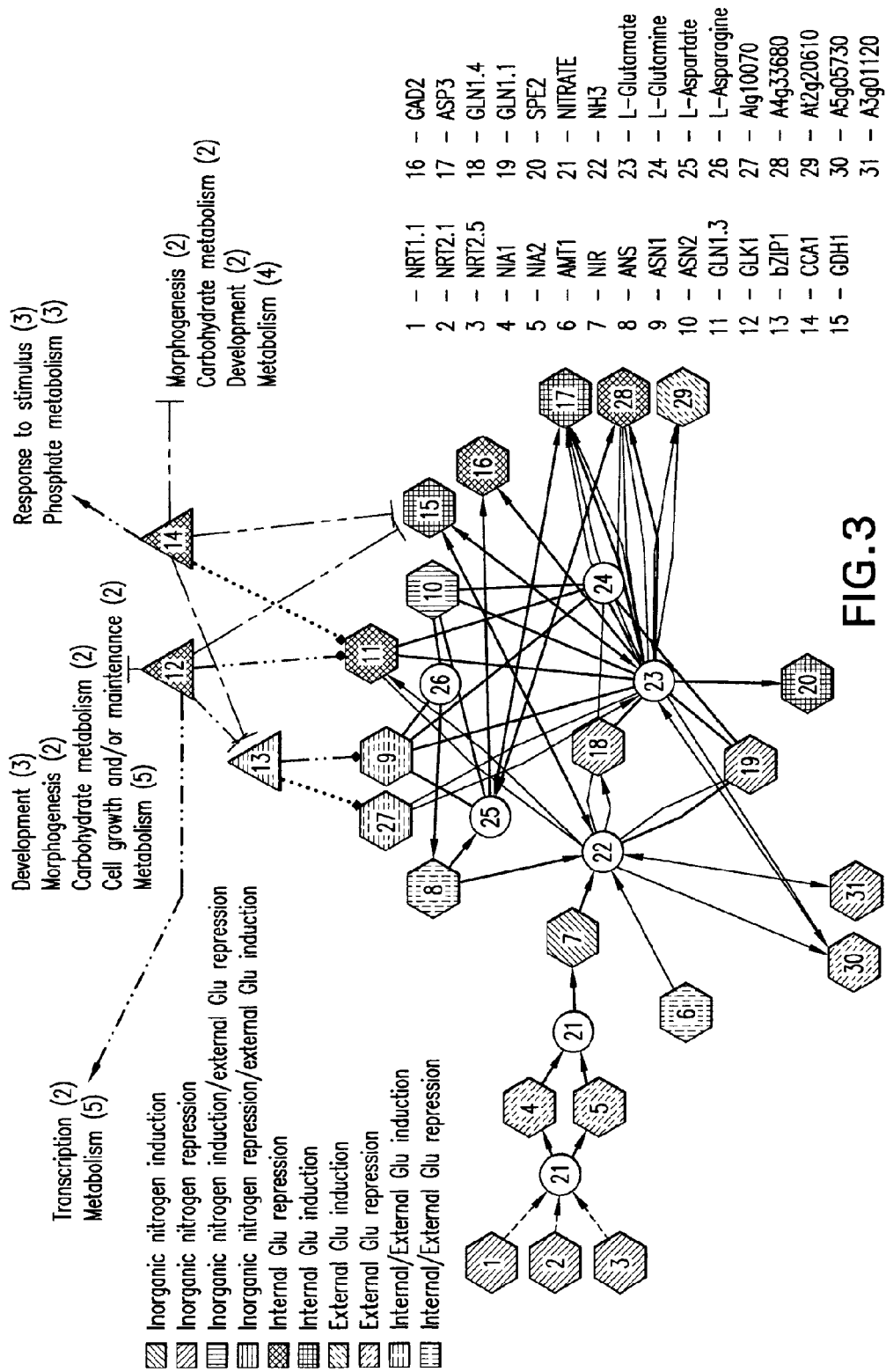

FIG. 3. Network analysis of genes regulated by organic N suggests CCA1 control N-assimilation in plants. In this Cytoscape-generated network, metabolic genes are drawn as triangles (transcription factors), hexagons (metabolic genes) whereas metabolites are shown as white circles. Arrows, diamonds or lines at the end of an edge indicate directionality of the interaction. To simplify, some of the genes connecting to GLK1 and CCA1 are grouped and summarized based on their associated functions (number in parenthesis indicate the number of genes in the group).

Figure 4A:
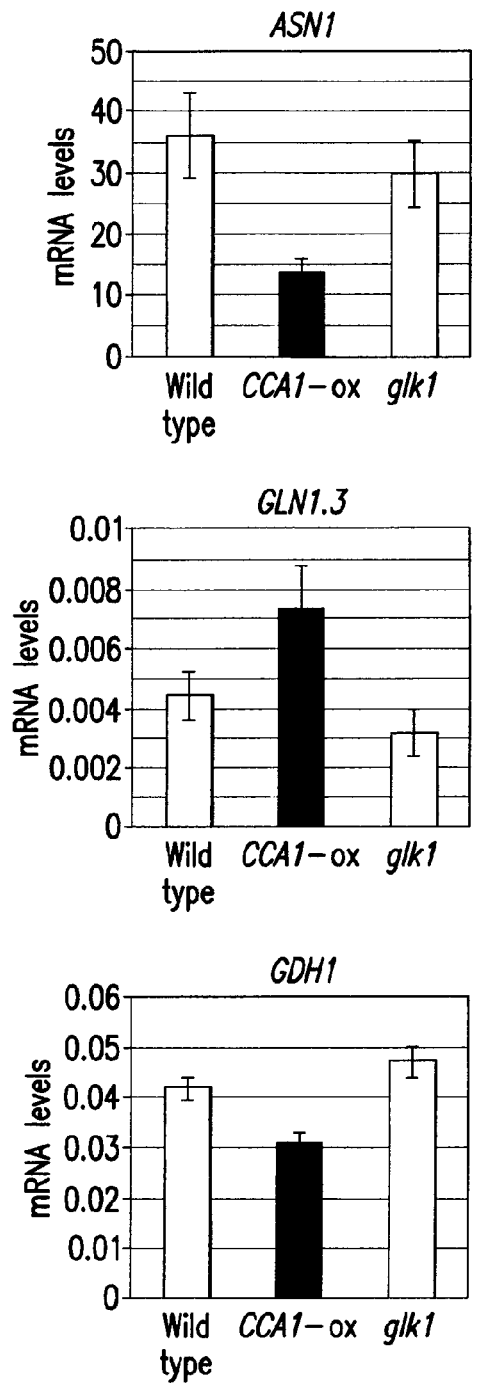
Figure 4B:
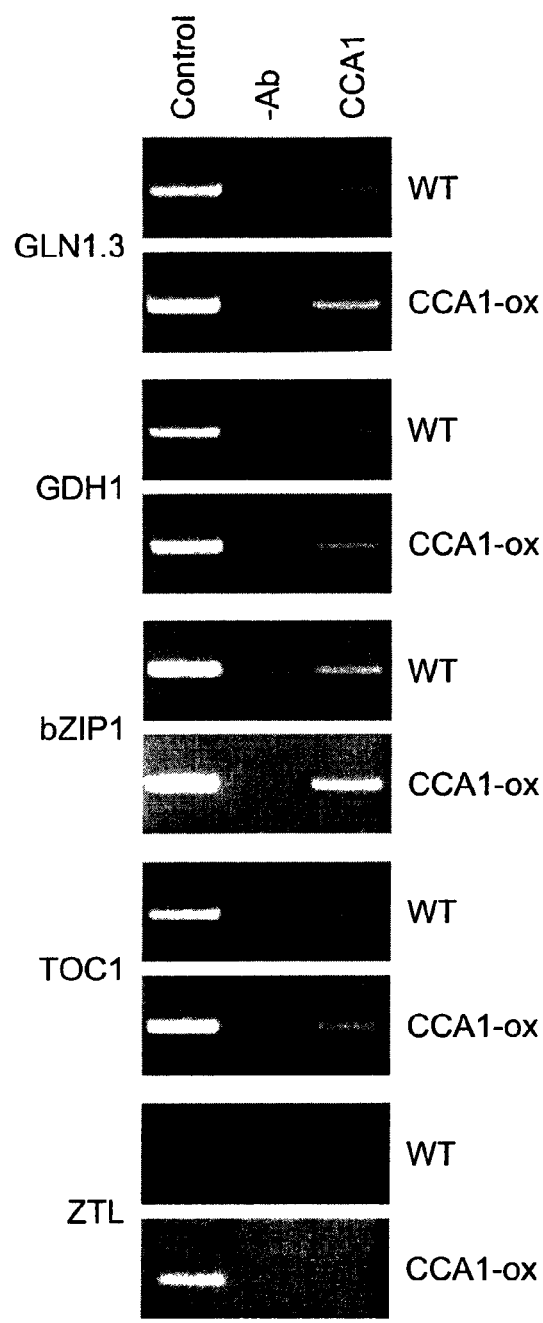
Figure 5A:
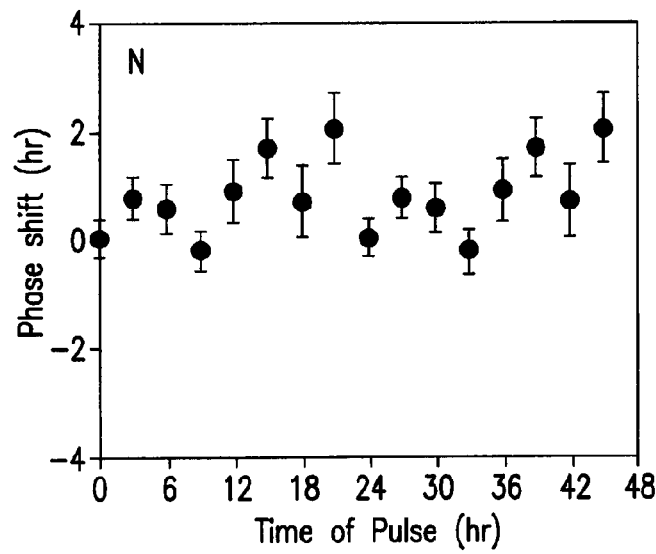
Figure 5B:
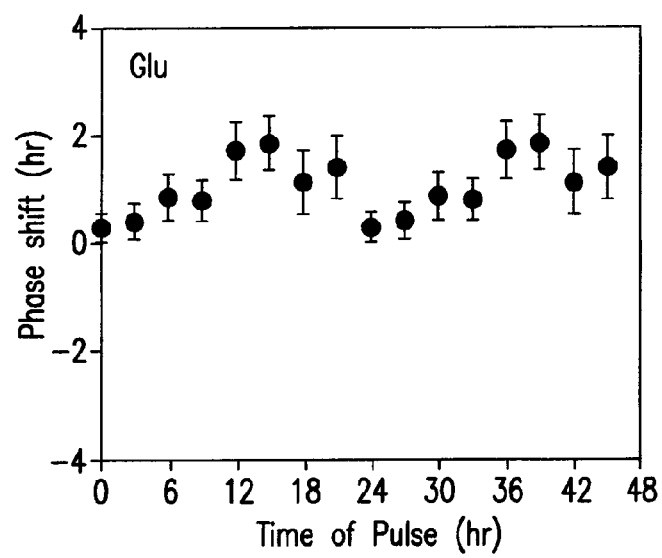
Figure 5C:
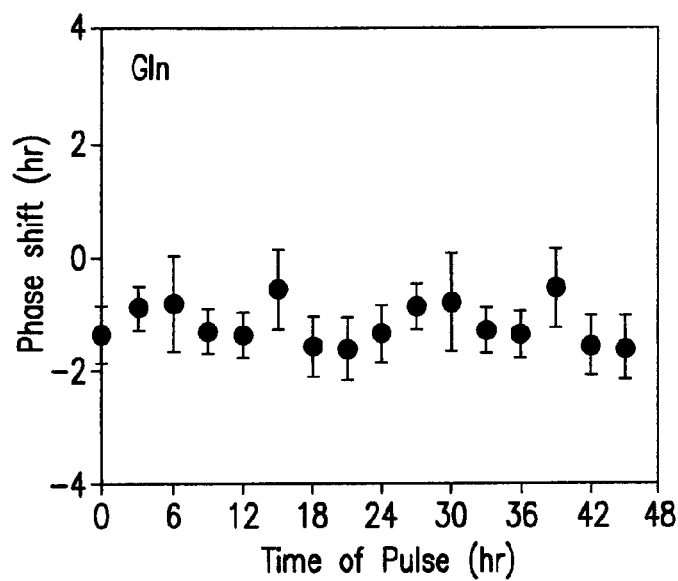
Figure 5D:
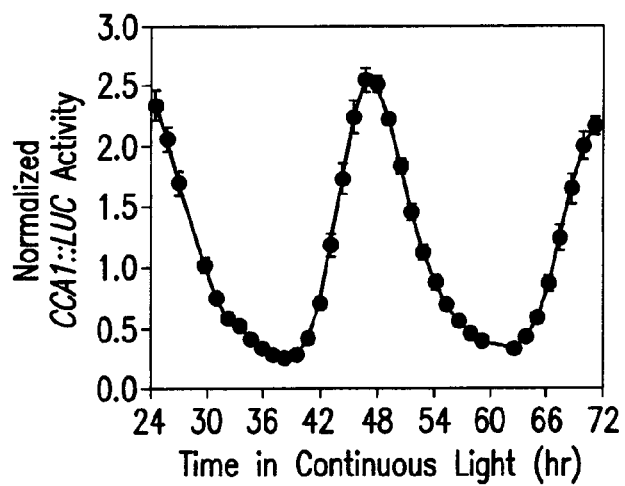

FIG. 4. Altered mRNA levels of target genes and binding of CCA1 protein to target gene promoter regions validate predicted regulation by CCA1. FIG. 4A: RT-qPCR was performed on CCA1-ox, glk1 knockout, and wild-type plants to determine mRNA levels for ASN1, GLN1.3, and GDH1. Three biological and two technical replicates were carried out for each sample. mRNA levels were normalized to clathrin (At4g24550). The mean+/−standard error of the mean is shown. FIG. 4B: ChIP assays to show binding of CCA1 to GLN1.3, GDH1 and bZIP1 gene promoter regions. Control: input DNA control (no IP), −Ab: IP without antibody, CCA1: IP with the CCA1 antibody.

FIG. 5. Exposure of seedlings to pulses of inorganic and organic N shifts the phase of the circadian clock. FIGS. 5A-C: Plot of the phase shift of CCA1::LUC expression in response to 4-h pulse of inorganic N (20 mM $KNO_3$/20 mM $NH_4NO_3$), 10 mM Glu, or 10 mM Gln against the time at which the pulse was administered to wild-type seedlings. Pulses were administered at 3-hr intervals spanning one complete circadian cycle and data were collected over the next 6 cycles. Phase shifts are double-plotted to emphasize the circadian pattern of the response. Phase advances (the peak in expression occurring earlier) are plotted as positive values and delays are plotted as negative values. FIG. 5D shows the CCA1::LUC expression of control (untreated) seedlings. In all panels, the entraining photocycle (16:8) is indicated by the vertical white (light) and gray (dark) bars. The mean+/−standard error of the mean is shown.

Figure 6:
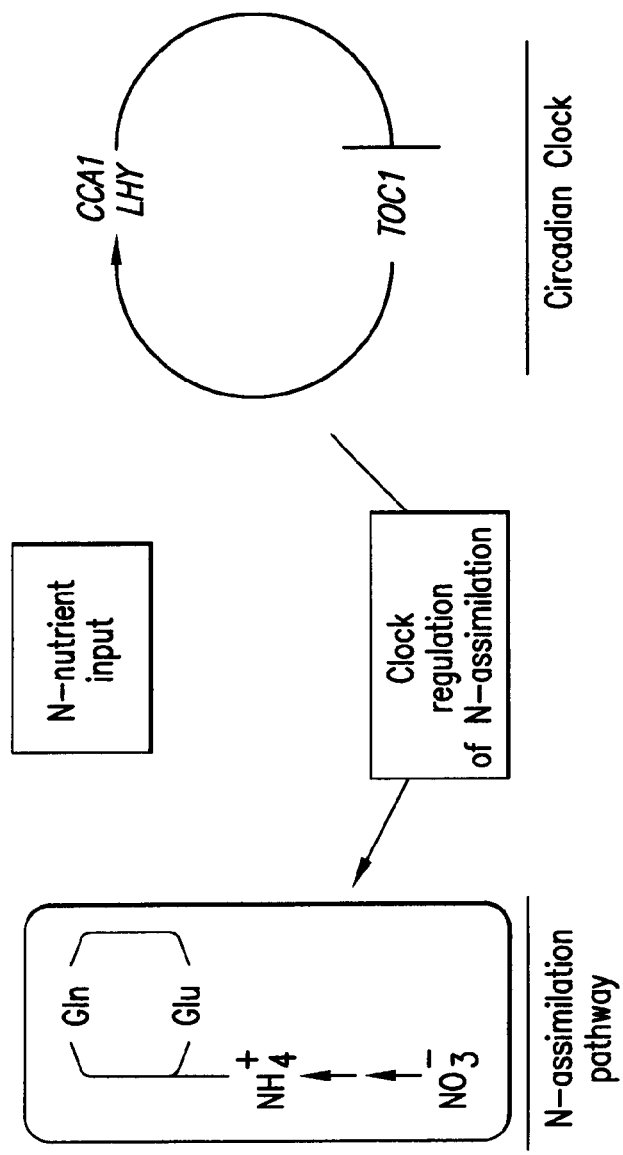

FIG. 6. Proposed model of the interaction between the Arabidopsis circadian clock and N-assimilatory pathway. Arrows indicate influences that affect the function of the two processes. Black arrow: Clock function would affect N-assimilation. This influence is at least partly due to the direct regulatory role of CCA1 on N-assimilation. Grey arrow: N-assimilation would influence clock function through downstream metabolites such as Glu, Gln and possibly other N-metabolites.

Figure 7:
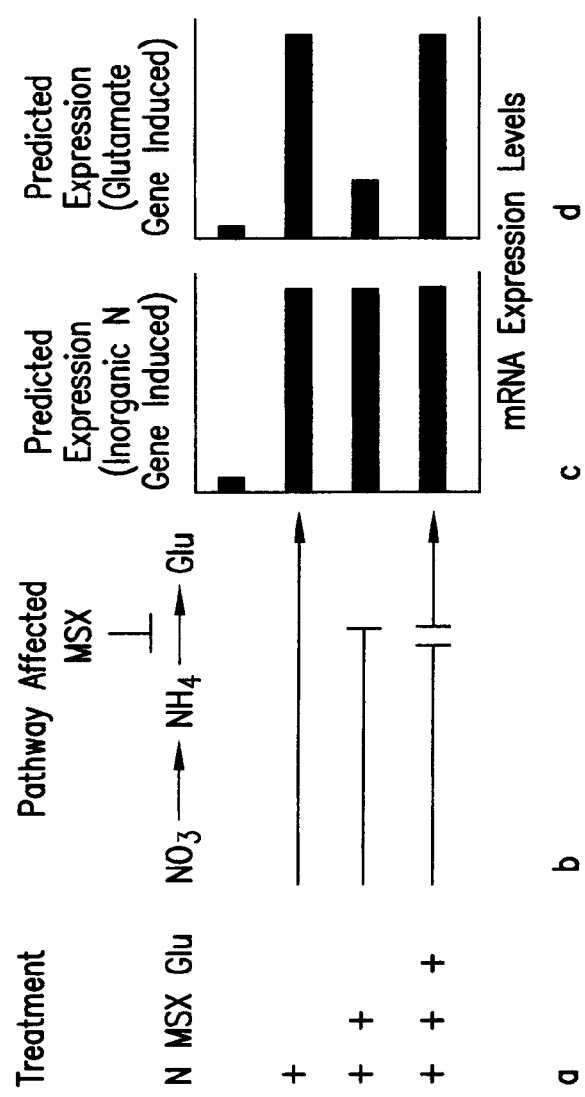

FIG. 7. Signaling by inorganic vs. organic nitrogen can be distinguished by using MSX and Glu treatments. (a) Treatments include N±MSX±Glu. (b) A simplified diagram of the N-metabolic pathway from inorganic nitrate ($NO_3$) to organic Glu, and the block by MSX. Below this pathway are the predicted effects of the given treatments on nitrogen metabolism. Arrows indicate progression through the pathway. Line breaks, represented with a short perpendicular line, indicate the step in the pathway blocked by MSX. (c and d). The expected transcript levels for genes induced by inorganic nitrogen (c) vs. genes regulated by Glu or a Glu-derived metabolite (d).

FIG. 8. Analysis of the expression of asparagine synthetase genes. Shown is a comparison of ASN1 (a) and ASN2 (b) mRNA levels in control seedlings (transferred to 1 mM $NO_3$) along with MSX control (treated with $NO_3$ and 1 mM MSX) compared to seedlings treated with a stepwise combination of Nms, MSX, and Glu/Gln. (a) mRNA levels of ASN1 are increased in Nms, are sensitive to MSX treatment, and can be recovered with exogenous application of Glu or Gln. (b) mRNA levels of ASN2 are increased in Nms. However, this expression is insensitive to MSX treatment and is slightly repressed with exogenous application of Glu or Gln. mRNA levels were normalized to EIF4A (At3g13920).

Figure 9A:
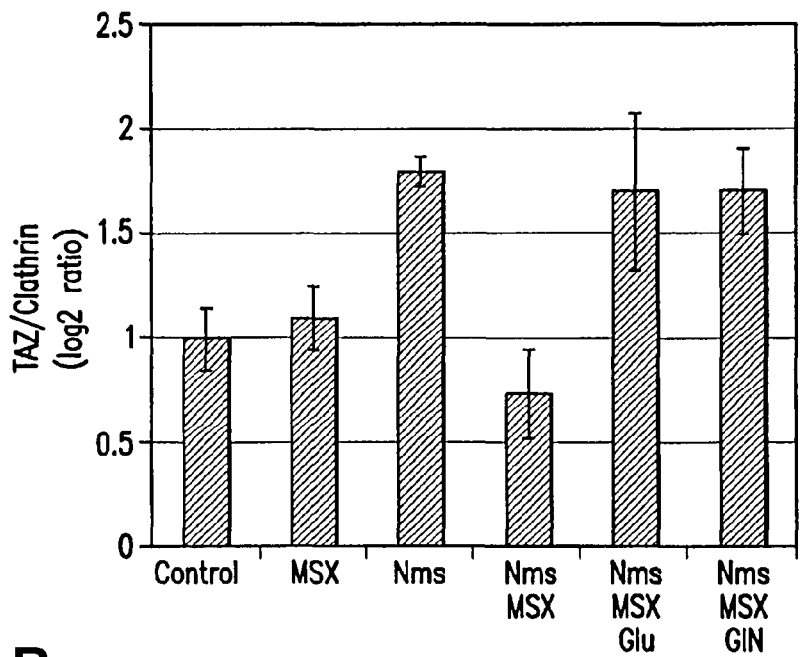
Figure 9B:
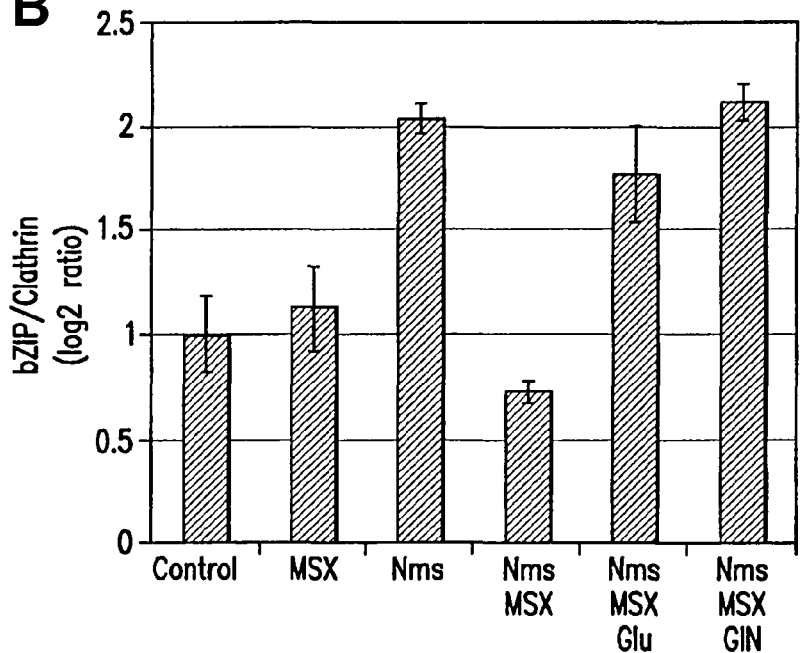

FIG. 9. RT-qPCR confirmation of the regulation for two transcription factors TAZ and bZIP1. Shown is confirmation of TAZ (FIG. 9A) and bZIP1 (FIG. 9B) mRNA levels in control seedlings along with the MSX control and compared to seedlings treated with a stepwise combination of Nms, Nms+MSX, and Nms+MSX+Glu (or Gln). In both cases, although increased expression in the presence of N is blocked in the presence of MSX, this suppression can be overcome by exogenous application of Glu or Gln. Plants transferred to control media do not show mRNA levels different from treatments without MSX. Primers used for RT-qPCR are as follows: TAZ forward, 5'-TCCTCGTCTCGGTCTT-3' (SEQ ID NO:1); reverse, 5'-CAACCACCAGGGATTC-3' (SEQ ID NO:2); bZIP forward, 5'-TCAGGTTCCGACATAGATG-3' (SEQ ID NO:3); reverse, 5'-CCACGGTGTACGTCTACA-3' (SEQ ID NO:4).

Figure 10:
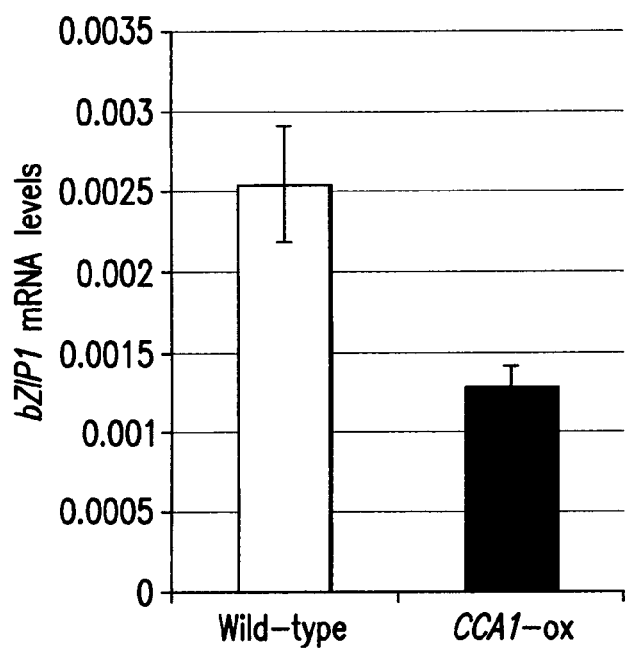

FIG. 10. Analysis of the expression of bZIP1 in the CCA1-ox. To test some of the predictions of our network CCA1-ox and Col-0 plants were collected 3 h after dawn; three biological replicates were taken at each time point. RNA was extracted from whole seedlings (as described in Materials and Methods), and RT-qPCR was performed to measure mRNA levels for bZIP1 (At5g49450). Two technical replicates were carried out for each sample. mRNA levels were normalized to clathrin (At4g24550).

Figure 11:
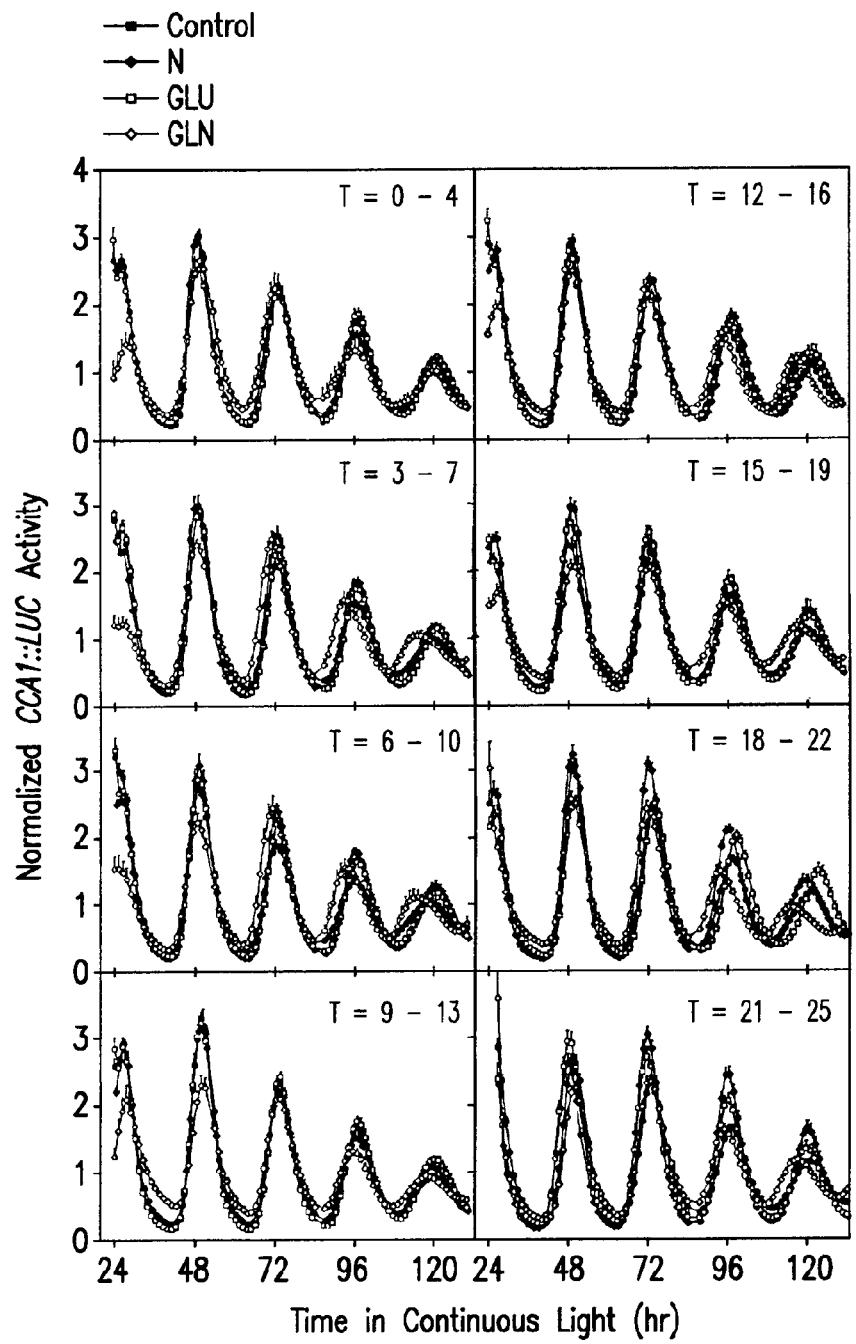

FIG. 11. Circadian regulation of the response of clock gene (CCA1) expression to N-assimilation inhibitors and inorganic and organic N. Mean±SEM luciferase activity of CCA1::LUC in response to exogenous inorganic N, Glu, or Gln is presented. Seedlings were entrained for 8 days in a 16-h white light/8-h dark photoperiod on MS medium containing 1 mM $KNO_3$ before being transferred to continuous light and exposed for 4-h pulses of inorganic N (20 mM $KNO_3$/20 mM $NH_4NO_3$), 10 mM Glu, or 10 mM Gln presented at 3-h intervals over one circadian cycle before return to MS medium containing 1 mM $KNO_3$ in continuous light for luciferase measurements for 6 days. Luciferase activity values were normalized by the mean expression value for the treatment. The entraining photocycle is indicated by the vertical white (light) and gray (dark) bars.

FIG. 12. Schematic diagram of how CCA1/GLK1/bZIP1 transcription factors coordinate the nitrogen regulation of genes in the nitrogen assimilation pathway.

6. DETAILED DESCRIPTION

Master control genes (CCA1, GLK1, and bZIP1) that control N-assimilation in response to Glu sensing have been identified in the present invention. As these genes are transcription factor hubs, they coordinate the N-regulation of the N-assimilatory gene network, with genome-wide responses associated with growth and development in plants. Thus, effecting genome-wide changes in N-assimilation, plant growth and development, by the transgenic manipulation of these master control genes in plants effects nitrogen use efficiency in vegetative tissues (leaves & roots) and also in seed. Changes in levels of N-assimilated into Gln effect changes in growth of vegetative tissues, while changes in levels of Asn affect seed development.

Thus, the present invention relates to the transgenic manipulation of these N-responsive master regulatory genes (CCA1, GLK1, and bZIP1) that control N-assimilation, and other related processes in response to N treatments, so as to increase the overall N-assimilation capacity, whether for increased N usage or N storage. The overexpression of these master control genes (e.g., uncoupled from Glu repression) effectively releases N-assimilation from the feedback repression loop by Glu-leading to increased N-assimilation and usage. As these regulatory genes serve to respond to Glu levels by reciprocally regulating the amount of N-assimilated into Gln versus the amount of Gln metabolized to Asn (for N-storage and transport), the manipulation of these genes in transgenic plants can be used to optimize N-assimilation into Gln versus Asn (FIG. 6). Increased N-assimilation is advantageous in all crops. Additionally, in seed crops, the increased synthesis of Asn increases N-transported and stored in seed.

Thus, in one embodiment, the present invention is directed to a method for improving nitrogen assimilation and usage in a plant in which more nitrogen is available for biosynthesis, said method comprising overexpressing GLK1 in the plant. In another embodiment, the present invention is directed to a method for improving nitrogen assimilation and usage in a plant in which more nitrogen is available for biosynthesis, said method comprising overexpressing CCA1 in the plant. In yet another embodiment, the present invention is directed to a method for improving nitrogen assimilation and usage in a plant in which more nitrogen is available for biosynthesis, said method comprising underexpressing bZIP1 in the plant.

In another embodiment, the method for improving nitrogen assimilation and usage in a plant in which more nitrogen is available for biosynthesis comprises overexpressing CCA1 and GLK1 in the plant. In another embodiment, the method for improving nitrogen assimilation and usage in a plant in which more nitrogen is available for biosynthesis comprises overexpressing CCA1 and underexpressing bZIP1 in the plant, or overexpressing GLK1 and underexpressing bZIP1 in the plant. In yet another embodiment, the method for improving nitrogen assimilation and usage in a plant in which more nitrogen is available for biosynthesis comprises overexpressing CCA1, overexpressing GLK1 and underexpressing bZIP1 in the plant.

The present invention is also directed to methods for altering nitrogen assimilation and storage, e.g., increasing nitrogen storage, in a plant. In one embodiment, the method comprises overexpressing bZIP1 in the plant. In another embodiment, the method comprises underexpressing CCA1 in the plant and/or underexpressing GLK1 in the plant. In another embodiment, the method overexpressing bZIP1 and underexpressing CCA1 and/or GLK1 in the plant. In yet another embodiment, the method comprises overexpressing bZIP1, and underexpressing CCA1 and underexpressing GLK1 in the plant.

In certain embodiments, the plant is species of woody, ornamental, decorative, crop, cereal, fruit, or vegetable. In other embodiments, the plant is a species of one of the following genuses: *Acorus, Aegilops, Allium, Amborella, Antirrhinum, Apium, Arabidopsis, Arachis, Beta, Betula, Brassica, Capsicum, Ceratopteris, Citrus, Cryptomeria, Cycas, Descurainia, Eschscholzia, Eucalyptus, Glycine, Gossypium, Hedyotis, Helianthus, Hordeum, Ipomoea, Lactuca, Linum, Liriodendron, Lotus, Lupinus, Lycopersicon, Medicago, Mesembryanthemum, Nicotiana, Nuphar, Pennisetum, Persea, Phaseolus, Physcomitrella, Picea, Pinus, Poncirus, Populus, Prunus, Robinia, Rosa, Saccharum, Schedonorus, Secale, Sesamum, Solanum, Sorghum, Stevia, Thellungiella, Theobroma, Triphysaria, Triticum, Vitis, Zea*, or *Zinnia*.

The overexpression of a particular gene can be accomplished by any method known in the art, for example, by transforming a plant cell with a nucleic acid vector comprising the coding sequences of the desired gene operably linked to a promoter active in a plant cell such that the desired gene is expressed at levels higher than normal, i.e., levels found in a control/nontransgenic plant. Such promoters can be constitutively active in all or some plant tissues or can be inducible.

The underexpression of a desired gene can be accomplished by any method known in the art, such as knocking out the gene or mutating the gene transgenically such that lower than normal levels of the gene product is produced in the transgenic cells or plant. For example, such mutations include frame-shift mutations or mutations resulting in a stop codon in the wild-type coding sequence, thus preventing expression of the gene product. Another exemplary mutation would be the removal of the transcribed sequences from the plant genome, for example, by homologous recombination. Another method for underexpressing a gene is transgenically introducing an insertion or deletion into the transcribed sequence or an insertion or deletion upstream or downstream of the transcribed sequence such that expression of the gene product is decreased as compared to wild-type or appropriate control. Additionally, microRNA (native or artificial) can be used to target a particular encoding mRNA for degradation, thus reducing the level of the expressed gene product in the transgenic plant cell.

The present invention is also directed to a transgenic plant produced by any of the foregoing methods.

The present invention is also directed to compositions for modulating gene expression in plants. The compositions comprise constructs for the expression of CCA1, GLK1 or bZIP1. In certain embodiments, a construct of the invention comprises a promoter, such as a tissue specific promoter, which is expressed in a plant cell, such as a leaf cell, and promotes the expression of CCA1, GLK1 or bZIP1.

Any of a variety of promoters can be utilized in the constructs of the invention depending on the desired outcome. Tissue-specific or tissue-preferred promoters, inducible promoters, developmental promoters, constitutive promoters and/or chimeric promoters can be used to direct expression of the gene product in specific cells or organs the plant, when fused to the appropriate cell or organ specific promoter.

Chimeric constructs expressing CCA1, GLK1 or bZIP1 in transgenic plants (using constitutive or inducible promoters) can be used in the compositions and methods provided herein to enhance nitrogen assimilation and usage or increase nitrogen storage.

The present invention is also directed to a transgenic plant-derived commercial product. In one embodiment, the transgenic plant is a tree, and said commercial product is pulp, paper, a paper product, or lumber. In another embodiment, the transgenic plant is tobacco, and said commercial product is a cigarette, cigar, or chewing tobacco. In yet another embodiment, the transgenic plant is a crop, and said commercial product is a fruit or vegetable. In yet another embodiment, the transgenic plant is a grain, and said commercial product is bread, flour, cereal, oat meal, or rice. In another embodiment, the product is a biofuel or a plant oil.

6.1 Master Regulators

CIRCADIAN CLOCK ASSOCIATED 1 (CCA1) gene encodes a MYB-related transcription factor involved in the phytochrome induction of a light-harvesting chlorophyll a/b-protein gene. The nucleotide and amino acid sequences of CCA1 from *Arabidopsis* are known, see Accession No. At2g46830. Further, orthologous CCA1 genes from other organisms are also known. For example, the CCA1 gene sequences from poplar can be found under Accession Nos. Poptr1#552368 or Poptr1#731468. The use of CCA1 in the present invention refers not only to the *Arabidopsis* gene but also the orthologous CCA1 gene from other species. Thus, in one embodiment, plant species-specific CCA1 genes can be used in plants of the same species, e.g., tobacco CCA1 can be overexpressed in tobacco. Additionally, such orthologous sequences can be identified and isolated using methods known in the art, such as hybridization methods and then testing the isolated sequences for CCA1 activity, as demonstrated infra. Other methods, such as alignment methods described supra can also be used to identify and isolate orthologous CCA1 sequences.

Golden 2-like genes (GLK) are members of the GARP superfamily of transcription factors. GLK genes are known to be involved in the regulation of chloroplast development in diverse plant species (Fritter et al., 2002, The Plant Journal 31:713-727). The nucleotide and amino acid sequences of GLK1 from *Arabidopsis* are known, see Accession No. At2g20570. Further, orthologous GLK1 genes from other organisms are also known. For example, the GLK1 gene sequences from poplar and rice can be found under Accession Nos. Poptr1#654401 and Os06g24070, respectively. The use of GLK1 in the present invention refers not only to the *Arabidopsis* gene but also the orthologous GLK1 gene from other species. Thus, in one embodiment, plant species-specific GLK1 genes can be used in plants of the same species, e.g., tobacco GLK1 can be overexpressed in tobacco. Additionally, such orthologous sequences can be identified and isolated using methods known in the art, such as hybridization methods and then testing the isolated sequences for GLK1 activity, such as DNA binding activity. Other methods, such as alignment methods described supra can also be used to identify and isolate orthologous GLK1 sequences.

bZIP1 is a transcription factor that belongs to the largest bZIP group in *Arabadopsis*, Group S (Jakoby et al., 2002, Trends Plant Sci 7:106-111). It is thought that Group S bZIP genes are involved in balancing carbohydrate demand and supply (Rook et al., 1998, Plant J 15:253-263). The nucleotide and amino acid sequences of bZIP1 from *Arabidopsis* are known, see Accession No. At5g49450. The use of bZIP1 in the present invention refers not only to the *Arabidopsis* gene but also the orthologous bZIP1 gene from other species. Thus, in one embodiment, plant species-specific bZIP1 genes can be used in plants of the same species, e.g., tobacco bZIP1 can be overexpressed in tobacco. Additionally, such orthologous sequences can be identified and isolated using methods known in the art, such as hybridization methods and then testing the isolated sequences for bZIP1 activity, such as DNA binding activity. Other methods, such as alignment methods described supra can also be used to identify and isolate orthologous bZIP1 sequences.

6.2 Modulation of Gene Expression

The methods of the invention involve modulation of the expression of one, two, three or more target nucleotide sequences in a plant, optionally in specific tissues such as vegetative tissues or leaves or seeds. That is, the expression of a target nucleotide sequence of interest may be increased or decreased. In specific embodiments, the target nucleot-ide sequences are CCA1, GLK1 or bZIP1, which can be increased or decreased.

The target nucleotide sequences may be endogenous or exogenous in origin. By "modulate expression of a target gene" is intended that the expression of the target gene is increased or decreased relative to the expression level in a plant that has not been altered by the methods described herein.

By "increased or over expression" is intended that expression of the target nucleotide sequence is increased over expression observed in conventional transgenic lines for heterologous genes and over endogenous levels of expression for homologous genes. Heterologous or exogenous genes comprise genes that do not occur in the plant of interest in its native state. Homologous or endogenous genes are those that are natively present in the plant genome. Generally, expression of the target sequence is substantially increased. That is expression is increased at least about 25%-50%, preferably about 50%-100%, more preferably about 100%, 200% and greater.

By "decreased expression" or "underexpression" it is intended that expression of the target nucleotide sequence is decreased below expression observed in conventional transgenic lines for heterologous genes and below endogenous levels of expression for homologous genes. Generally, expression of the target nucleotide sequence of interest is substantially decreased. That is expression is decreased at least about 25%-50%, preferably about 50%-100%, more preferably about 100%, 200% and greater.

Expression levels may be assessed by determining the level of a gene product by any method known in the art including, but not limited to determining the levels of the RNA and protein encoded by a particular target gene. For genes that encode proteins, expression levels may determined, for example, by quantifying the amount of the protein present in plant cells, or in a plant or any portion thereof. Alternatively, it desired target gene encodes a protein that has a known measurable activity, then activity levels may be measured to assess expression levels.

6.3 Transformation/Transfection

Any method or delivery system may be used for the delivery and/or transfection of the nucleic acid vectors encoding any of the master regulators of the present invention in the cell. The vectors may be delivered to the plant cell either alone, or in combination with other agents.

Transfection may be accomplished by a wide variety of means, as is known to those of ordinary skill in the art. Such methods include, but are not limited to, *Agrobacterium*-mediated transformation (e.g., Komari et al., 1998, Curr. Opin. Plant Biol., 1:161), particle bombardment mediated transformation (e.g., Finer et al., 1999, Curr. Top. Microbiol. Immunol., 240:59), protoplast electroporation (e.g., Bates, 1999, Methods Mol. Biol., 111:359), viral infection (e.g., Porta and Lomonossoff, 1996, Mol. Biotechnol. 5:209), microinjection, and liposome injection. Other exemplary delivery systems that can be used to facilitate uptake by a cell of the nucleic acid include calcium phosphate and other chemical mediators of intracellular transport, microinjection compositions, and homologous recombination compositions (e.g., for integrating a gene into a preselected location within the chromosome of the cell). Alternative methods may involve, for example, the use of liposomes, electroporation, or chemicals that increase free (or "naked") DNA uptake, transformation using viruses or pollen and the use of microprojection. Standard molecular biology techniques are common in the art (e.g., Sambrook et al., 1989, Molecular Cloning: A Laboratory Manual, 2nd ed., Cold Spring Harbor Laboratory Press, New York). For example, in one embodiment of the present invention, *Arabidopsis* or another plant species is transformed with a gene encoding CCA1, GLK1 or bZIP1 using *Agrobacterium*.

One of skill in the art will be able to select an appropriate vector for introducing the encoding nucleic acid sequence in a relatively intact state. Thus, any vector which will produce a plant carrying the introduced encoding nucleic acid should be sufficient. The selection of the vector, or whether to use a vector, is typically guided by the method of transformation selected.

The transformation of plants in accordance with the invention may be carried out in essentially any of the various ways known to those skilled in the art of plant molecular biology. (See, for example, Methods of Enzymology, Vol. 153, 1987, Wu and Grossman, Eds., Academic Press, incorporated herein by reference).

Plant cells and plants can comprise two or more nucleotide sequence constructs. Any means for producing a plant comprising the nucleotide sequence constructs described herein are encompassed by the present invention. For example, a nucleotide sequence encoding the modulator can be used to transform a plant at the same time as the nucleotide sequence encoding the precursor RNA. The nucleotide sequence encoding the precursor mRNA can be introduced into a plant that has already been transformed with the modulator nucleotide sequence. Alternatively, transformed plants, one expressing the modulator and one expressing the RNA precursor, can be crossed to bring the genes together in the same plant. Likewise, viral vectors may be used to express gene products by various methods generally known in the art. Suitable plant viral vectors for expressing genes should be self-replicating, capable of systemic infection in a host, and stable. Additionally, the viruses should be capable of containing the nucleic acid sequences that are foreign to the native virus forming the vector. Transient expression systems may also be used.

*Agrobacterium* transformation is widely used by those skilled in the art to transform dicotyledonous species. Recently, there has been substantial progress towards the routine production of stable, fertile transgenic plants in almost all economically relevant monocot plants (Toriyama et al., 1988, Bio/Technology 6:1072-1074; Zhang et al., 1988, Plant Cell Rep. 7:379-384; Zhang et al., 1988, Theor. Appl. Genet. 76:835-840; Shimamoto et al., 1989, Nature 338:274-276; Datta et al., 1990, Bio/Technology 8: 736-740; Christou et al., 1991, Bio/Technology 9:957-962; Peng et al., 1991, International Rice Research Institute, Manila, Philippines, pp. 563-574; Cao et al., 1992, Plant Cell Rep. 11:585-591; Li et al., 1993, Plant Cell Rep. 12:250-255; Rathore et al., 1993, Plant Mol. Biol. 21:871-884; Fromm et al., 1990, Bio/Technology 8:833-839; Tomes et al., 1995, "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin); D'Halluin et al., 1992, Plant Cell 4:1495-1505; Walters et al., 1992, Plant Mol. Biol. 18:189-200; Koziel et al., 1993, Biotechnology 11: 194-200; Vasil, I. K., 1994, Plant Mol. Biol. 25:925-937; Weeks et al., 1993, Plant Physiol. 102:1077-1084; Somers et al., 1992, Bio/Technology 10: 1589-1594; WO 92/14828). In particular, *Agrobacterium* mediated transformation is now emerging also as an highly efficient transformation method in monocots (Hiei et al., 1994, The Plant Journal 6:271-282). See also, Shimamoto, K., 1994, Current Opinion in Biotechnology 5:158-162; Vasil et al., 1992, Bio/Technology 10:667-674; Vain et al., 1995, Biotechnology Advances 13(4):653-671; Vasil et al., 1996, Nature Biotechnology 14:702).

The particular choice of a transformation technology will be determined by its efficiency to transform certain plant species as well as the experience and preference of the person practicing the invention with a particular methodology of choice. It will be apparent to the skilled person that the particular choice of a transformation system to introduce nucleic acid into plant cells is not essential to or a limitation of the invention, nor is the choice of technique for plant regeneration.

6.3.1 *Agrobacterium*

A CCA1, GLK1 or bZIP1-encoding nucleic acid sequences or a nucleic acid designed to disrupt expression of CCA1, GLK1 or bZIP1 utilized in the present invention can be introduced into plant cells using Ti plasmids of *Agrobacterium tumefaciens* (*A. tumefaciens*), root-inducing (Ri) plasmids of *Agrobacterium rhizogenes* (*A. rhizogenes*), and plant virus vectors. For reviews of such techniques see, for example, Weissbach & Weissbach, 1988, Methods for Plant Molecular Biology, Academic Press, NY, Section VIII, pp. 421-463; and Grierson & Corey, 1988, Plant Molecular Biology, 2d Ed., Blackie, London, Ch. 7-9, and Horsch et al., 1985, Science, 227:1229.

In using an *A. tumefaciens* culture as a transformation vehicle, it is most advantageous to use a non-oncogenic strain of *Agrobacterium* as the vector carrier so that normal non-oncogenic differentiation of the transformed tissues is possible. It is also preferred that the *Agrobacterium* harbor a binary Ti plasmid system. Such a binary system comprises 1) a first Ti plasmid having a virulence region essential for the introduction of transfer DNA (T-DNA) into plants, and 2) a chimeric plasmid. The chimeric plasmid contains at least one border region of the T-DNA region of a wild-type Ti plasmid flanking the nucleic acid to be transferred. Binary Ti plasmid systems have been shown effective in the transformation of plant cells (De Framond, Biotechnology, 1983, 1:262; Hoekema et al., 1983, Nature, 303:179). Such a binary system is preferred because it does not require integration into the Ti plasmid of *A. tumefaciens*, which is an older methodology.

In some embodiments, a disarmed Ti-plasmid vector carried by *Agrobacterium* exploits its natural gene transferability (EP-A-270355, EP-A-01 16718, Townsend et al., 1984, NAR, 12:8711, U.S. Pat. No. 5,563,055).

Methods involving the use of *Agrobacterium* in transformation according to the present invention include, but are not limited to: 1) co-cultivation of *Agrobacterium* with cultured isolated protoplasts; 2) transformation of plant cells or tissues with *Agrobacterium*; or 3) transformation of seeds, apices or meristems with *Agrobacterium*.

In addition, gene transfer can be accomplished by in planta transformation by *Agrobacterium*, as described by Bechtold et al., (C.R. Acad. Sci. Paris, 1993, 316:1194). This approach is based on the vacuum infiltration of a suspension of *Agrobacterium* cells.

In certain embodiments, a CCA1, GLK1, bZIP1-encoding nucleic acid or mutant thereof is introduced into plant cells by infecting such plant cells, an explant, a meristem or a seed, with transformed *A. tumefaciens* as described above. Under appropriate conditions known in the art, the transformed plant cells are grown to form shoots, roots, and develop further into plants.

Other methods described herein, such as microprojectile bombardment, electroporation and direct DNA uptake can be used where *Agrobacterium* is inefficient or ineffective. Alternatively, a combination of different techniques may be employed to enhance the efficiency of the transformation process, e.g., bombardment with *Agrobacterium*-coated microparticles (EP-A-486234) or microprojectile bombardment to induce wounding followed by co-cultivation with *Agrobacterium* (EP-A-486233).

6.3.2 CaMV

In some embodiments, cauliflower mosaic virus (CaMV) is used as a vector for introducing a desired nucleic acid into plant cells (U.S. Pat. No. 4,407,956). CaMV viral DNA genome can be inserted into a parent bacterial plasmid creating a recombinant DNA molecule which can be propagated in bacteria. After cloning, the recombinant plasmid again can be cloned and further modified by introduction of the desired nucleic acid sequence. The modified viral portion of the recombinant plasmid can then be excised from the parent bacterial plasmid, and used to inoculate the plant cells or plants.

6.3.3 Mechanical and Chemical Means

In some embodiments, a CCA1, GLK1 or bZIP1-encoding nucleic acid or a nucleic acid designed to disrupt expression of CCA1, GLK1 or bZIP1 is introduced into a plant cell using mechanical or chemical means. Exemplary mechanical and chemical means are provided below.

As used herein, the term "contacting" refers to any means of introducing a CCA1, GLK1 or bZIP1-encoding nucleic acid or a nucleic acid designed to disrupt expression of CCA1, GLK1 or bZIP1 into a plant cell, including chemical and physical means as described above. Preferably, contacting refers to introducing the nucleic acid or vector containing the nucleic acid into plant cells (including an explant, a meristem or a seed), via *A. tumefaciens* transformed with the, e.g., GLK1-encoding nucleic acid as described above.

6.3.3.1 Microinjection

In one embodiment, the CCA1, GLK1 or bZIP1-encoding nucleic acid or the nucleic acid designed to disrupt expression of CCA1, GLK1 or bZIP1 can be mechanically transferred into the plant cell by microinjection using a micropipette. See, e.g., WO 92/09696, WO 94/00583, EP 331083, EP 175966, Green et al., 1987, Plant Tissue and Cell Culture, Academic Press, Crossway et al., 1986, Biotechniques 4:320-334.

6.3.3.2 PEG

In other embodiment, the nucleic acid can also be transferred into the plant cell by using polyethylene glycol (PEG) which forms a precipitation complex with genetic material that is taken up by the cell.

6.3.3.3 Electroporation

Electroporation can be used, in another set of embodiments, to deliver a nucleic acid to the cell, e.g., precursor miRNA, or a nucleotide sequence able to be transcribed to produce CCA1, GLK1 or bZIP1 protein (see, e.g., Fromm et al., 1985, PNA5, 82:5824). "Electroporation," as used herein, is the application of electricity to a cell, such as a plant protoplast, in such a way as to cause delivery of a nucleic acid into the cell without killing the cell. Typically, electroporation includes the application of one or more electrical voltage "pulses" having relatively short durations (usually less than 1 second, and often on the scale of milliseconds or microseconds) to a media containing the cells. The electrical pulses typically facilitate the non-lethal transport of extracellular nucleic acids into the cells. The exact electroporation protocols (such as the number of pulses, duration of pulses, pulse waveforms, etc.), will depend on factors such as the cell type, the cell media, the number of cells, the substance(s) to be delivered, etc., and can be determined by those of ordinary skill in the art. Electroporation is discussed in greater detail in, e.g., EP 290395, WO 8706614, Riggs et al., 1986, Proc. Natl. Acad. Sci. USA 83:5602-5606; D'Halluin et al., 1992, Plant Cell 4:1495-1505). Other forms of direct DNA uptake can also be used in the methods provided herein, such as those discussed in, e.g., DE 4005152, WO 9012096, U.S. Pat. No. 4,684,611, Paszkowski et al., 1984, EMBO J. 3:2717-2722.

6.3.3.4 Ballistic and Particle Bombardment

Another method for introducing a CCA1, GLK1 or bZIP1-encoding nucleic acid or a nucleic acid designed to disrupt expression of CCA1, GLK1 or bZIP1 into a plant cell is high velocity ballistic penetration by small particles with the nucleic acid to be introduced contained either within the matrix of such particles, or on the surface thereof (Klein et al., 1987, Nature 327:70). Genetic material can be introduced into a cell using particle gun ("gene gun") technology, also called microprojectile or microparticle bombardment. In this method, small, high-density particles (microprojectiles) are accelerated to high velocity in conjunction with a larger, powder-fired macroprojectile in a particle gun apparatus. The microprojectiles have sufficient momentum to penetrate cell walls and membranes, and can carry RNA or other nucleic acids into the interiors of bombarded cells. It has been demonstrated that such microprojectiles can enter cells without causing death of the cells, and that they can effectively deliver foreign genetic material into intact tissue. Bombardment transformation methods are also described in Sanford et al. (Techniques 3:3-16, 1991) and Klein et al. (Bio/Techniques 10:286, 1992). Although, typically only a single introduction of a new nucleic acid sequence(s) is required, this method particularly provides for multiple introductions.

Particle or microprojectile bombardment are discussed in greater detail in, e.g., the following references: U.S. Pat. No. 5,100,792, EP-A-444882, EP-A-434616; Sanford et al., U.S. Pat. No. 4,945,050; Tomes et al., 1995, "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin); and McCabe et al., 1988, Biotechnology 6:923-926.

6.3.3.5 Colloidal Dispersion

In other embodiments, a colloidal dispersion system may be used to facilitate delivery of a nucleic acid into the cell, for example, GLK1, or a nucleotide sequence able to disrupt expression of GLK1. As used herein, a "colloidal dispersion system" refers to a natural or synthetic molecule, other than those derived from bacteriological or viral sources, capable of delivering to and releasing the nucleic acid to the cell. Colloidal dispersion systems include, but are not limited to, macromolecular complexes, beads, and lipid-based systems including oil-in-water emulsions, micelles, mixed micelles, and liposomes. One example of a colloidal dispersion system is a liposome. Liposomes are artificial membrane vessels. It has been shown that large unilamellar vessels ("LUV"), which-range in size from 0.2 to 4.0 microns, can encapsulate large macromolecules within the aqueous interior and these macromolecules can be delivered to cells in a biologically active form (e.g., Fraley et al., 1981, Trends Biochem. Sci., 6:77).

6.3.3.6 Lipids

Lipid formulations for the transfection and/or intracellular delivery of nucleic acids are commercially available, for instance, from QIAGEN, for example as EFFECTENE® (a non-liposomal lipid with a special DNA condensing enhancer) and SUPER-FECT® (a novel acting dendrimeric technology) as well as Gibco BRL, for example, as LIPO-FECTIN® and LIPOFECTACE®, which are formed of cationic lipids such as N-[1-(2,3-dioleyloxy)-propyl]-N,N,N-trimethylammonium chloride ("DOTMA") and dimethyl dioctadecylammonium bromide ("DDAB"). Liposomes are well known in the art and have been widely described in the literature, for example, in Gregoriadis, G., 1985, Trends in Biotechnology 3:235-241; Freeman et al., 1984, Plant Cell Physiol. 29:1353).

6.3.3.7 Other Methods

In addition to the above, other physical methods for the transformation of plant cells are reviewed in the following and can be used in the methods provided herein. Oard, 1991, Biotech. Adv. 9:1-11. See generally, Weissinger et al., 1988, sAnn Rev. Genet. 22:421-477; Sanford et al., 1987, Particulate Science and Technology 5:27-37; Christou et al., 1988, Plant Physiol. 87:671-674; McCabe et al., 1988, Bio/Technology 6:923-926; Finer and McMullen, 1991, In vitro Cell Dev. Biol. 27P:175-182; Singh et al., 1998, Theor. Appl. Genet. 96:319-324; Datta et al., 1990, Biotechnology 8:736-740; Klein et al., 1988, Proc. Natl. Acad. Sci. USA 85:4305-4309; Klein et al., 1988, Biotechnology 6:559-563; Tomes, U.S. Pat. No. 5,240,855; Buising et al., U.S. Pat. Nos. 5,322,783 and 5,324,646; Klein et al., 1988, Plant Physiol. 91:440-444; Fromm et al., 1990, Biotechnology 8:833-839; Hooykaas-Van Slogteren et al., 1984, Nature (London) 311:763-764; Bytebier et al., 1987, Proc. Natl. Acad. Sci. USA 84:5345-5349; De Wet et al., 1985, The Experimental Manipulation of Ovule Tissues, ed. Chapman et al. (Longman, N.Y.), pp. 197-209; Kaeppler et al., 1990, Plant Cell Reports 9:415-418 and Kaeppler et al., 1992, Theor. Appl. Genet. 84:560-566; Li et al., 1993, Plant Cell Reports 12:250-255 and Christou and Ford, 1995, Annals of Botany 75:407-413; Osjoda et al., 1996, Nature Biotechnology 14:745-750; all of which are herein incorporated by reference.

6.4 Nucleic Acid Constructs

The CCA1, GLK1, bZIP1 sequences of the invention may be provided in nucleotide sequence constructs or expression cassettes for expression in the plant of interest. The cassette will include 5' and 3' regulatory sequences operably linked to an encoding nucleotide sequence of the invention.

The expression cassette may additionally contain at least one additional gene to be co-transformed into the organism. Alternatively, the additional gene(s) can be provided on multiple expression cassettes.

In certain embodiments, an expression cassette can be used with a plurality of restriction sites for insertion of the sequences of the invention to be under the transcriptional regulation of the regulatory regions. The expression cassette can additionally contain selectable marker genes (see below).

The expression cassette will generally include in the 5'-3' direction of transcription, a transcriptional and translational initiation region, a DNA sequence of the invention, e.g., GLK1 or a sequence designed to disrupt expression of GLK1, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

The termination region may be native with the transcriptional initiation region, may be native with the operably linked DNA sequence of interest, or may be derived from another source. Convenient termination regions are available from the Ti-plasmid of A. tumefaciens, such as the octopine synthase and nopaline synthase termination regions. See also Guerineau et al., 1991, Mol. Gen. Genet. 262:141-144; Proudfoot, 1991, Cell 64:671-674; Sanfacon et al., 1991, Genes Dev. 5:141-149; Mogen et al., 1990, Plant Cell 2:1261-1272; Munroe et al., 1990, Gene 91:151-158; Ballas et al., 1989, Nucleic Acids Res. 17:7891-7903; and Joshi et al., 1987, Nucleic Acid Res. 15:9627-9639.

In some embodiments, a nucleic acid (e.g., encoding GLK1 or bZIP1) can be delivered to the cell in a vector. As used herein, a "vector" is any vehicle capable of facilitating the transfer of the nucleic acid to the cell such that the nucleic acid can be processed and/or expressed in the cell. The vector may transport the nucleic acid to the cells with reduced degradation, relative to the extent of degradation that would result in the absence of the vector. The vector optionally includes gene expression sequences or other components (such as promoters and other regulatory elements) able to enhance expression of the nucleic acid within the cell. The invention also encompasses the cells transfected with these vectors, including those cells previously described. In certain embodiments, the cells are transfected or transformed with a vector that specifically (or preferably) overexpresses CCA1 and/or GLK1 in the vegetative tissues of the plant, but not in the majority of other cell types of the plant.

To commence a transformation process in certain embodiments, it is first necessary to construct a suitable vector and properly introduce it into the plant cell. Vector(s) employed in the present invention for transformation of a plant cell include an encoding nucleic acid sequence operably associated with a promoter, such as a leaf-specific promoter. Details of the construction of vectors utilized herein are known to those skilled in the art of plant genetic engineering.

In general, vectors useful in the invention include, but are not limited to, plasmids, phagemids, viruses, other vehicles derived from viral or bacterial sources that have been manipulated by the insertion or incorporation of the nucleotide sequences (or precursor nucleotide sequences) of the invention. Viral vectors useful in certain embodiments include, but are not limited to, nucleic acid sequences from the following viruses: retroviruses; adenovirus, or other adeno-associated viruses; mosaic viruses such as tobamoviruses; potyviruses, nepoviruses, and RNA viruses such as retroviruses. One can readily employ other vectors not named but known to the art. Some viral vectors can be based on non-cytopathic eukaryotic viruses in which non-essential genes have been replaced with the nucleotide sequence of interest. Non-cytopathic viruses include retroviruses, the life cycle of which involves reverse transcription of genomic viral RNA into DNA with subsequent proviral integration into host cellular DNA.

Genetically altered retroviral expression vectors can have general utility for the high-efficiency transduction of nucleic acids. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the cells with viral particles) are well known to those of ordinary skill in the art. Examples of standard protocols can be found in Kriegler, M., 1990, Gene Transfer and Expression, A Laboratory Manual, W.H. Freeman Co., New York, or Murry, E. J. Ed., 1991, Methods in Molecular Biology, Vol. 7, Humana Press, Inc., Cliffton, N.J.

Another-example of a virus for certain applications is the adeno-associated virus, which is a double-stranded DNA virus. The adeno-associated virus can be engineered to be replication-deficient and is capable of infecting a wide range of-cell types and species. The adeno-associated virus further has advantages, such as heat and lipid solvent stability; high transduction frequencies in cells of diverse lineages; and/or lack of superinfection inhibition, which may allow multiple series of transductions.

Another vector suitable for use with the method provided herein is a plasmid vector. Plasmid vectors, have been extensively described in the art and are well-known to those of skill in the art. See, e.g., Sambrook et al., 1989, Molecular Cloning: A Laboratory Manual, Second Edition, Cold Spring Harbor Laboratory Press. These plasmids may have a promoter compatible with the host cell, and the plasmids can express a peptide from a gene operatively encoded within the plasmid. Some commonly used plasmids include pBR322, pUC18, pUC19, pRC/CMV, SV40, and pBlueScript. Other plasmids are well-known to those of ordinary skill in the art. Additionally, plasmids may be custom-designed, for example, using restriction enzymes and ligation reactions, to remove and add specific fragments of DNA or other nucleic acids, as necessary. The present invention also includes vectors for producing nucleic acids or precursor nucleic acids containing a desired nucleotide sequence (which can, for instance, then be cleaved or otherwise processed within the cell to produce a precursor miRNA). These vectors may include a sequence encoding a nucleic acid and an in vivo expression element, as further described below. In some cases, the in vivo expression element includes at least one promoter.

Where appropriate, the gene(s) for enhanced expression may be optimized for expression in the transformed plant. That is, the genes can be synthesized using plant-preferred codons corresponding to the plant of interest. Methods are available in the art for synthesizing plant-preferred genes. See, for example, U.S. Pat. Nos. 5,380,831, and 5,436,391, and Murray et al., 1989, Nucleic Acids Res. 17:477-498.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When desired, the sequence is modified to avoid predicted hairpin secondary mRNA structures. However, it is recognized that in the case of nucleotide sequences encoding the miRNA precursors, one or more hairpin and other secondary structures may be desired for proper processing of the precursor into an mature miRNA and/or for the functional activity of the miRNA in gene silencing.

The expression cassettes can additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al., 1989, PNAS USA 86:6126-6130); potyvirus leaders, for example, TEV leader (Tobacco Etch Virus) (Allison et al., 1986); MDMV leader (Maize Dwarf Mosaic Virus); Virology 154:9-20), and human immunoglobulin heavy-chain binding protein (BiP), (Macejak et al., 1991, Nature 353:90-94); untranslated leader from the coat protein miRNA of alfalfa mosaic virus (AMV RNA 4) (Jobling et al., 1987, Nature 325:622-625); tobacco mosaic virus leader (TMV) (Gallie et al., 1989, Molecular Biology of RNA, ed. Cech (Liss, New York), pp. 237-256); and maize chlorotic mottle virus leader (MCMV) (Lommel et al., 1991, Virology 81:382-385). See also, Della-Cioppa et al., 1987, Plant Physiol. 84:965-968.

In preparing the expression cassette, the various DNA fragments can be manipulated, so as to provide for the DNA sequences in the proper orientation and, as appropriate, in the proper reading frame. Toward this end, adapters or linkers can be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

An illustrative vector encoding CCA1 for overexpression in plants is described infra. Wang et al., 1998, Cell 93:1207-1217 also describes a vector for overexpressing CCA1 in plants. An illustrative vector encoding GLK1 for overexpression in plants is described infra. Further, Fitter et al., 2002, The Plant Journal 31:713-727 describe an insertion mutant in the GLK1 gene such that expression of GLK1 is disrupted.

6.5 Promoters and Other Regulatory Sequences

In the broad method of the invention, at least one nucleic acid sequence encoding CCA1, GLK1 or bZIP1 or a nucleic acid designed to disrupt expression of same is operably linked with a promoter, such as a leaf-preferred or leaf-specific promoter. It may be desirable to introduce more than one copy of a polynucleotide into a plant for enhanced expression. For example, multiple copies of a GLK1 polynucleotide would have the effect of increasing production of GLK1 even further in the plant. In specific embodiments, the GLK1 polynucleotide is expressed primarily or entirely in vegetative cells of the plant.

In general, promoters are found positioned 5' (upstream) of the genes that they control. Thus, in the construction of promoter gene combinations, the promoter is preferably positioned upstream of the gene and at a distance from the transcription start site that approximates the distance between the promoter and the gene it controls in the natural setting. As is known in the art, some variation in this distance can be tolerated without loss of promoter function. Similarly, the preferred positioning of a regulatory element, such as an enhancer, with respect to a heterologous gene placed under its control reflects its natural position relative to the structural gene it naturally regulates. In certain specific embodiments, bZIP1 is under the control of a seed-specific promoter, and may optionally comprise other regulatory elements that result in constitutive or inducible expression of bZIP1.

Thus, the nucleic acid, in one embodiment, is operably linked to a gene expression sequence, which directs the expression of the nucleic acid within the cell. A "gene expression sequence," as used herein, is any regulatory nucleotide sequence, such as a promoter sequence or promoter-enhancer combination, which facilitates the efficient transcription and translation of the nucleotide sequence to which it is operably linked. The gene expression sequence may, for example, be a eukaryotic promoter or a viral promoter, such as a constitutive or inducible promoter. Promoters and enhancers consist of short arrays of DNA sequences that interact specifically with cellular proteins involved in transcription, for instance, as discussed in Maniatis et al., 1987, Science 236:1237. Promoter and enhancer elements have been isolated from a variety of eukaryotic sources including genes in plant, yeast, insect and mammalian cells and viruses (analogous control elements, i.e., promoters, are also found in prokaryotes). In some embodiments, the nucleic acid is linked to a gene expression sequence which permits expression of the nucleic acid in a plant cell. A sequence which permits expression of the nucleic acid in a plant cell is one which is selectively active in the particular plant cell and thereby causes the expression of the nucleic acid in these cells. Those of ordinary skill in the art will be able to easily identify promoters that are capable of expressing a nucleic acid in a cell based on the type of plant cell.

A number of promoters can be used in the practice of the invention. The promoters can be selected based on the desired outcome. Generally, the nucleotide sequence and the modulator sequences can be combined with promoters of choice to alter gene expression if the target sequences in the tissue or organ of choice. Thus, the nucleotide sequence or modulator nucleotide sequence can be combined with constitutive, tissue-preferred, inducible, developmental, or other promoters for expression in plants depending upon the desired outcome.

The selection of a particular promoter and enhancer depends on what cell type is to be used and the mode of delivery. For example, a wide variety of promoters have been isolated from plants and animals, which are functional not only in the cellular source of the promoter, but also in numerous other plant species. There are also other promoters (e.g., viral and Ti-plasmid) which can be used. For example, these promoters include promoters from the Ti-plasmid, such as the octopine synthase promoter, the nopaline synthase promoter, the mannopine synthase promoter, and promoters from other open reading frames in the T-DNA, such as ORF7, etc. Promoters isolated from plant viruses include the 35S promoter from cauliflower mosaic virus. Promoters that have been isolated and reported for use in plants include ribulose-1,3-biphosphate carboxylase small subunit promoter, phaseolin promoter, etc. Thus, a variety of promoters and regulatory elements may be used in the expression vectors of the present invention.

Promoters useful in the compositions and methods provided herein include both natural constitutive and inducible promoters as well as engineered promoters. The CaMV promoters are examples of constitutive promoters. Other constitutive mammalian promoters include, but are not limited to, polymerase promoters as well as the promoters for the following genes: hypoxanthine phosphoribosyl transferase ("HPTR"), adenosine deaminase, pyruvate kinase, and alpha-actin.

Promoters useful as expression elements of the invention also include inducible promoters. Inducible promoters are expressed in the presence of an inducing agent. For example, a metallothionein promoter can be induced to promote transcription in the presence of certain metal ions. Other inducible promoters are known to those of ordinary skill in the art. The in vivo expression element can include, as necessary, 5' non-transcribing and 5' non-translating sequences involved with the initiation of transcription, and can optionally include enhancer sequences or upstream activator sequences.

For example, in some embodiments an inducible promoter is used to allow control of nucleic acid expression through the presentation of external stimuli (e.g., environmentally inducible promoters), as discussed below. Thus, the timing and amount of nucleic acid expression can be controlled in some cases. Non-limiting examples of expression systems, promoters, inducible promoters, environmentally inducible promoters, and enhancers are well known to those of ordinary skill in the art. Examples include those described in International Patent Application Publications WO 00/12714, WO 00/11175, WO 00/12713, WO 00/03012, WO 00/03017, WO 00/01832, WO 99/50428, WO 99/46976 and U.S. Pat. Nos. 6,028,250, 5,959,176, 5,907,086, 5,898,096, 5,824,857, 5,744,334, 5,689,044, and 5,612,472. A general descriptions of plant expression vectors and reporter genes can also be found in Gruber et al., 1993, "Vectors for Plant Transformation," in Methods in Plant Molecular Biology & Biotechnology, Glich et al., Eds., p. 89-119, CRC Press.

For plant expression vectors, viral promoters that can be used in certain embodiments include the 35S RNA and 19S RNA promoters of CaMV (Brisson et al., Nature, 1984, 310:511; Odell et al., Nature, 1985, 313:810); the full-length transcript promoter from Figwort Mosaic Virus (FMV) (Gowda et al., 1989, J. Cell Biochem., 13D: 301) and the coat protein promoter to TMV (Takamatsu et al., 1987, EMBO J. 6:307). Alternatively, plant promoters such as the light-inducible promoter from the small subunit of ribulose bis-phosphate carboxylase (ssRUBISCO) (Coruzzi et al., 1984, EMBO J., 3:1671; Broglie et al., 1984, Science, 224:838); mannopine synthase promoter (Velten et al., 1984, EMBO J., 3:2723) nopaline synthase (NOS) and octopine synthase (OCS) promoters (carried on tumor-inducing plasmids of *Agrobacterium tumefaciens*) or heat shock promoters, e.g., soybean hsp17.5-E or hsp17.3-B (Gurley et al., 1986, Mol. Cell. Biol., 6:559; Severin et al., 1990, Plant Mol. Biol., 15:827) may be used. Exemplary viral promoters which function constitutively in eukaryotic cells include, for example, promoters from the simian virus, papilloma virus, adenovirus, human immunodeficiency virus, Rous sarcoma virus, cytomegalovirus, the long terminal repeats of Moloney leukemia virus and other retroviruses, and the thymidine kinase promoter of herpes simplex virus. Other constitutive promoters are known to those of ordinary skill in the art.

To be most useful, an inducible promoter should 1) provide low expression in the absence of the inducer; 2) provide high expression in the presence of the inducer; 3) use an induction scheme that does not interfere with the normal physiology of the plant; and 4) have no effect on the expression of other genes. Examples of inducible promoters useful in plants include those induced by chemical means, such as the yeast metallothionein promoter which is activated by copper ions (Mett et al., Proc. Natl. Acad. Sci., U.S.A., 90:4567, 1993); In2-1 and In2-2 regulator sequences which are activated by substituted benzenesulfonamides, e.g., herbicide safeners (Hershey et al., Plant Mol. Biol., 17:679, 1991); and the GRE regulatory sequences which are induced by glucocorticoids (Schena et al., Proc. Natl. Acad Sci., U.S.A., 88:10421, 1991). Other promoters, both constitutive and inducible will be known to those of skill in the art.

A number of inducible promoters are known in the art. For resistance genes, a pathogen-inducible promoter can be utilized. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al., 1983, Neth. J. Plant Pathol. 89:245-254; Uknes et al., 1992, Plant Cell 4:645-656; and Van Loon, 1985, Plant Mol. Virol. 4:111-116. Of particular interest are promoters that are expressed locally at or near the site of pathogen infection. See, for example, Marineau et al., 1987, Plant Mol. Biol. 9:335-342; Matton et al., 1989, Molecular Plant-Microbe Interactions 2:325-331; Somsisch et al., 1986, Proc. Natl. Acad. Sci. USA 83:2427-2430; Somsisch et al., 1988, Mol. Gen. Genet. 2:93-98; and Yang, 1996, Proc. Natl. Acad. Sci. USA 93:14972-14977. See also, Chen et al., 1996, Plant J. 10:955-966; Zhang et al., 1994, Proc. Natl. Acad. Sci. USA 91:2507-2511; Warner et al., 1993, Plant J. 3:191-201; Siebertz et al., 1989, Plant Cell 1:961-968; U.S. Pat. No. 5,750,386; Cordero et al., 1992, Physiol. Mol. Plant Path. 41:189-200; and the references cited therein.

Additionally, as pathogens find entry into plants through wounds or insect damage, a wound-inducible promoter may be used in the DNA constructs of the invention. Such wound-inducible promoters include potato proteinase inhibitor (pin II) gene (Ryan, 1990, Ann. Rev. Phytopath. 28:425-449; Duan et al., 1996, Nature Biotechnology 14:494-498); wun1 and wun2, U.S. Pat. No. 5,428,148; win1 and win2 (Stanford et al., 1989, Mol. Gen. Genet. 215:200-208); systemin (McGurl et al., 1992, Science 225: 1570-1573); WIPI (Rohmeier et al., 1993, Plant Mol. Biol. 22:783-792; Eckelkamp et al., 1993, FEBS Letters 323:73-76); MPI gene (Corderok et al., 1994, Plant J. 6(2):141-150); and the like. Such references are herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1 a promoter, which is activated by salicylic acid. Other chemical-regulated promoters of interest include steroid-responsive promoters (see, for example, the glucocorticoid-inducible promoter in Schena et al., 1991, Proc. Natl. Acad. Sci. USA 88:10421-10425 and McNellis et al., 1998, Plant J. 14(2):247-257) and tetramiR167e-inducible and tetramiR167e-repressible promoters (see, for example, Gatz et al., 1991, Mol. Gen. Genet. 227:229-237, and U.S. Pat. Nos. 5,814,618 and 5,789,156), herein incorporated by reference.

Where enhanced expression in particular tissues is desired, tissue-preferred promoters can be utilized. Tissue-preferred promoters include those described by Yamamoto et al., 1997, Plant J. 12(2):255-265; Kawamata et al., 1997, Plant Cell Physiol. 38(7):792-803; Hansen et al., 1997, Mol. Gen Genet. 254(3):337-343; Russell et al., 1997, Transgenic Res. 6(2):157-168; Rinehart et al., 1996, Plant Physiol. 112(3):1331-1341; Van Camp et al., 1996, Plant Physiol. 112(2):525-535; Canevascini et al., 1996, Plant Physiol. 12(2):513-524; Yamamoto et al., 1994, Plant Cell Physiol. 35(5):773-778; Lam, 1994, Results Probl. Cell Differ. 20:181-196; Orozco et al., 1993, Plant Mol. Biol. 23(6): 1129-1138; Matsuoka et al., 1993, Proc Natl. Acad. Sci. USA 90(20):9586-9590; and Guevara-Garcia et al., 1993, Plant J 4(3):495-505.

The particular promoter selected should be capable of causing sufficient expression to result in the production of an effective amount of structural gene product in the transgenic plant, e.g., GLK1 to cause upregulation of genes such as GLN1.3 and increased nitrogen assimilation, biomass, overall plant growth or yield, and/or other phenotypes described herein, as compared to wild type. The promoters used in the vector constructs of the present invention may be modified, if desired, to affect their control characteristics. In certain embodiments, chimeric promoters can be used.

There are promoters known which limit expression to particular plant parts or in response to particular stimuli. One skilled in the art will know of many such plant part-specific promoters which would be useful in the present invention. In certain embodiments, to provide pericycle-specific expression, any of a number of promoters from genes in *Arabidopsis* can be used. In some embodiments, the promoter from one (or more) of the following genes may be used: (i) At1g11080, (ii) At3g60160, (iii) At1g24575, (iv) At3g45160, or (v) At1g23130. In specific embodiments, we will also use (vi) promoter elements from the GFP-marker line used in Gifford et al. (in preparation) (see also, Bonke et al., 2003, Nature 426, 181-6; Tian et al., 2004, Plant Physiol 135, 25-38). Several of the predicted genes have a number of potential orthologs in rice and poplar and thus are predicted that they will be applicable for use in crop species; (i) Os04g44410, Os10g39560, Os06g51370, Os02g42310, Os01g22980, Os05g06660, and Poptr1#568263, Poptr1#555534, Poptr1#365170; (ii) Os04g49900, Os04g49890, Os01g67580, and Poptr1#87573, Poptr1#80582, Poptr1#565079, Poptr1#99223.

Promoters used in the nucleic acid constructs of the present invention can be modified, if desired, to affect their control characteristics. For example, the CaMV 35S promoter may be ligated to the portion of the ssRUBISCO gene that represses the expression of ssRUBISCO in the absence of light, to create a promoter which is active in leaves but not in roots. The resulting chimeric promoter may be used as described herein. For purposes of this description, the phrase "CaMV 35S" promoter thus includes variations of CaMV 35S promoter, e.g., promoters derived by means of ligation with operator regions, random or controlled mutagenesis, etc. Furthermore, the promoters may be altered to contain multiple "enhancer sequences" to assist in elevating gene expression.

An efficient plant promoter that may be used in specific embodiments is an "overproducing" or "overexpressing" plant promoter. Overexpressing plant promoters that can be used in the compositions and methods provided herein include the promoter of the small sub-unit ("ss") of the ribulose-1,5-biphosphate carboxylase from soybean (e.g., Berry-Lowe et al., 1982, J. Molecular & App. Genet., 1:483), and the promoter of the chorophyll a-b binding protein. These two promoters are known to be light-induced in eukaryotic plant cells. For example, see Cashmore, Genetic Engineering of plants: An Agricultural Perspective, p. 29-38; Coruzzi et al., 1983, J. Biol. Chem., 258:1399; and Dunsmuir et al., 1983, J. Molecular & App. Genet., 2:285.

The promoters and control elements of, e.g., SUCS (root nodules; broadbean; Kuster et al., 1993, Mol Plant Microbe Interact 6:507-14) for roots can be used in compositions and methods provided herein to confer tissue specificity.

In certain embodiment, two promoter elements can be used in combination, such as, for example, (i) an inducible element responsive to a treatment that can be provided to the plant prior to N-fertilizer treatment, and (ii) a plant tissue-specific expression element to drive expression in the specific tissue alone.

Any promoter of other expression element described herein or known in the art may be used either alone or in combination with any other promoter or other expression element described herein or known in the art. For example, promoter elements that confer tissue specific expression of a gene can be used with other promoter elements conferring constitutive or inducible expression.

6.6 Isolating Related Promoter Sequences

Promoter and promoter control elements that are related to those described in herein can also be used in the compositions and methods provided herein. Such related sequence can be isolated utilizing (a) nucleotide sequence identity; (b) coding sequence identity of related, orthologous genes; or (c) common function or gene products.

Relatives can include both naturally occurring promoters and non-natural promoter sequences. Non-natural related promoters include nucleotide substitutions, insertions or deletions of naturally-occurring promoter sequences that do not substantially affect transcription modulation activity. For example, the binding of relevant DNA binding proteins can still occur with the non-natural promoter sequences and promoter control elements of the present invention.

According to current knowledge, promoter sequences and promoter control elements exist as functionally important regions, such as protein binding sites, and spacer regions. These spacer regions are apparently required for proper positioning of the protein binding sites. Thus, nucleotide substitutions, insertions and deletions can be tolerated in these spacer regions to a certain degree without loss of function.

In contrast, less variation is permissible in the functionally important regions, since changes in the sequence can interfere with protein binding. Nonetheless, some variation in the functionally important regions is permissible so long as function is conserved.

The effects of substitutions, insertions and deletions to the promoter sequences or promoter control elements may be to increase or decrease the binding of relevant DNA binding proteins to modulate transcript levels of a polynucleotide to be transcribed. Effects may include tissue-specific or condition-specific modulation of transcript levels of the polypeptide to be transcribed. Polynucleotides representing changes to the nucleotide sequence of the DNA-protein contact region by insertion of additional nucleotides, changes to identity of relevant nucleotides, including use of chemically-modified bases, or deletion of one or more nucleotides are considered encompassed by the present invention.

Typically, related promoters exhibit at least 80% sequence identity, preferably at least 85%, more preferably at least 90%, and most preferably at least 95%, even more preferably, at least 96%, at least 97%, at least 98% or at least 99% sequence identity. Such sequence identity can be calculated by the algorithms and computers programs described above.

Usually, such sequence identity is exhibited in an alignment region that is at least 75% of the length of a sequence or corresponding full-length sequence of a promoter described herein; more usually at least 80%; more usually, at least 85%, more usually at least 90%, and most usually at least 95%, even more usually, at least 96%, at least 97%, at least 98% or at least 99% of the length of a sequence of a promoter described herein.

The percentage of the alignment length is calculated by counting the number of residues of the sequence in region of strongest alignment, e.g., a continuous region of the sequence that contains the greatest number of residues that are identical to the residues between two sequences that are being aligned. The number of residues in the region of strongest alignment is divided by the total residue length of a sequence of a promoter described herein. These related promoters may exhibit similar preferential transcription as those promoters described herein.

In certain embodiments, a promoter, such as a leaf-preferred or leaf-specific promoter, can be identified by sequence homology or sequence identity to any root specific promoter identified herein. In other embodiments, orthologous genes identified herein as leaf-specific genes (e.g., the same gene or different gene that if functionally equivalent) for a given species can be identified and the associated promoter can also be used in the compositions and methods provided herein. For example, using high, medium or low stringency conditions, standard promoter rules can be used to identify other useful promoters from orthologous genes for use in the compositions and methods provided herein. In specific embodiments, the orthologous gene is a gene expressed only or primarily in the root, such as pericycle cells.

Polynucleotides can be tested for activity by cloning the sequence into an appropriate vector, transforming plants with the construct and assaying for marker gene expression. Recombinant DNA constructs can be prepared, which comprise the polynucleotide sequences of the invention inserted into a vector suitable for transformation of plant cells. The construct can be made using standard recombinant DNA techniques (Sambrook et al., 1989) and can be introduced to the species of interest by *Agrobacterium*-mediated transformation or by other means of transformation as referenced below.

The vector backbone can be any of those typical in the art such as plasmids, viruses, artificial chromosomes, BACs, YACs and PACs and vectors of the sort described by (a) BAC: Shizuya et al., 1992, Proc. Natl. Acad. Sci. USA 89: 8794-8797; Hamilton et al., 1996, Proc. Natl. Acad. Sci. USA 93: 9975-9979; (b) YAC: Burke et al., 1987, Science 236:806-812; (c) PAC: Sternberg N. et al., 1990, Proc Natl Acad Sci USA. January; 87(1):103-7; (d) Bacteria-Yeast Shuttle Vectors: Bradshaw et al., 1995, Nucl Acids Res 23: 4850-4856; (e) Lambda Phage Vectors: Replacement Vector, e.g., Frischauf et al., 1983, J. Mol. Biol. 170: 827-842; or Insertion vector, e.g., Huynh et al., 1985, In: Glover N M (ed) DNA Cloning: A practical Approach, Vol. 1 Oxford: IRL Press; T-DNA gene fusion vectors: Walden et al., 1990, Mol Cell Biol 1: 175-194; and (g) Plasmid vectors: Sambrook et al., infra.

Typically, the construct comprises a vector containing a sequence of the present invention operationally linked to any marker gene. The polynucleotide was identified as a promoter by the expression of the marker gene. Although many marker genes can be used, Green Fluorescent Protein (GFP) is preferred. The vector may also comprise a marker gene that confers a selectable phenotype on plant cells. The marker may encode biocide resistance, particularly antibiotic resistance, such as resistance to kanamycin, G418, bleomycin, hygromycin, or herbicide resistance, such as resistance to chlorosulfuron or phosphinotricin (see below). Vectors can also include origins of replication, scaffold attachment regions (SARs), markers, homologous sequences, introns, etc.

6.7 Tissue or Cell-Type Preferential Transcription

The invention also provides a method of providing increased transcription of a nucleic acid sequence in a selected tissue, such as vegetative tissues, leaves, seeds, fruit, etc. The method comprises growing a plant having integrated in its genome a nucleic acid construct comprising, an exogeneous gene encoding CCA1, GLK1 or bZIP1, said gene operably associated with a tissue specific promoter, whereby transcription of said gene is increased (or decreased) in said selected tissue.

Specific promoters may be used in the compositions and methods provided herein. As used herein, "specific promoters" refers to a subset of promoters that have a high preference for modulating transcript levels in a specific tissue or organ or cell and/or at a specific time during development of an organism. By "high preference" is meant at least 3-fold, preferably 5-fold, more preferably at least 10-fold still more preferably at least 20-fold, 50-fold or 100-fold increase in transcript levels under the specific condition over the transcription under any other reference condition considered. Typical examples of temporal and/or tissue or organ specific promoters of plant origin that can be used in the compositions and methods of the present invention, include RCc2 and RCc3, promoters that direct root-specific gene transcription in rice (Xu et al., 1995, Plant Mol. Biol. 27:237 and TobRB27, a root-specific promoter from tobacco (Yamamoto et al., 1991, Plant Cell 3:371). Examples of tissue-specific promoters under developmental control include promoters that initiate transcription only in certain tissues or organs, such as roots "Preferential transcription" is defined as transcription that occurs in a particular pattern of cell types or developmental times or in response to specific stimuli or combination thereof. Non-limitative examples of preferential transcription include: high transcript levels of a desired sequence in root tissues; detectable transcript levels of a desired sequence in certain cell types during embryogenesis; and low transcript levels of a desired sequence under drought conditions. Such preferential transcription can be determined by measuring initiation, rate, and/or levels of transcription.

Promoters and control elements providing preferential transcription in a root can modulate growth, metabolism, development, nutrient uptake, nitrogen fixation, or modulate energy and nutrient utilization in host cells or organisms. In a plant, for example, preferential modulation of genes, transcripts, and/or in a leaf, is useful (1) to modulate root size, shape, and development; (2) to modulate the number of roots, or root hairs; (3) to modulate mineral, fertilizer, or water uptake; (4) to modulate transport of nutrients; or (4) to modulate energy or nutrient usage in relation to other organs and tissues. Up-regulation and transcription down-regulation is useful for these applications. For instance, genes, transcripts, and/or polypeptides that increase growth, for example, may require up-regulation of transcription. In contrast, transcriptional down-regulation may be desired to inhibit nutrient usage in a root to be directed to the leaf instead, for instance.

Typically, promoter or control elements, which provide preferential transcription in cells, tissues, or organs of a root, produce transcript levels that are statistically significant as compared to other cells, organs or tissues. For preferential up-regulation of transcription, promoter and control elements produce transcript levels that are above background of the assay.

Root-preferred promoters are known and can be selected from the many available from the literature. See, for example, Hire et al., 1992, Plant Mol. Biol. 20(2): 207-218 (soybean root-preferred glutamine synthetase gene); Keller and Baumgartner, 1991, Plant Cell 3(10):1051-1061 (root-preferred control element in the GRP 1.8 gene of French bean); Sanger et al., 1990, Plant Mol. Biol. 14(3):433-443 (root-preferred promoter of the mannopine synthase (MAS) gene of *Agrobacterium tumefaciens*); Miao et al., 1991, Plant Cell 3(1):11-22 (full-length cDNA clone encoding cytosolic glutamine synthetase (GS), which is expressed in roots and root nodules of soybean). Bogusz et al., 1990, Plant Cell 2(7):633-641 (root-preferred promoters from hemoglobin genes from the nitrogen-fixing nonlegume *Parasponia andersonii* and the related non-nitrogen-fixing nonlegume *Trema tomentosa*). Leach and Aoyagi, 1991, Plant Science (Limerick) 79(1):69-76 (rolC and rolD root-inducing genes of *Agrobacterium rhizogenes*); Teeri et al., 1989, EMBO J. 8(2):343-350) (octopine synthase and TR2' gene); (VfENOD-GRP3 gene promoter); Kuster et al., 1995, Plant Mol. Biol. 29(4):759-772 and Capana et al., 1994, Plant Mol. Biol. 25(4):681-691 rolB promoter. See also U.S. Pat. Nos. 5,837,876; 5,750,386; 5,633,363; 5,459,252; 5,401,836; 5,110,732; and 5,023,179, root-specific glutamine synthetase (see Tingey et al., 1987, EMBO J., 6:1-9; Edwards et al., 1990, PNAS, 87:3439-3463). In addition, promoters of the above-listed orthologous genes in other plant species can be identified and used in the compositions and methods provided herein.

In specific embodiments, the compositions and methods provided herein use leaf-specific promoters operably associated to a nucleotide encoding bZIP1. In certain embodiments, the promoter is a constitutive or inducible promoter. In another specific embodiment, the compositions and methods provided herein use vegetative tissue-specific promoters operably associated to a nucleotide encoding CCA1 and/or GLK1. In certain embodiments, the promoter is a constitutive or inducible promoter.

6.8 Selectable Markers

Using any gene transfer technique, such as the above-listed techniques, an expression vector harboring the nucleic acid may be transformed into a cell to achieve temporary or prolonged expression. Any suitable expression system may be used, so long as it is capable of undergoing transformation and expressing of the precursor nucleic acid in the cell. In one embodiment, a pET vector (Novagen, Madison, Wis.), or a pBI vector (Clontech, Palo Alto, Calif.) is used as the expression vector. In some embodiments an expression vector further encoding a green fluorescent protein ("GFP") is used to allow simple selection of transfected cells and to monitor expression levels. Non-limiting examples of such vectors include Clontech's "Living Colors Vectors" pEYFP and pEYFP-C.

The recombinant construct of the present invention may include a selectable marker for propagation of the construct. For example, a construct to be propagated in bacteria preferably contains an antibiotic resistance gene, such as one that confers resistance to kanamycin, tetracycline, streptomycin, or chloramphenicol. Suitable vectors for propagating the construct include plasmids, cosmids, bacteriophages or viruses, to name but a few.

In addition, the recombinant constructs may include plant-expressible selectable or screenable marker genes for isolating, identifying or tracking of plant cells transformed by these constructs. Selectable markers include, but are not limited to, genes that confer antibiotic resistances (e.g., resistance to kanamycin or hygromycin) or herbicide resistance (e.g., resistance to sulfonylurea, phosphinothricin, or glyphosate). Screenable markers include, but are not limited to, the genes encoding .beta.-glucuronidase (Jefferson, 1987, Plant Molec Biol. Rep 5:387-405), luciferase (Ow et al., 1986, Science 234:856-859), B and Cl gene products that regulate anthocyanin pigment production (Goff et al., 1990, EMBO J 9:2517-2522).

In some cases, a selectable marker may be included with the nucleic acid being delivered to the cell. As used herein, the term "selectable marker" refers to the use of a gene that encodes an enzymatic or other detectable activity (e.g., luminescence or fluorescence) that confers the ability to grow in medium lacking what would otherwise be an essential nutrient. A selectable marker may also confer resistance to an antibiotic or drug upon the cell in which the selectable marker is expressed. Selectable markers may be "dominant" in some cases; a dominant selectable marker encodes an enzymatic or other activity (e.g., luminescence or fluorescence) that can be detected in any cell or cell line.

Optionally, a selectable marker may be associated with the CCA1-, GLK1 or bZIP1-encoding nucleic acid. Preferably, the marker gene is an antibiotic resistance gene whereby the appropriate antibiotic can be used to select for transformed cells from among cells that are not transformed. Examples of suitable selectable markers include adenosine deaminase, dihydrofolate reductase, hygromycin-B-phosphotransferase, thymidine kinase, xanthine-guanine phospho-ribosyltransferase and amino-glycoside 3'-O-phosphotransferase II. Other suitable markers will be known to those of skill in the art.

6.9 Selection and Identification of Transformed Plants and Plant Cells

According to the present invention, desired plants may be obtained by engineering the disclosed gene constructs into a variety of plant cell types, including but not limited to, protoplasts, tissue culture cells, tissue and organ explants, pollens, embryos as well as whole plants. In specific embodiments, the gene constructs are engineered into leaves, preferably with the use of a leaf-specific promoter.

In an embodiment of the present invention, the engineered plant material is selected or screened for transformants (those that have incorporated or integrated the introduced gene construct(s)) following the approaches and methods described below. An isolated transformant may then be regenerated into a plant. Alternatively, the engineered plant material may be regenerated into a plant or plantlet before subjecting the derived plant or plantlet to selection or screening for the marker gene traits. Procedures for regenerating plants from plant cells, tissues or organs, either before or after selecting or screening for marker gene(s), are well known to those skilled in the art.

A transformed plant cell, callus, tissue or plant may be identified and isolated by selecting or screening the engineered plant material for traits encoded by the marker genes present on the transforming DNA. For instance, selection may be performed by growing the engineered plant material on media containing inhibitory amount of the antibiotic or herbicide to which the transforming gene construct confers resistance. Further, transformed plants and plant cells may also be identified by screening for the activities of any visible marker genes (e.g., the β-glucuronidase, luciferase, B or Cl genes) that may be present on the recombinant nucleic acid constructs of the present invention. Such selection and screening methodologies are well known to those skilled in the art.

Physical and biochemical methods also may be also to identify plant or plant cell transformants containing the gene constructs of the present invention. These methods include but are not limited to: 1) Southern analysis or PCR amplification for detecting and determining the structure of the recombinant DNA insert; 2) Northern blot, S1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, immunoprecipitation, or enzyme-linked immunoassays, where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

6.10 Screening of Transformed Plants for Those with Improved Agronomic Traits

According to the present invention, to obtain plants with improved agronomic characteristics, the transformed plants may be screened for those exhibiting the desired physiological alteration. Alternatively, the transformed plants may be directly screened for those exhibiting the desired agronomic changes. A plant with the desired improvement can be isolated by screening the engineered plants for altered expression pattern or level of CCA1, GLK1 and/or bZIP1, or downstream gene products such as GLN1.3 or ASN1. A plant can also be screened for nutrient uptake, overall increased plant growth rate, enhanced vegetative yield, improved reproductive yields, increased levels of glutamine or asparagine, or increased nitrogen usage or storage. The screening of the engineered plants can involve Southern analysis to confirm the presence and number of transgene insertions; Northern analysis, RNase protection, primer extension, reverse transcriptase/PCR and the like to measure mRNA levels; measuring the amino acid composition, free amino acid pool or total nitrogen content of various plant tissues; measuring growth rates in terms of fresh weight gains over time; or measuring plant yield in terms of total dry weight and/or total seed weight, or a combination of any of the above methods. The procedures and methods for examining these parameters are well known to those skilled in the art.

In other embodiments, the screening of the transformed plants may be for improved agronomic characteristics (e.g., faster growth, greater vegetative or reproductive yields, or improved protein contents, etc.), as compared to unengineered progenitor plants, when cultivated under growth conditions (i.e., cultivated using soils or media containing or receiving sufficient amounts of nitrogen nutrients to sustain healthy plant growth).

Plants exhibiting increased growth and/or yield as compared with wild-type plants can be selected by visual observation, methods provided in the Examples, or other methods known in the art.

A "plant capable of increased yield" refers to a plant that can be induced to express its endogenous CCA1, GLK1 and/or bZIP1 gene to achieve increased yield. The term "promoter inducing amount" refers to that amount of an agent necessary to elevate such gene expression above such expression in a plant cell not contacted with the agent, by stimulating the endogenous promoter. For example, a transcription factor or a chemical agent may be used to elevate gene expression from native or chimeric CCA1, GLK1 and/or bZIP1 promoter, thus inducing the promoter and gene expression.

6.11 Cells

Optionally, germ line cells may be used in the methods described herein rather than, or in addition to, somatic cells. The term "germ line cells" refers to cells in the plant organism which can trace their eventual cell lineage to either the male or female reproductive cell of the plant. Other cells, referred to as "somatic cells" are cells which give rise to leaves, roots and vascular elements which, although important to the plant, do not directly give rise to gamete cells. Somatic cells, however, also may be used. With regard to callus and suspension cells which have somatic embryogenesis, many or most of the cells in the culture have the potential capacity to give rise to an adult plant. If the plant originates from single cells or a small number of cells from the embryogenic callus or suspension culture, the cells in the callus and suspension can therefore be referred to as germ cells. In the case of immature embryos which are prepared for treatment by the methods described herein, certain cells in the apical meristem region of the plant have been shown to produce a cell lineage which eventually gives rise to the female and male reproductive organs. With many or most species, the apical meristem is generally regarded as giving rise to the lineage that eventually will give rise to the gamete cells. An example of a non-gamete cell in an embryo would be the first leaf primordia in corn which is destined to give rise only to the first leaf and none of the reproductive structures.

6.12 Plant Regeneration

Following transformation, a plant may be regenerated, e.g., from single cells, callus tissue or leaf discs, as is standard in the art. Almost any plant can be entirely regenerated from cells, tissues, and organs of the plant. Available techniques are reviewed in Vasil et al., 1984, in Cell Culture and Somatic Cell Genetics of Plants, Vols. I, II, and III, Laboratory Procedures and Their Applications (Academic Press); and Weissbach et al., 1989, Methods For Plant Mol. Biol.

The transformed plants may then be grown, and either pollinated with the same transformed strain or different strains, and the resulting hybrid having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

Normally, a plant cell is regenerated to obtain a whole plant from the transformation process. The term "growing" or "regeneration" as used herein means growing a whole plant from a plant cell, a group of plant cells, a plant part (including seeds), or a plant piece (e.g., from a protoplast, callus, or tissue part).

Regeneration from protoplasts varies from species to species of plants, but generally a suspension of protoplasts is first made. In certain species, embryo formation can then be induced from the protoplast suspension. The culture media will generally contain various amino acids and hormones, necessary for growth and regeneration. Examples of hormones utilized include auxins and cytokinins Efficient regeneration will depend on the medium, on the genotype, and on the history of the culture. If these variables are controlled, regeneration is reproducible.

Regeneration also occurs from plant callus, explants, organs or parts. Transformation can be performed in the context of organ or plant part regeneration (see Methods in Enzymology, Vol. 118 and Klee et al., Annual Review of Plant Physiology, 38:467, 1987). Utilizing the leaf disk-transformation-regeneration method of Horsch et al., Science, 227:1229, 1985, disks are cultured on selective media, followed by shoot formation in about 2-4 weeks. Shoots that develop are excised from calli and transplanted to appropriate root-inducing selective medium. Rooted plantlets are transplanted to soil as soon as possible after roots appear. The plantlets can be repotted as required, until reaching maturity.

In vegetatively propagated crops, the mature transgenic plants are propagated by utilizing cuttings or tissue culture techniques to produce multiple identical plants. Selection of desirable transgenics is made and new varieties are obtained and propagated vegetatively for commercial use.

In seed propagated crops, mature transgenic plants can be self crossed to produce a homozygous inbred plant. The resulting inbred plant produces seed containing the newly introduced foreign gene(s). These seeds can be grown to produce plants that would produce the selected phenotype, e.g., increased lateral root growth, uptake of nutrients, overall plant growth and/or vegetative or reproductive yields.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences. Transgenic plants expressing the selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non-transgenic plant are also contemplated.

Transformed plant cells which are derived by any of the above transformation techniques can be cultured to regenerate a whole plant which possesses the transformed genotype. Such regeneration techniques often rely on manipulation of certain phytohormones in a tissue culture growth medium. For transformation and regeneration of maize see, Gordon-Kamm et al., 1990, The Plant Cell, 2:603-618.

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., 1983, Protoplasts Isolation and Culture, Handbook of Plant Cell Culture, Macmillan Publishing Company, New York, pp. 124-176; and Binding, Regeneration of Plants, Plant Protoplasts, 1985, CRC Press, Boca Raton, pp. 21-73.

The regeneration of plants containing the foreign gene introduced by *Agrobacterium* from leaf explants can be achieved as described by Horsch et al., 1985, Science, 227:1229-1231. In this procedure, transformants are grown in the presence of a selection agent and in a medium that induces the regeneration of shoots in the plant species being transformed as described by Fraley et al., 1983, Proc. Natl. Acad. Sci. (U.S.A.), 80:4803. This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

The regeneration of plants from either single plant protoplasts or various explants is well known in the art. See, for example, Methods for Plant Molecular Biology, A. Weissbach and H. Weissbach, eds., 1988, Academic Press, Inc., San Diego, Calif. This regeneration and growth process includes the steps of selection of transformant cells and shoots, rooting the transformant shoots and growth of the plantlets in soil. For maize cell culture and regeneration see generally, The Maize Handbook, Freeling and Walbot, Eds., 1994, Springer, New York 1994; Corn and Corn Improvement, 3rd edition, Sprague and Dudley Eds., 1988, American Society of Agronomy, Madison, Wis.

6.13 Plants and Plant Cells

Also provided herein are a plant cell having the nucleotide sequence constructs of the invention. A further aspect of the present invention provides a method of making such a plant cell involving introduction of a vector including the construct into a plant cell. For integration of the construct into the plant genome, such introduction will be followed by recombination between the vector and the plant cell genome to introduce the sequence of nucleotides into the genome. RNA encoded by the introduced nucleic acid construct may then be transcribed in the cell and descendants thereof, including cells in plants regenerated from transformed material. A gene stably incorporated into the genome of a plant is passed from generation to generation to descendants of the plant, so such descendants should show the desired phenotype.

In certain embodiments, a plant cell comprises a GLK1 nucleotide sequence operably associated with a vegetative tissue specific promoter, which is optionally a constitutive or inducible promoter. In other embodiments, a plant cell comprises multiple copies of a GLK1 operably associated with a vegetative tissue specific promoter. In specific embodiments provided herein are plants (and plant cells thereof) that overexpress, constitutionally express and/or inducibly express GLK1 in the vegetative tissues of the plant, as compared to other tissues in the plant and/or as compared to a wild type plant.

The present invention also provides a plant comprising a plant cell as disclosed. Transformed seeds and plant parts are also encompassed.

In addition to a plant, the present invention provides any clone of such a plant, seed, selfed or hybrid progeny and descendants, and any part of any of these, such as cuttings, seed. The invention provides any plant propagule, that is any part which may be used in reproduction or propagation, sexual or asexual, including cuttings, seed and so on. Also encompassed by the invention is a plant which is a sexually or asexually propagated off-spring, clone or descendant of such a plant, or any part or propagule of said plant, offspring, clone or descendant. Plant extracts and derivatives are also provided.

Any species of woody, ornamental or decorative, crop or cereal, fruit or vegetable plant, and algae (e.g., *Chlamydomonas reinhardtii*) may be used in the compositions and methods provided herein. Non-limiting examples of plants include plants from the genus *Arabidopsis* or the genus *Oryza*. Other examples include plants from the genuses *Acorus, Aegilops, Allium, Amborella, Antirrhinum, Apium, Arachis, Beta, Betula, Brassica, Capsicum, Ceratopteris, Citrus, Cryptomeria, Cycas, Descurainia, Eschscholzia, Eucalyptus, Glycine, Gossypium, Hedyotis, Helianthus, Hordeum, Ipomoea, Lactuca, Linum, Liriodendron, Lotus, Lupinus, Lycopersicon, Medicago, Mesembryanthemum, Nicotiana, Nuphar, Pennisetum, Persea, Phaseolus, Physcomitrella, Picea, Pinus, Poncirus, Populus, Prunus, Robinia, Rosa, Saccharum, Schedonorus, Secale, Sesamum, Solanum, Sorghum, Stevia, Thellungiella, Theobroma, Triphysaria, Triticum, Vitis, Zea,* or *Zinnia*.

Plants included in the invention are any plants amenable to transformation techniques, including gymnosperms and angiosperms, both monocotyledons and dicotyledons.

Examples of monocotyledonous angiosperms include, but are not limited to, asparagus, field and sweet corn, barley, wheat, rice, sorghum, onion, pearl millet, rye and oats and other cereal grains.

Examples of dicotyledonous angiosperms include, but are not limited to tomato, tobacco, cotton, rapeseed, field beans, soybeans, peppers, lettuce, peas, alfalfa, clover, cole crops or *Brassica oleracea* (e.g., cabbage, broccoli, cauliflower, brussel sprouts), radish, carrot, beets, eggplant, spinach, cucumber, squash, melons, cantaloupe, sunflowers and various ornamentals.

Examples of woody species include poplar, pine, *sequoia*, cedar, oak, etc.

Still other examples of plants include, but are not limited to, wheat, cauliflower, tomato, tobacco, corn, petunia, trees, etc.

In certain embodiments, plants of the present invention are crop plants (for example, cereals and pulses, maize, wheat, potatoes, tapioca, rice, sorghum, millet, cassava, barley, pea, and other root, tuber, or seed crops. Exemplary cereal crops used in the compositions and methods of the invention include, but are not limited to, any species of grass, or grain plant (e.g., barley, corn, oats, rice, wild rice, rye, wheat, millet, sorghum, triticale, etc.), non-grass plants (e.g., buckwheat flax, legumes or soybeans, etc.). Grain plants that provide seeds of interest include oil-seed plants and leguminous plants. Other seeds of interest include grain seeds, such as corn, wheat, barley, rice, sorghum, rye, etc. Oil seed plants include cotton, soybean, safflower, sunflower, *Brassica*, maize, alfalfa, palm, coconut, etc. Other important seed crops are oil-seed rape, sugar beet, maize, sunflower, soybean, and sorghum. Leguminous plants include beans and peas. Beans include guar, locust bean, fenugreek, soybean, garden beans, cowpea, mungbean, lima bean, fava bean, lentils, chickpea, etc.

Horticultural plants to which the present invention may be applied may include lettuce, endive, and vegetable brassicas including cabbage, broccoli, and cauliflower, and carnations and geraniums. The present invention may also be applied to tobacco, cucurbits, carrot, strawberry, sunflower, tomato, pepper, chrysanthemum, poplar, eucalyptus, and pine.

The present invention may be used for transformation of other plant species, including, but not limited to, corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum, Nicotiana benthamiana*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), oats, barley, *Arabidopsis* spp., vegetables, ornamentals, and conifers.

6.14 Cultivation

Methods of cultivation of plants are well known in the art. For example, for the cultivation of wheat see Alcoz et al., 1993, Agronomy Journal 85:1198-1203; Rao and Dao, 1992, J. Am. Soc. Agronomy 84:1028-1032; Howard and Lessman, 1991, Agronomy Journal 83:208-211; for the cultivation of corn see Tollenear et al., 1993, Agronomy Journal 85:251-255; Straw et al., Tennessee Farm and Home Science: Progress Report, Spring 1993, 166:20-24; Miles, S. R., 1934, J. Am. Soc. Agronomy 26:129-137; Dara et al., 1992, J. Am. Soc. Agronomy 84:1006-1010; Binford et al., 1992, Agronomy Journal 84:53-59; for the cultivation of soybean see Chen et al., 1992, Canadian Journal of Plant Science 72:1049-1056; Wallace et al., 1990, Journal of Plant Nutrition 13:1523-1537; for the cultivation of rice see Oritani and Yoshida, 1984, Japanese Journal of Crop Science 53:204-212; for the cultivation of linseed see Diepenbrock and Porksen, 1992, Industrial Crops and Products 1:165-173; for the cultivation of tomato see Grubinger et al., 1993, Journal of the American Society for Horticultural Science 118:212-216; Cerne, M., 1990, Acta Horticulture 277:179-182; for the cultivation of pineapple see Magistad et al., 1932, J. Am. Soc. Agronomy 24:610-622; Asoegwu, S. N., 1988, Fertilizer Research 15:203-210; Asoegwu, S. N., 1987, Fruits 42:505-509; for the cultivation of lettuce see Richardson and Hardgrave, 1992, Journal of the Science of Food and Agriculture 59:345-349; for the cultivation of mint see Munsi, P. S., 1992, Acta Horticulturae 306:436-443; for the cultivation of chamomile see Letchamo, W., 1992, Acta Horticulturae 306:375-384; for the cultivation of tobacco see Sisson et al., 1991, Crop Science 31:1615-1620; for the cultivation of potato see Porter and Sisson, 1991, American Potato Journal, 68:493-505; for the cultivation of *brassica* crops see Rahn et al., 1992, Conference "Proceedings, second congress of the European Society for Agronomy" Warwick Univ., p. 424-425; for the cultivation of banana see Hegde and Srinivas, 1991, Tropical Agriculture 68:331-334; Langenegger and Smith, 1988, Fruits 43:639-643; for the cultivation of strawberries see Human and Kotze, 1990, Communications in Soil Science and Plant Analysis 21:771-782; for the cultivation of sorghum see Mahalle and Seth, 1989, Indian Journal of Agricultural Sciences 59:395-397; for the cultivation of plantain see Anjorin and Obigbesan, 1985, Conference "International Cooperation for Effective Plantain and Banana Research" Proceedings of the third meeting. Abidjan, Ivory Coast, p. 115-117; for the cultivation of sugar cane see Yadav, R. L., 1986, Fertiliser News 31:17-22; Yadav and Sharma, 1983, Indian Journal of Agricultural Sciences 53:38-43; for the cultivation of sugar beet see Draycott et al., 1983, Conference "Symposium Nitrogen and Sugar Beet" International Institute for Sugar Beet Research—Brussels Belgium, p. 293-303. See also Goh and Haynes, 1986, "Nitrogen and Agronomic Practice" in Mineral Nitrogen in the Plant-Soil System, Academic Press, Inc., Orlando, Fla., p. 379-468; Engelstad, O. P., 1985, Fertilizer Technology and Use, Third Edition, Soil Science Society of America, p. 633; Yadav and Sharmna, 1983, Indian Journal of Agricultural Sciences, 53:3-43.

6.15 Products of Transgenic Plants

Engineered plants exhibiting the desired physiological and/or agronomic changes can be used directly in agricultural production.

Thus, provided herein are products derived from the transgenic plants or methods of producing transgenic plants provided herein. In certain embodiments, the products are commercial products. Some non-limiting example include genetically engineered trees for e.g., the production of pulp, paper, paper products or lumber; tobacco, e.g., for the production of cigarettes, cigars, or chewing tobacco; crops, e.g., for the production of fruits, vegetables and other food, including grains, e.g., for the production of wheat, bread, flour, rice, corn; and canola, sunflower, e.g., for the production of oils or biofuels.

In certain embodiments, commercial products are derived from a genetically engineered (e.g., comprising overexpression of GLK1 in the vegetative tissues of the plant) species of woody, ornamental or decorative, crop or cereal, fruit or vegetable plant, and algae (e.g., *Chlamydomonas reinhardtii*), which may be used in the compositions and methods provided herein. Non-limiting examples of plants include plants from the genus *Arabidopsis* or the genus *Oryza*. Other examples include plants from the genuses *Acorus, Aegilops, Allium, Amborella, Antirrhinum, Apium, Arachis, Beta, Betula, Brassica, Capsicum, Ceratopteris, Citrus, Cryptomeria, Cycas, Descurainia, Eschscholzia, Eucalyptus, Glycine, Gossypium, Hedyotis, Helianthus, Hordeum, Ipomoea, Lactuca, Linum, Liriodendron, Lotus, Lupinus, Lycopersicon, Medicago, Mesembryanthemum, Nicotiana, Nuphar, Pennisetum, Persea, Phaseolus, Physcomitrella, Picea, Pinus, Poncirus, Populus, Prunus, Robinia, Rosa, Saccharum, Schedonorus, Secale, Sesamum, Solanum, Sorghum, Stevia, Thellungiella, Theobroma, Triphysaria, Triticum, Vitis, Zea*, or *Zinnia*.

In some embodiments, commercial products are derived from a genetically engineered gymnosperms and angiosperms, both monocotyledons and dicotyledons. Examples of monocotyledonous angiosperms include, but are not limited to, asparagus, field and sweet corn, barley, wheat, rice, sorghum, onion, pearl millet, rye and oats and other cereal grains. Examples of dicotyledonous angiosperms include, but are not limited to tomato, tobacco, cotton, rapeseed, field beans, soybeans, peppers, lettuce, peas, alfalfa, clover, cole crops or *Brassica oleracea* (e.g., cabbage, broccoli, cauliflower, brussel sprouts), radish, carrot, beets, eggplant, spinach, cucumber, squash, melons, cantaloupe, sunflowers and various ornamentals.

In certain embodiments, commercial products are derived from a genetically engineered (e.g., comprising overexpression of bZIP1 in the leaves or seeds of the plant) woody species, such as poplar, pine, *sequoia*, cedar, oak, etc.

In other embodiments, commercial products are derived from a genetically engineered (e.g., comprising overexpression of CCA1 and GLK1 in the vegetative tissues of the plant) plant including, but are not limited to, wheat, cauliflower, tomato, tobacco, corn, petunia, trees, etc.

In certain embodiments, commercial products are derived from a genetically engineered crop plants, for example, cereals and pulses, maize, wheat, potatoes, tapioca, rice, sorghum, millet, cassaya, barley, pea, and other root, tuber, or seed crops. In one embodiment, commercial products are derived from a genetically engineered (e.g., comprising overexpression of CCA1 and GLK1 and underexpression of bZIP1 in the vegetative tissues of the plant) cereal crops, including, but not limited to, any species of grass, or grain plant (e.g., barley, corn, oats, rice, wild rice, rye, wheat, millet, sorghum, triticale, etc.), non-grass plants (e.g., buckwheat flax, legumes or soybeans, etc.). In another embodiments, commercial products are derived from a genetically engineered (e.g., comprising overexpression of bZIP1 and optionally underexpression of CCA1 and/or GLK1 in leaf or seed tissue of the plant) grain plants that provide seeds of interest, oil-seed plants and leguminous plants. In other embodiments, commercial products are derived from a genetically engineered grain seed plants, such as corn, wheat, barley, rice, sorghum, rye, etc. In yet other embodiments, commercial products are derived from a genetically engineered (e.g., comprising overexpression of bZIP1 and optionally underexpression of CCA1 and/or GLK1 in leaf or seed tissue of the plant) oil seed plants, such as cotton, soybean, safflower, sunflower, *Brassica*, maize, alfalfa, palm, coconut, etc. In certain embodiments, commercial products are derived from a genetically engineered oil-seed rape, sugar beet, maize, sunflower, soybean, or sorghum. In some embodiments, commercial products are derived from a genetically engineered leguminous plants, such as beans and peas (e.g., guar, locust bean, fenugreek, soybean, garden beans, cowpea, mungbean, lima bean, fava bean, lentils, chickpea, etc.)

In certain embodiments, commercial products are derived from a genetically engineered horticultural plant of the present invention, such as lettuce, endive, and vegetable brassicas including cabbage, broccoli, and cauliflower, and carnations and geraniums; tomato, tobacco, cucurbits, carrot, strawberry, sunflower, tomato, pepper, chrysanthemum, poplar, eucalyptus, and pine.

In still other embodiments, commercial products are derived from a genetically engineered corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum, Nicotiana benthamiana*), potato (*Solanum tuberosum*), peanuts (*Arachis hypogaea*), cotton (*Gossypium hirsutum*), sweet potato (*Ipomoea batatus*), cassaya (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), oats, barley, *Arabidopsis* spp., vegetables, ornamentals, and conifers.

6.16 Kits

In one aspect, the present invention provides any of the above-mentioned compositions in kits, optionally including instructions for use of the composition e.g., for the overexpression or underexpression of CCA1, GLK1 or bZIP1. The "kit" typically defines a package including one or more compositions of the invention and the instructions, and/or analogs, derivatives, or functionally equivalent compositions thereof. Thus, for example, the kit can include a description of use of the composition for participation in any technique associated in the overexpression or underexpression of genes. The kit can include a description of use of the compositions as discussed herein. Instructions also may be provided for use of the composition in any suitable technique as previously described. The instructions may be of any form provided in connection with the composition.

The kits described herein may also contain one or more containers, which may contain the inventive composition and other ingredients as previously described. The kits also may contain instructions for mixing, diluting, and/or administrating the compositions in some cases. The kits also can include other containers with one or more solvents, surfactants, preservative and/or diluents (e.g., normal saline (0.9% NaCl), or 5% dextrose) as well as containers for mixing, diluting and/or administrating the compositions.

The compositions of the kit may be provided as any suitable form, for example, as liquid solutions or as dried powders. When the composition provided is a dry powder, the composition may be reconstituted by the addition of a suitable solvent, which may also be provided. In embodiments where liquid forms of the composition are used, the liquid form may be concentrated or ready to use. The solvent will depend on the active compound(s) within the composition. Suitable solvents are well known, for example as previously described, and are available in the literature.

The invention also involves, in another aspect, promotion of the overexpression of a master regulatory gene of the present invention, e.g., CCA1/GLK1/bZIP1, according to any of the systems or methods described herein. As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention. "Instructions" can define a component of promotion, and typically involve written instructions on or associated with packaging of compositions of the invention. Instructions also can include any oral or electronic instructions provided in any manner.

7. EXAMPLE

7.1 Introduction

Nitrogen (N) is an essential nutrient and a metabolic signal that is sensed and transduced resulting in the control of gene expression in plants. Studies using nitrate reductase (NR) mutant plants, have shown that nitrate can serve as a metabolic signal for inorganic N that regulates gene expression in *Arabidopsis thaliana* and other plant species (Wang et al., 2004, Plant Physiol 136:2512-2522; Wang et al., 2003, Plant Physiol 132:556-567; Forde, 2002, Ann. Rev. Plant Biology 53:203-224; Scheible, et al., 2004, Plant Physiol 136:2483-2499). There is also ample though less direct evidence that the assimilated forms of N such as Glu or Gln may also serve as signals that regulate gene expression in plants (Rawat et al., 1999, Plant J 19:143-152; Oliveira et al., 1999, Plant Physiol 121:301-310). The ability of plants to sense and respond to levels of inorganic and organic N metabolites provides a mechanism to balance the availability of organic N resources within the plant with the need for N uptake. Because nitrate uptake, reduction and its assimilation into organic form require energy, a mechanism that activates this N assimilatory pathway based on sensing levels of organic N available in the plant is an efficient way to control N-use efficiency (Forde, 2002, Ann. Rev. Plant Biology 53:203-224). In plants, the transcription of genes involved in the uptake and assimilation of inorganic N is induced when levels of organic N are low. Conversely, the uptake and reduction of inorganic N are shut off when levels of organic N are high (reviewed in Scheible, et al., 1997, Plant Cell 9:783-798).

Recent microarray studies have shown that nitrate can cause changes in the expression of a large number of genes in *Arabidopsis* (Wang et al., 2004, Plant Physiol 136:2512-2522; Wang et al., 2003, Plant Physiol 132:556-567). Treatment of *Arabidopsis* seedlings with low levels of nitrate has been shown to increase the levels of mRNA for hundreds of genes within minutes of exposure. The nitrate-responsive genes include nitrate transporters, NR and nitrite reductase, putative transcription factors, stress responses genes, as well as genes whose products play roles in glycolysis, iron metabolism, and sulfate uptake (Wang et al., 2004, Plant Physiol 136:2512-2522; Wang et al., 2003, Plant Physiol 132:556-567). In a related study, N-starved plants underwent a transcriptome/metabolome analysis 30 min and 3 h after nitrate treatment (Scheible, et al., 2004, Plant Physiol 136:2483-2499). The expression of nitrate transporters (at 30 min) preceded the induction of amino acid biosynthetic genes and the repression of amino acid breakdown genes (at 3 h). In addition, increases in amino acid levels were observed, consistent with the changes in expression of the cognate amino acid biosynthesis genes. Putative nitrate-responsive regulatory factors including transcription factors, protein kinases/phosphatases and trehalose and hormone metabolic genes were also identified in that study. Recently, using a NR-null mutant, it was shown that nitrate and not a product of nitrate reduction and assimilation, regulates the expression of genes involved in energy production, metabolism, glycolysis and gluconeogenesis (Wang et al., 2004, Plant Physiol 136:2512-2522).

Nitrogen metabolism genes can be regulated by negative feedback of the products of N assimilation including downstream organic N metabolites such as Glu or Gln. For example, the expression of the ammonium transporter gene ammonium transporter 1 (AMT1.1) is repressed in treatments with high levels of inorganic N. It has been shown that this repression is blocked by methionine sulfoximine (MSX), a non-metabolizable analog of Glu that irreversibly inhibits glutamine synthetase and hence blocks N assimilation into Gln (Rawat et al., 1999, Plant J 19:143-152). Thus, it appears that organic forms of N may regulate the uptake of N in plants. In addition, the genes encoding asparagine synthetase 1 (ASN1) and 2 (ASN2), are differentially regulated by organic and inorganic N sources. Organic N treatments were shown to positively regulate levels of ASN1 mRNA (Oliveira et al., 1999, Plant Physiol 121:301-310), whereas ASN2 gene expression appears to be responsive to inorganic N sources and not a downstream metabolite (Wang et al., 2004, Plant Physiol 136:2512-2522). Together, these studies prompt a model in which both inorganic as well as organic N sources can each regulate plant gene expression affecting N uptake, reduction and assimilation.

In study presented below, a genomic approach was used to identify gene networks whose expression is regulated by Glu or Glu-derived metabolites (organic N) in plants. Plants were treated with inorganic nitrogen sources in the presence or absence of MSX, which served to inhibit the assimilation of ammonium into Glu/Gln by blocking glutamine synthetase. The rationale for this approach was that a subset of nitrogen-responsive genes responding specifically to an organic signal (e.g. Glu/Gln) would not respond to nitrogen treatment if the synthesis of Glu/Gln was blocked by transient MSX treatments. Network analysis of the genes that responded to organic N revealed that transcription control of gene expression is important for a subnetwork of metabolic genes involved in the synthesis and degradation of asparagine (Asn), an important nitrogen-transport/storage compound synthesized when levels of nitrogen are abundant and degraded when nitrogen reserves are mobilized. The metabolic gene network discovered in this analysis provides molecular evidence for regulation of N-use at the level of gene expression. Moreover, the transcription factors regulated by organic N associated with this network provide a mechanistic link between circadian clock function and N-assimilation in plants.

7.2 Materials and Methods

Plant growth conditions. Wild type *Arabidopsis thaliana* ecotype Columbia-0 strain was used in all experiments unless indicated otherwise. Seeds were surface sterilized with ethanol and bleach as previously described (Brenner et al., 2000, Plant Physiol. 124:1615-1624) and sowed onto basal MS salts (Sigma, St Louis, Mo.) with 0.5% (w/v) sucrose, 0.8% BactoAgar, and 1 mM $KNO_3$. After 14 days under long day (16 hours light: 8 hours dark) at 22° C., plants were transiently treated for 2 h in the light at the start of their light cycle by transferring them to basal medium with 0.5% sucrose and a combination of inorganic nitrogen sources (20 mM KNO$_3$ and 20 mM NH$_4$NO$_3$) with or without 1 mM MSX (Sigma M-5379), 10 mM glutamate (Sigma G-1501) and/or 10 mM glutamine (Sigma G-3126): N; N+MSX; N+MSX+Glu respectively.

RNA isolation and quantitative real time PCR. RNA was isolated from whole plants with the TRIzol reagent and according to the instructions of the manufacturer (InVitrogen, Carlsbad, Calif.). cDNA synthesis from whole mRNA extractions was carried out according to kit manufacturer instructions (Invitrogen, Catalog number 11146-024). Real time quantitative PCR was carried out with a LightCycler (Roche Diagnostics, Mannheim, Germany) as described previously (Thum, K. E., Shasha, D. E., Lejay, L. V. & Coruzzi, G. M. (2003) Plant Physiol 132, 440-52).

Microarray experiments and analysis. cDNA synthesis, array hybridization, and normalization of the signal intensities were performed according to the instructions provided by Affymetrix (Santa Clara, Calif.). All raw microarray data was processed with MASv5.0 software as follows. Each hybridization was normalized to a median intensity of 150. Each treatment replica was compared with the two baselines to generate 4 comparisons per treatment. Data points with absent/marginal calls (Affymetrix quality control) in both baseline and treatment were removed. Data points with absent call in one hybridization and present call in the other hybridization were eliminated if the probe called present had a signal intensity of <100. The response of each gene was summarized using the Affymetrix change calls "I" for induced, "D" for decreased and "NC" for not changed. Data points were considered only if the change calls were consistent in at least 3 out of the 4 comparisons. This stepwise filtering resulted in a set of 834 genes that were detected and responded consistently in our experiments. We used custom made S-PLUS and PERL functions to analyze and visualize groups of genes with similar expression patterns based on the Affymetrix change calls.

Network analysis. For network analysis, an existing network model of plant gene interactions was used (Gutierrez, R. A., Lejay, L. V., Dean, A., Chiaromonte, F., Shasha, D. E. & Coruzzi, G. M. (2007) Genome Biol. 8(1):R7). In addition, protein:DNA interactions were predicted based as follows: The consensus sequence for transcription binding sites from well curated databases DATF (Guo, A., He, K., Liu, D., Bai, S., Gu, X., Wei, L. & Luo, J. (2005) Bioinformatics 21, 2568-2569) and AGRIS (Davuluri, R., Sun, H., Palaniswamy, S., Matthews, N., Molina, C., Kurtz, M. & Grotewold, E. (2003) BMC Bioinformatics 4, 25) were searched in 1500 base pairs of upstream sequence using the DNA pattern search tool from the RSA tools server with default parameters (van Helden, J. (2003) Nucleic Acids Res 31, 3593-3596). The search was performed in both strands of DNA, the upstream region was not allowed to overlap with the coding region of the upstream gene, motif matches were not allowed to overlap. A motif was considered overrepresented if it was present in an upstream sequence more than 3 times the standard deviation above the mean occurrence in all the upstream sequences in the genome. A protein:DNA interaction was predicted when the upstream sequence of the gene contained an over representation of the regulatory motif for that transcription factor and the expression of the transcription factor and putative target gene was highly ($\geq 0.7$ or $\leq -0.7$) and significantly ($p \leq 0.01$) correlated. Similar regulatory predictions for other microarray data sets can be generated with the VirtualPlant system using the "Gene Networks" tool.

Chromatin immunoprecipitation assays (ChIP): Immunoprecipitations (IP) were performed as previously described (Gendrel, A., Lippman, Z., Martienssen, R. A. & Colot, V. (2005) Profiling histone modification patterns in plants using genomic tiling microarrays Nat Methods 2, 219-224). Briefly, two weeks old wild-type and CCA1-ox plants were collected at the beginning of the light cycle and immediately fixed in 1% formaldehyde for 15 min in a vacuum at room temperature. Crosslinking was stopped by the addition of glycine to a final concentration of 0.125 M. Nuclei were prepared for chromatin isolation. The isolated chromatin was sonicated ten times for 20 s each at 100% power (Diagenode Bioruptor) in an ice water bath. A small aliquot of sheared chromatin was removed to serve as control. The diluted chromatin was used for IP with the CCA1 antibody and one control IP without antibody. The primer sequences used for amplification of the CCA1 binding sites in each of the genes tested are listed in Table 1.

TABLE 1

| Gene | PUB locus | Primer 1 | Primer 2 |
|---|---|---|---|
| bZIP1 | At5g49450 | 5'-GATCGAAAATA AGGAAAGTGGG-3' (SEQ ID NO: 5) | 5'-ACTGGTCACCT ATTAAGGAAC-3' (SEQ ID NO: 6) |
| TOC1 | At5g61380 | 5'-TGGACGGTGGA GATTAAGTC-3' (SEQ ID NO: 7) | 5'-ACGAAACGAAG CCGAATCCT-3' (SEQ ID NO: 8) |
| ZTL | At5g57360 | 5'-AGTCGCCGGAGA TTATGAAGACGG-3' (SEQ ID NO: 9) | 5'-GGTTTTATCTAC TTGACCCGACAG-3' (SEQ ID NO: 10) |
| GDH1 | At5g18170 | 5'-TGTTTCAATAGC ATTAGCCTCCA-3' (SEQ ID NO: 11) | 5'-TGGGGAATGTGA CACACATAATC-3' (SEQ ID NO: 12) |
| GLN1.3 | At3g17820 | 5'-TTGAATCCGAA GAGGGAAAA-3' (SEQ ID NO: 13) | 5'-AACAACTGCTAC CAATTTCCTTG-3' (SEQ ID NO: 14) |

PCR amplifications included 95° C. for 2 min followed by 36 cycles of 95° C. for 15 s, 58° C. (for bZIP1, TOC1 and GDH1) or 60° C. (for ZTL and GLN1.3) for 30 s and 72° C. for 30 s.

Circadian phase response curves: CCA1::LUC seedlings were entrained on MS basal medium plus 0.5% sucrose and 1 mM KNO$_3$ for 8 d in 16/8 h light/dark (100-150 µmol m$^{-2}$ s$^{-1}$), after which seedlings were moved into continuous light. At 3-hr intervals, seedlings (n=16 per treatment) were transferred to fresh solid medium plus 2 mL liquid Nms or medium containing 10 mM Glu or 10 mM Gln for 4 hr, then rinsed in liquid entrainment medium 3 times for a total of 30 min and transferred individually to the wells of 96-well microtiter plates containing fresh solid media for luciferase activity measurements which were determined with a Packard TopCount scintillation counter as described (Salome, P. A., et al. (2002) The out of phase 1 mutant defines a role for PHYB in circadian phase control in *Arabidopsis* Plant Physiol 129, 1674-85). The period and phase of rhythms after the pulses were determined by fast-Fourier transform nonlinear least-square analysis (Plautz, J. D., et al. (1997) Quantitative analysis of *Drosophila* period gene transcription in living animals J Biol Rhythms 12, 204-17). The phase shifts were calculated as described (Covington, M. F., et al. (2001) ELF3 modulates resetting of the circadian clock in *Arabidopsis* Plant Cell 13, 1305-15).

7.3 Results

Inorganic versus organic N responses. To uncouple gene responses to inorganic N from those elicited by downstream products of inorganic N assimilation, treatments of *Arabidopsis* seedlings with combinations of inorganic N (nitrate and ammonium), organic forms of N (e.g., Glu, Gln), and MSX, an inhibitor of glutamine synthetase were performed (King et al., 1993, Plant Pysiol. 102:1279-1286) (FIG. 7). Genes regulated by inorganic N signals should be unaffected by MSX treatment. By contrast, genes responding to a downstream organic N signal should fail to show induction by inorganic N treatments if Glu/Gln synthesis is blocked by MSX. This block of induction by MSX should be relieved by Glu treatment. Following this rationale, two-week-old *Arabidopsis* seedlings grown on low concentrations of N (1 mM $NO_3^-$) were transferred to media containing 40 mM $NO_3^-$ and 20 mM $NH_4^+$ (referred to as "Nms"). Seedlings were then harvested after a 2 h treatment time. This treatment was carried out alone (Nms), in the presence of 1 mM MSX (Nms+MSX) or 1 mM MSX and 10 mM Glu (Nms+MSX+Glu). The Nms treatment consists of the same N source found in standard MS salts which is the established standard amount of N for plant growth (Murashige et al., 1962, Plant Physiol. 15:473-497). A concentration of 1 mM MSX has previously been established as effective in blocking the N repression of AMT1.1 in *Arabidopsis* seedlings and in decreasing levels of internal organic N (Rawat et al., 1999, Plant J 19:143-152). A concentration of 10 mM for Glu treatments was chosen because this has been shown to be effective in the regulation of N assimilatory genes while not being high enough to be detrimental to plant growth or development (Oliveria et al., 1999, Plant Physiol. 121-301-310). To evaluate the effect of MSX alone, plants were exposed to growth media that contained MSX. To control for the effect of the plant transfer to distinct media, plants were transferred onto media plates without any of the treatment factors. This latter control was used as the base line for the microarray experiments described below.

Figure 8A:
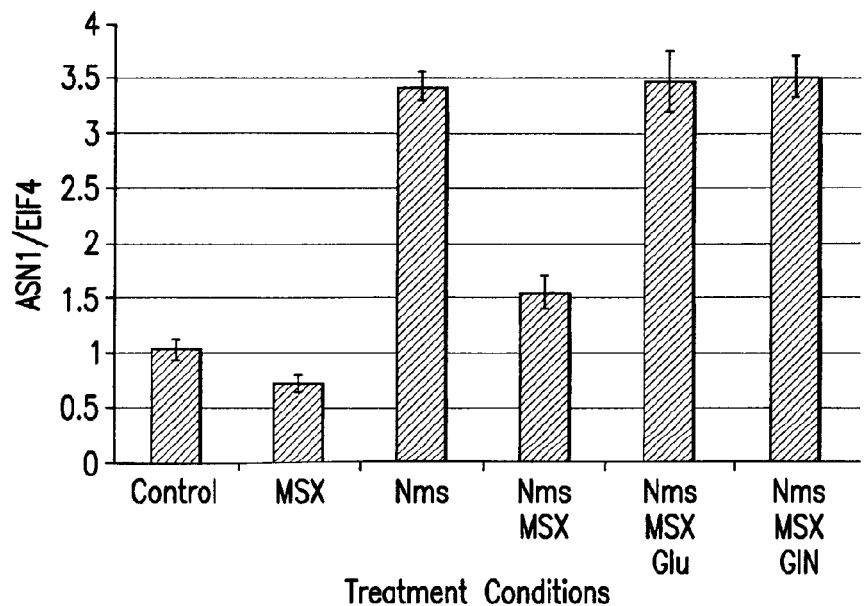
Figure 8B:
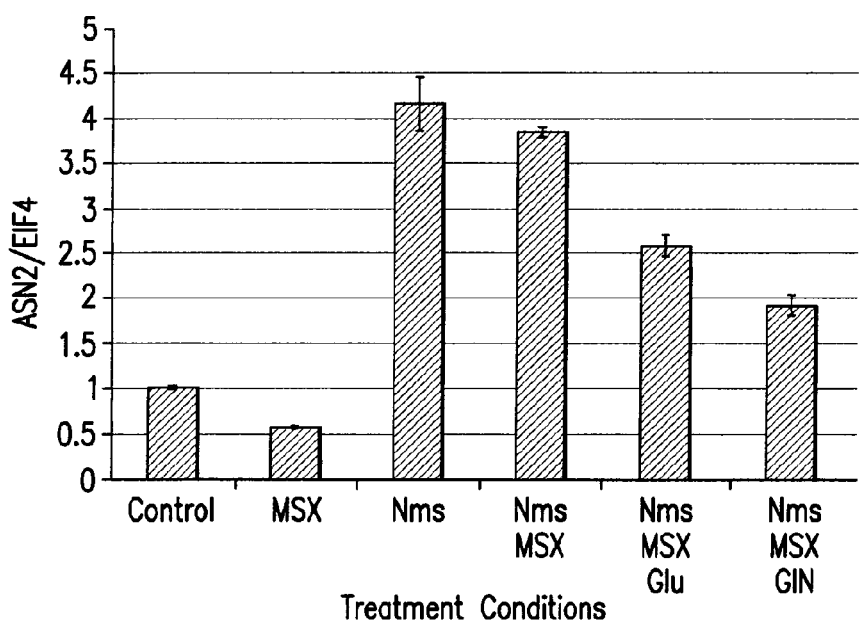

To evaluate the experimental design, the mRNA level of genes shown to be responsive to organic N (ASN1) or inorganic N (ASN2) was determined by reverse transcription followed by real time quantitative PCR (RT-qPCR). This analysis showed that the ASN1 mRNA level was induced 3.5-fold by the Nms treatment as compared to the control (FIG. 8, compare Nms versus the control). This induction of ASN1 mRNA was blocked when MSX was present (FIG. 8A, Nms+MSX versus Nms). Importantly, when exogenous Glu or Gln was added, ASN1 levels were induced regardless of the presence of MSX (FIG. 8A, compare Control to Nms+MSX+Glu and Nms+MSX+Gln). These results indicate that the induction of ASN1 is due to Glu or a downstream metabolite, as shown previously (Lam et al., 1998, Plant J 16:345-353; Oliveira et al., 2001, Braz J Med Biol Res 34:567-575). In addition, the control treatments showed that MSX alone does not induce expression of ASN1 or ASN2 (FIG. 8). The addition of Glu or Gln partially blocked the induction of ASN2 by the Nms treatment (FIG. 8B), consistent with the negative regulation by amino acids seen previously (Lam et al., 1998, Plant J 16:345-353). Conversely, the induction of ASN2 mRNA by Nms was insensitive to MSX addition (FIG. 8B), suggesting the induction was mediated by an inorganic N source. This finding was consistent with previous data which indicates that ASN2 gene expression correlates with ammonium levels (Wong et al., 2004, Plant Physiol 134:332-812).

Global genomic responses to organic and inorganic nitrogen signals. To investigate global gene expression changes that are mediated by Glu or a Glu-derived metabolite, the plant transcriptome was monitored using the ATH1 Affymetrix gene chip. Total RNA was extracted from plants treated with Nms, Nms+MSX or Nms+MSX+Glu as described above; two biological replicates per treatment were performed. The Nms+MSX+Gln treatments were not analyzed using microarrays because Gln and Glu responses were similar in our hands (FIG. 8). RNA was labeled and hybridized to the microarrays, the raw intensity values were normalized and the data filtered as described in Materials and Methods. A gene was kept in the data set only if its expression was reproducible and reliable across the 3 different treatments (Nms, Nms+MSX, Nms+MSX+Glu). A total of 5,904 genes were identified that passed these stringent quality control criteria. In order to verify the microarray results, we analyzed the mRNA levels of selected genes by RT-qPCR including the TAZ zinc binding (At4g37610) and bZIP (At5g49450) transcription factors with results similar to the microarray data (FIG. 9). As expected, the genomic experiments verified the previous observation that AMT1.1 and ASN1 are regulated by organic N. In addition, the results identified additional genes regulated by organic N as described below.

Genes were categorized based on their response to the treatments using the Affymetrix change calls: induced (I), no change (NC) or decreased (D). Each gene was assigned a three-part code (e.g. I-NC-I) which corresponds to the gene expression response in the Nms, Nms+MSX, and Nms+MSX+Glu treatments respectively. 21 unique patterns of response were found (See Annex) and Table 2 (in each column the gene listed on the left is predicted to control the expression of the gene on the right, i.e., At1g74840 is predicted to control the expression of At2g47060, At5g24800 is predicted to control the expression of At5g13930).

TABLE 2

| | | | | | |
|---|---|---|---|---|---|
| At1g74840 | reg0.9 | At2g47060 | At5g24800 | reg0.7 | At5g13930 |
| At5g14540 | reg0.9 | At5g53370 | At5g48655 | reg0.8 | At5g53370 |
| At3g61150 | reg0.7 | At4g30810 | At1g74840 | reg0.8 | At5g01820 |
| At2g46830 | reg0.8 | At5g01820 | At5g24800 | reg0.8 | At2g30040 |
| At5g48655 | reg0.7 | At2g30040 | At2g33710 | reg0.8 | At2g30040 |
| At4g17490 | reg0.8 | At2g30040 | At2g46830 | reg0.7 | At2g30040 |
| At5g44190 | reg0.8 | At2g30040 | At1g74840 | reg0.7 | At4g28100 |
| At2g20570 | reg0.8 | At4g28100 | At1g22070 | reg0.7 | At4g33300 |
| At2g46830 | reg0.7 | At1g06000 | At5g48655 | reg0.9 | At5g11790 |
| At1g74840 | reg0.8 | At4g36640 | At1g22070 | reg0.8 | At4g19810 |
| At5g24800 | reg0.9 | At4g19810 | At5g49450 | reg0.9 | At2g39980 |
| At3g01560 | reg0.7 | At2g15970 | At1g43160 | reg0.9 | At2g15970 |
| At1g22070 | reg0.7 | At2g15970 | At2g20570 | reg0.7 | At2g22240 |
| At5g49450 | reg0.8 | At1g49500 | At2g20570 | reg0.8 | At1g27730 |
| At2g46830 | reg0.9 | At1g27730 | At4g37260 | reg0.7 | At3g04070 |

TABLE 2-continued

| | | | | | |
|---|---|---|---|---|---|
| At5g24800 | reg0.8 | At2g36290 | At5g48655 | reg0.7 | At5g63790 |
| At5g48655 | reg0.7 | At4g28250 | At2g04880 | reg0.9 | At5g45340 |
| At2g25000 | reg0.7 | At5g45340 | At2g38470 | reg1.0 | At5g45340 |
| At5g44190 | reg0.8 | At1g29670 | At5g14540 | reg0.7 | At1g70330 |
| At1g53910 | reg0.7 | At1g70330 | At5g14540 | reg0.8 | At3g58560 |
| At2g22430 | reg0.8 | At2g30870 | At5g47230 | reg0.7 | At2g30870 |
| At5g61890 | reg0.7 | At2g30870 | At2g22430 | reg0.8 | At2g35930 |
| At2g38470 | reg0.7 | At1g33590 | At3g01560 | reg0.7 | At5g06320 |
| At5g14540 | reg0.7 | At5g06320 | At3g61150 | reg0.7 | At2g44210 |
| At5g49450 | reg1.0 | At2g44080 | At3g61890 | reg0.7 | At5g60850 |
| At1g22070 | reg0.7 | At3g59220 | At2g20570 | reg0.7 | At1g60780 |
| At1g43160 | reg0.7 | At1g74840 | At5g61890 | reg0.8 | At1g74840 |
| At5g49450 | reg0.9 | At4g27410 | At5g14540 | reg0.8 | At2g40270 |
| At4g37260 | reg0.7 | At1g77510 | At5g14540 | reg0.8 | At4g33400 |
| At1g74840 | reg0.7 | At4g36250 | At3g61890 | reg0.9 | At5g05600 |
| At1g74840 | reg0.9 | At1g53310 | At2g22430 | reg0.7 | At4g14960 |
| At1g43160 | reg0.9 | At5g15960 | At5g61890 | reg0.9 | At5g15960 |
| At2g22430 | reg0.8 | At3g23750 | At1g53910 | reg0.8 | At3g23750 |
| At5g61890 | reg0.8 | At3g19680 | At3g01560 | reg0.8 | At2g47180 |
| At1g43160 | reg0.7 | At2g47180 | At5g47230 | reg0.8 | At2g47180 |
| At5g61890 | reg0.7 | At2g47180 | At2g22430 | reg0.7 | At5g01540 |
| At5g14540 | reg0.7 | At2g39530 | At5g48655 | reg0.8 | At2g39530 |
| At2g33710 | reg0.8 | At2g39530 | At1g74840 | reg0.9 | At1g51680 |
| At1g22070 | reg0.8 | At4g39330 | At5g24800 | reg0.7 | At4g39330 |
| At1g53910 | reg0.9 | At4g03260 | At5g14540 | reg0.8 | At1g76670 |
| At2g22430 | reg0.7 | At1g76670 | At3g61150 | reg0.7 | At1g76670 |
| At5g24800 | reg0.9 | At5g02270 | At2g20570 | reg0.8 | At5g35735 |
| At5g61890 | reg0.8 | At3g47960 | At1g74840 | reg0.8 | At3g21230 |
| At2g04880 | reg0.8 | At4g31500 | At4g31800 | reg0.7 | At4g31500 |
| At3g61150 | reg0.8 | At5g63850 | At3g01560 | reg0.7 | At2g46600 |
| At4g37260 | reg0.9 | At1g10760 | At1g74840 | reg0.8 | At3g54640 |
| At5g49450 | reg0.7 | At1g76590 | At1g25560 | reg0.7 | At1g76590 |
| At1g68840 | reg0.8 | At1g76590 | At5g24800 | reg0.7 | At5g44190 |
| At1g74840 | reg0.9 | At5g60920 | At5g14540 | reg0.8 | At5g60920 |
| At1g25560 | reg0.8 | At4g38470 | At1g68840 | reg0.7 | At4g38470 |
| At2g20570 | reg0.8 | At2g37430 | At2g46830 | reg0.9 | At2g37430 |
| At2g04880 | reg0.8 | At2g37430 | At2g25000 | reg0.8 | At2g37430 |
| At3g30250 | reg0.7 | At2g37430 | At2g38470 | reg0.9 | At2g37430 |
| At4g01250 | reg0.7 | At2g37430 | At2g20570 | reg0.9 | At1g74460 |
| At2g46830 | reg0.8 | At1g74460 | At1g22070 | reg0.7 | At4g23630 |
| At3g01560 | reg0.9 | At3g14280 | At5g14540 | reg0.7 | At3g14280 |
| At3g61150 | reg0.7 | At3g14280 | At2g20570 | reg0.7 | At3g14280 |
| At2g46830 | reg0.8 | At3g14280 | At2g04880 | reg0.8 | At5g44070 |
| At2g38470 | reg0.9 | At5g44070 | At4g01250 | reg0.7 | At5g44070 |
| At5g24800 | reg0.7 | At1g73080 | At2g33710 | reg0.9 | At3g56710 |
| At4g17490 | reg0.9 | At3g56710 | At2g20570 | reg0.8 | At3g56710 |
| At2g46830 | reg0.8 | At3g56710 | At1g74840 | reg0.8 | At2g30490 |
| At3g01560 | reg0.7 | At2g42540 | At1g43160 | reg0.9 | At2g42540 |
| At5g61890 | reg0.8 | At2g42540 | At1g74840 | reg0.7 | At1g47128 |
| At2g46830 | reg0.7 | At1g47128 | At5g24800 | reg0.7 | At4g11280 |
| At2g20570 | reg0.7 | At3g60030 | At4g37260 | reg0.7 | At3g47620 |
| At5g49450 | reg0.8 | At3g21870 | At5g14540 | reg0.8 | At4g33050 |
| At5g48655 | reg0.7 | At4g33050 | At3g01560 | reg0.7 | At5g01600 |
| At1g43160 | reg0.8 | At5g01600 | At1g43160 | reg0.8 | At3g05890 |
| At1g74840 | reg0.7 | At2g16630 | At4g37260 | reg0.9 | At2g16630 |
| At2g04880 | reg0.9 | At5g45340 | At2g25000 | reg0.7 | At5g45340 |
| At2g38470 | reg1.0 | At5g45340 | At3g01560 | reg0.7 | At2g22880 |
| At5g48655 | reg0.7 | At2g22880 | At2g04880 | reg0.8 | At3g52400 |
| At1g43160 | reg0.9 | At1g29395 | At5g61890 | reg0.7 | At1g29395 |
| At1g74840 | reg0.8 | At2g16430 | At1g74840 | reg0.8 | At4g23210 |
| At1g22070 | reg0.7 | At4g23210 | At5g49450 | reg0.8 | At4g21150 |
| At1g22070 | reg0.9 | At3g48610 | At5g24800 | reg0.7 | At3g48610 |
| At5g47230 | reg0.7 | At2g38700 | At1g74840 | reg0.7 | At4g30280 |
| At5g14540 | reg0.7 | At1g53500 | At5g48655 | reg0.8 | At1g53500 |
| At3g01560 | reg0.7 | At2g23120 | At5g14540 | reg0.8 | At5g09440 |
| At2g22430 | reg0.8 | At5g09440 | At1g74840 | reg0.8 | At5g09440 |
| At5g24800 | reg0.7 | At2g41630 | At2g20570 | reg0.8 | At1g56150 |
| At2g46830 | reg0.8 | At1g56150 | At5g49450 | reg0.7 | At1g10070 |
| At2g22430 | reg0.8 | At3g21240 | At3g01560 | reg0.8 | At5g16010 |
| At4g37260 | reg0.9 | At5g46710 | At1g25560 | reg0.7 | At5g11420 |
| At1g68840 | reg0.7 | At5g11420 | At5g24800 | reg0.7 | At4g01250 |
| At5g44190 | reg0.7 | At3g07790 | At2g30250 | reg0.7 | At1g13110 |
| At2g38470 | reg0.8 | At1g13110 | At4g01250 | reg0.9 | At1g13110 |
| At1g22070 | reg0.8 | At2g25000 | At2g20570 | reg0.9 | At2g25000 |
| At2g46830 | reg0.8 | At2g25000 | At2g04880 | reg0.8 | At2g25000 |
| At2g38470 | reg0.7 | At2g25000 | At4g31800 | reg0.8 | At2g25000 |
| At5g24800 | reg0.7 | At1g35780 | At3g01560 | reg0.8 | At5g11110 |
| At1g74840 | reg0.9 | At5g11110 | At1g43160 | reg0.8 | At5g11110 |
| At5g47230 | reg0.7 | At5g11110 | At5g61890 | reg0.7 | At5g11110 |
| At3g61890 | reg0.8 | At4g12490 | At1g74840 | reg0.7 | At1g51700 |

TABLE 2-continued

| | | | | | |
|---|---|---|---|---|---|
| At1g74840 | reg0.8 | At3g55970 | At4g37260 | reg0.7 | At3g55970 |
| At4g17500 | reg0.8 | At5g49910 | At1g22070 | reg0.7 | At4g39800 |
| At1g74840 | reg0.8 | At4g39800 | At2g20570 | reg0.7 | At4g39800 |
| At2g46830 | reg0.8 | At4g39800 | At2g20570 | reg0.8 | At2g13790 |
| At2g46830 | reg0.8 | At2g13790 | At3g61890 | reg1.0 | At1g52400 |
| At2g20570 | reg0.8 | At5g18470 | At2g46830 | reg0.7 | At5g18470 |
| At2g22430 | reg0.9 | At1g53910 | At5g14540 | reg0.9 | At2g40140 |
| At5g48655 | reg0.9 | At2g40140 | At2g20570 | reg0.8 | At2g40890 |
| At2g46830 | reg0.8 | At2g40890 | At1g74840 | reg0.7 | At3g55070 |
| At4g37260 | reg0.7 | At1g68520 | At1g74840 | reg0.9 | At1g14780 |
| At1g43160 | reg0.8 | At1g14780 | At5g61890 | reg0.9 | At1g14780 |
| At2g22430 | reg0.9 | At2g39210 | At2g20570 | reg0.9 | At1g76600 |
| At2g46830 | reg0.9 | At1g76600 | At2g04880 | reg0.9 | At1g76600 |
| At2g25000 | reg0.8 | At1g76600 | At2g38470 | reg0.8 | At1g76600 |
| At5g48655 | reg0.8 | At5g19240 | At2g22430 | reg0.7 | At3g02910 |
| At2g22430 | reg0.9 | At3g63010 | At3g61890 | reg0.9 | At3g49120 |
| At1g74840 | reg0.7 | At3g49120 | At4g37260 | reg0.8 | At3g49120 |
| At5g14540 | reg0.7 | At3g52450 | At2g23320 | reg0.7 | At3g52450 |
| At4g31800 | reg0.9 | At3g52450 | At1g25560 | reg0.7 | At5g58710 |
| At1g68840 | reg0.7 | At5g58710 | At5g49450 | reg0.7 | At5g58710 |
| At3g01560 | reg0.8 | At4g25650 | At1g53910 | reg0.7 | At4g04020 |
| At4g17490 | reg0.7 | At4g04020 | At5g49450 | reg0.9 | At3g47340 |
| At5g49450 | reg0.8 | At1g77120 | At5g48655 | reg0.7 | At2g26190 |
| At4g37260 | reg0.7 | At5g49450 | At1g22070 | reg0.9 | At1g20440 |
| At1g22070 | reg0.7 | At5g59820 | At5g48655 | reg0.8 | At1g26250 |
| At1g74840 | reg0.8 | At5g07010 | At4g37260 | reg0.7 | At5g07010 |
| At1g74840 | reg0.7 | At3g54690 | At2g20570 | reg0.7 | At3g54690 |
| At2g46830 | reg0.8 | At3g54690 | At2g20570 | reg0.8 | At5g26920 |
| At2g46830 | reg0.7 | At5g26920 | At3g61890 | reg0.8 | At2g02990 |
| At1g74840 | reg0.8 | At5g61890 | At5g49450 | reg0.7 | At2g34500 |
| At1g74840 | reg0.8 | At4g01700 | At2g46830 | reg0.7 | At4g01700 |
| At2g20570 | reg0.9 | At5g59730 | At2g46830 | reg0.9 | At5g59730 |
| At3g01560 | reg0.8 | At3g52470 | At5g14540 | reg0.8 | At3g52470 |
| At5g48655 | reg0.7 | At3g52470 | At2g46830 | reg0.8 | At3g02800 |
| At5g49450 | reg0.8 | At4g24800 | At4g37260 | reg0.7 | At4g24800 |
| At2g20570 | reg0.8 | At5g25630 | At2g46830 | reg0.7 | At5g25630 |
| At5g24800 | reg0.7 | At5g28900 | At2g20570 | reg0.7 | At4g27280 |
| At2g46830 | reg0.8 | At4g27280 | At5g49450 | reg0.9 | At3g13450 |
| At5g24800 | reg0.9 | At1g20510 | At2g20570 | reg0.7 | At1g20510 |
| At2g46830 | reg0.8 | At1g20510 | At5g44190 | reg0.7 | At1g20510 |
| At2g46830 | reg0.7 | At1g14730 | At5g61890 | reg0.7 | At1g43160 |
| At3g01560 | reg0.8 | At5g06700 | At5g14540 | reg0.8 | At5g06700 |
| At1g22070 | reg0.7 | At5g06700 | 1g74840 | reg0.8 | At5g06700 |
| At2g20570 | reg0.7 | At5g06700 | 5g24800 | reg0.7 | At4g34450 |
| At1g43160 | reg1.0 | At2g28900 | At1g74840 | reg0.7 | At2g28900 |
| At4g37260 | reg0.7 | At2g28900 | 2g20570 | reg0.7 | At5g42310 |
| At3g01560 | reg0.8 | At5g42310 | At5g14540 | reg0.8 | At5g42310 |
| At3g01560 | reg0.7 | At2g43620 | At3g61890 | reg0.8 | At2g43620 |
| At1g74840 | reg0.7 | At3g23810 | At2g20570 | reg0.8 | At3g17820 |
| At2g46830 | reg0.7 | At3g17820 | At3g01560 | reg0.8 | At3g23820 |
| At5g14540 | reg0.7 | At3g23820 | At1g74840 | reg0.8 | At3g23820 |
| At1g43160 | reg0.7 | At3g23820 | At5g47230 | reg0.8 | At3g23820 |
| At5g61890 | reg0.8 | At3g23820 | At5g49450 | reg0.9 | At3g57520 |
| At3g61890 | reg0.9 | At4g22212 | At2g30250 | reg0.7 | At2g46225 |
| At4g01250 | reg0.7 | At2g46225 | At4g23810 | reg0.8 | At2g46225 |
| At5g49450 | reg0.7 | At4g37260 | At5g24800 | reg0.7 | At2g24940 |
| At1g25560 | reg0.9 | At3g19390 | At1g68840 | reg0.9 | At3g19390 |
| At3g01560 | reg0.8 | At1g21790 | At1g74840 | reg0.8 | At1g21790 |
| At4g37260 | reg0.8 | At1g21790 | At4g37260 | reg0.7 | At1g12780 |
| At2g20570 | reg0.7 | At5g54490 | At2g46830 | reg0.9 | At5g54490 |
| At1g22070 | reg0.9 | At3g11670 | At5g24800 | reg0.7 | At3g11670 |
| At5g49450 | reg-0.7 | At2g30040 | At1g25560 | reg-0.7 | At2g30040 |
| At1g68840 | reg-0.7 | At2g30040 | At2g20570 | reg-0.9 | At1g80180 |
| At2g46830 | reg-0.8 | At1g80180 | At1g22070 | reg-0.7 | At1g06760 |
| At5g24800 | reg-0.8 | At5g61790 | At5g48655 | reg-0.7 | At1g11545 |
| At2g20570 | reg-0.8 | At1g07040 | At2g46830 | reg-0.8 | At1g07040 |
| At4g17500 | reg-0.7 | At2g15970 | At2g22430 | reg-0.9 | At1g49500 |
| At5g44190 | reg-0.7 | At3g04070 | At4g37260 | reg-0.8 | At4g22710 |
| At5g49450 | reg-0.8 | At5g63790 | At5g14540 | reg-0.7 | At3g60320 |
| At5g48655 | reg-0.9 | At3g60320 | At2g22430 | reg-0.7 | At3g60320 |
| At3g01560 | reg-0.7 | At4g37450 | At4g37260 | reg-0.7 | At1g77450 |
| At1g22070 | reg-0.7 | At1g42480 | At2g46830 | reg-0.7 | At5g64570 |
| At2g20570 | reg-0.8 | At5g39610 | At2g22430 | reg-0.8 | At5g39610 |
| At3g61890 | reg-0.7 | At2g34640 | At5g24800 | reg-0.8 | At4g16660 |
| At2g20570 | reg-0.7 | At5g60680 | At2g46830 | reg-0.7 | At5g60680 |
| At4g17500 | reg-0.7 | At2g47180 | At1g22070 | reg-0.9 | At1g09210 |
| At2g04880 | reg-0.7 | At1g68840 | At2g38470 | reg-0.8 | At1g68840 |
| At2g22430 | reg-0.7 | At1g49860 | At5g44190 | reg-0.8 | At1g09240 |
| At1g74840 | reg-0.7 | At1g76690 | At4g37260 | reg-0.9 | At1g76690 |
| At1g43160 | reg-0.9 | At4g31130 | At5g61890 | reg-0.7 | At4g31130 |

TABLE 2-continued

| | | | | | |
|---|---|---|---|---|---|
| At1g74840 | reg-0.7 | At4g31130 | At4g37260 | reg-0.8 | At4g31130 |
| At5g49450 | reg-0.9 | At2g38470 | At5g44190 | reg-0.7 | At4g39980 |
| At5g14540 | reg-0.9 | At4g12600 | At4g37260 | reg-0.8 | At3g25230 |
| At1g74840 | reg-0.8 | At1g32170 | At2g20570 | reg-0.7 | At1g32170 |
| At2g46830 | reg-0.7 | At1g32170 | At1g43160 | reg-0.7 | At2g29490 |
| At5g47230 | reg-0.7 | At2g29490 | At5g61890 | reg-0.8 | At2g29490 |
| At5g14540 | reg-0.8 | At5g05440 | At5g48655 | reg-0.8 | At5g05440 |
| At2g33710 | reg-0.8 | At4g39675 | At2g20570 | reg-0.7 | At2g04280 |
| At2g46830 | reg-0.7 | At2g04280 | At1g74840 | reg-0.7 | At5g49480 |
| At2g22430 | reg-0.7 | At5g49480 | At3g61150 | reg-0.7 | At5g49480 |
| At5g48655 | reg-0.7 | At1g76590 | At4g37260 | reg-0.7 | At1g32920 |
| At2g33710 | reg-0.9 | At4g38470 | At4g17490 | reg-0.8 | At4g38470 |
| At2g20570 | reg-0.7 | At4g38470 | At2g46830 | reg-0.8 | At4g38470 |
| At5g44190 | reg-0.7 | At5g15410 | At2g20570 | reg-0.7 | At1g67910 |
| At2g46830 | reg-0.8 | At1g67910 | At3g01560 | reg-0.7 | At5g25460 |
| At5g14540 | reg-0.9 | At5g25460 | At5g48655 | reg-0.8 | At5g25460 |
| At3g61150 | reg-0.7 | At3g48990 | At1g22070 | reg-0.8 | At3g48990 |
| At5g24800 | reg-0.8 | At3g48990 | At5g49450 | reg-0.7 | At3g62960 |
| At1g25560 | reg-0.8 | At3g56710 | At1g68840 | reg-0.7 | At3g56710 |
| At5g44190 | reg-0.7 | At3g51550 | At1g74840 | reg-0.8 | At3g62120 |
| At4g17500 | reg-0.7 | At2g42540 | At5g49450 | reg-0.8 | At4g11280 |
| At1g22070 | reg-0.8 | At3g15950 | At3g01560 | reg-0.9 | At3g19130 |
| At1g74840 | reg-0.7 | At4g21620 | At4g37260 | reg-0.8 | At4g21620 |
| At5g14540 | reg-0.7 | At3g21870 | At5g48655 | reg-0.7 | At3g21870 |
| At2g20570 | reg-0.8 | At3g15450 | At2g46830 | reg-0.8 | At3g15450 |
| At4g17500 | reg-0.7 | At5g01600 | At4g17500 | reg-0.7 | At3g05890 |
| At2g46830 | reg-0.8 | At1g22570 | At5g48655 | reg-0.9 | At3g14310 |
| At3g61150 | reg-0.8 | At5g65390 | At2g20570 | reg-0.8 | At1g76160 |
| At2g46830 | reg-0.7 | At1g76160 | At4g17500 | reg-0.7 | At1g29395 |
| At5g49450 | reg-0.7 | At5g66510 | At1g74840 | reg-0.7 | At1g62480 |
| At5g44190 | reg-0.8 | At3g07390 | At2g20570 | reg-0.8 | At2g33830 |
| At2g46830 | reg-0.8 | At2g33830 | At3g61890 | reg-0.7 | At3g06680 |
| At4g37260 | reg-0.7 | At5g23020 | At5g24800 | reg-0.7 | At1g10070 |
| At5g48655 | reg-0.8 | At4g36670 | At2g38470 | reg-0.9 | At4g36670 |
| At1g22070 | reg-0.7 | At2g44310 | At5g24800 | reg-0.7 | At2g44310 |
| At2g22430 | reg-0.7 | At2g44310 | At3g61150 | reg-0.7 | At2g44310 |
| At3g01560 | reg-0.7 | At4g12880 | At5g14540 | reg-0.8 | At4g12880 |
| At5g48655 | reg-0.9 | At4g12880 | At1g74840 | reg-0.8 | At4g13770 |
| At4g37260 | reg-0.7 | At4g13770 | At3g61150 | reg-0.7 | At3g54400 |
| At5g44190 | reg-0.7 | At5g06530 | At5g48655 | reg-0.9 | At5g11420 |
| At2g33710 | reg-0.9 | At5g11420 | At4g17490 | reg-0.8 | At5g11420 |
| At1g74840 | reg-0.7 | At1g19870 | At4g37260 | reg-0.7 | At1g19870 |
| At1g22070 | reg-0.8 | At1g19870 | At4g17500 | reg-0.7 | At1g35780 |
| At4g17500 | reg-0.7 | At5g11110 | At5g49450 | reg-0.9 | At1g10960 |
| At5g44190 | reg-0.7 | At5g06530 | At5g44190 | reg-0.7 | At3g55970 |
| At4g37260 | reg-0.8 | At3g11700 | At3g01560 | reg-0.7 | At5g49910 |
| At3g61890 | reg-0.8 | At4g23180 | At1g74840 | reg-0.9 | At4g23180 |
| At4g37260 | reg-0.7 | At4g23180 | At1g74840 | reg-0.8 | At4g10480 |
| At2g46830 | reg-0.7 | At4g10480 | At2g22430 | reg-0.7 | At5g43970 |
| At3g61150 | reg-0.7 | At5g43970 | At3g61890 | reg-0.7 | At5g11670 |
| At1g22070 | reg-0.7 | At1g56330 | At5g48655 | reg-0.7 | At1g68520 |
| At5g44190 | reg-0.7 | At1g68520 | At3g61150 | reg-0.7 | At1g31420 |
| At5g44190 | reg-1.0 | At2g23810 | At2g20570 | reg-0.9 | At3g15630 |
| At2g46830 | reg-0.8 | At3g15630 | At2g20570 | reg-0.9 | At2g39570 |
| At2g46830 | reg-0.8 | At2g39570 | At5g49450 | reg-0.8 | At1g76600 |
| At1g74840 | reg-0.9 | At2g06850 | At5g14540 | reg-0.7 | At2g37640 |
| At5g48655 | reg-0.7 | At2g37640 | At2g20570 | reg-0.8 | At2g37640 |
| At2g46830 | reg-0.9 | At2g37640 | At1g74840 | reg-0.7 | At1g02930 |
| At4g37260 | reg-0.7 | At1g02930 | At2g33710 | reg-0.8 | At5g58710 |
| At3g61890 | reg-0.7 | At1g64640 | At1g74840 | reg-0.8 | At1g64640 |
| At2g20570 | reg-0.8 | At3g49780 | At2g46830 | reg-0.9 | At3g49780 |
| At5g24800 | reg-0.8 | At3g49780 | At5g24800 | reg-0.7 | At3g47340 |
| At5g44190 | reg-0.8 | At1g09330 | At5g48655 | reg-0.7 | At5g49450 |
| At2g20570 | reg-0.8 | At5g49450 | At2g46830 | reg-0.7 | At5g49450 |
| At5g44190 | reg-0.8 | At5g07010 | At5g49450 | reg-0.7 | At2g29550 |
| At1g22070 | reg-0.7 | At2g34500 | At1g74840 | reg-0.8 | At3g61440 |
| At5g14540 | reg-0.8 | At2g24500 | At5g24800 | reg-0.7 | At5g11520 |
| At4g37260 | reg-0.7 | At1g62380 | At5g48655 | reg-0.7 | At1g80070 |
| At2g22430 | reg-0.8 | At3g13450 | At5g14540 | reg-0.8 | At1g24530 |
| At1g22070 | reg-0.7 | At1g24530 | At5g49450 | reg-0.7 | At1g20510 |
| At5g14540 | reg-0.7 | At1g73120 | At4g17500 | reg-0.7 | At1g43160 |
| At1g74840 | reg-0.9 | At1g53240 | At2g20570 | reg-0.8 | At5g18170 |
| At2g46830 | reg-0.8 | At5g18170 | At3g61890 | reg-0.8 | At2g30010 |
| At1g74840 | reg-0.7 | At2g30010 | At4g37260 | reg-0.9 | At2g30010 |
| At5g49450 | reg-0.8 | At2g30010 | At5g24800 | reg-0.9 | At5g49700 |
| At4g17500 | reg-0.8 | At2g28900 | At5g24800 | reg-0.8 | At1g15690 |
| At5g44190 | reg-0.8 | At4g12480 | At2g04880 | reg-0.9 | At5g22920 |
| At2g25000 | reg-0.7 | At5g22920 | At2g38470 | reg-1.0 | At5g22920 |
| At5g44190 | reg-0.8 | At3g23810 | At5g48655 | reg-0.8 | At3g57520 |
| At2g20570 | reg-0.7 | At3g57520 | At2g46830 | reg-0.8 | At3g57520 |

TABLE 2-continued

| At5g24800 | reg-0.7 | At3g57520 | At1g53910 | reg-0.8 | At5g04340 |
| At5g24800 | reg-0.8 | At2g05380 | At2g33710 | reg-0.7 | At3g19390 |
| At4g17490 | reg-0.8 | At3g19390 | At4g37260 | reg-0.8 | At3g12740 |
| At2g20570 | reg-0.7 | At1g12780 | At3g61890 | reg-0.8 | At3g16530 |

The largest pattern was NC-NC-NC, representing 5,070 genes not affected by the treatments. The remainder 20 patterns (834 genes) were grouped into six classes that summarize the types of N-responses observed: (A) inorganic N, (B) inorganic N with Glu feedback, (C) organic N with no exogenous Glu rescue, (D) exogenous Glu, (E) exogenous and endogenous Glu and (F) exogenous and endogenous Glu with opposite effects (Table 3).

TABLE 3

| | | Treatment | | | |
|---|---|---|---|---|---|
| Response | Nms | Nms + MSX | Nms + MSX + Glu | Genes | Genes per class |
| A) Inorganic nitrogen | D | D | D | 100 | 159 |
| | I | I | I | 59 | |
| B) Inorganic nitrogen and Glu | D | D | NC | 30 | 48 |
| | I | I | NC | 15 | |
| | D | D | I | 3 | |
| C) Internal Glu | D | NC | NC | 194 | 334 |
| | I | NC | NC | 56 | |
| | NC | I | I | 49 | |
| | NC | D | D | 33 | |
| | D | I | I | 2 | |
| D) External Glu | NC | NC | D | 89 | 126 |
| | NC | NC | I | 37 | |
| E) Internal/External Glu | NC | I | NC | 55 | 164 |
| | NC | D | NC | 36 | |
| | D | NC | D | 47 | |
| | I | NC | I | 22 | |
| F) Opposite Internal/External Glu | I | D | I | 3 | 3 |
| | NC | D | I | 1 | |
| | D | NC | I | 2 | |
| | I | NC | D | 1 | |
| | | | | 834 | |

Nitrogen responses. Patterns of expression based on their response to the Nms, Nms + MSX and Nms + MSX + Glu treatments. D = decreased; I = increased; NC = not changed. Genes were categorized into six classes based on these patterns.

The genes regulated in the experiments were compared to published results (Wang et al., 2004, Plant Physiol 136: 2512-2522). This previous study identified 595 genes that responded similarly to nitrate treatment in both a NR-null mutant and wild-type plants. Because the mutant plants cannot assimilate nitrate, the responses observed were attributed to the action of nitrate as a signal and not a downstream metabolite. 80 out of these 595 genes showed consistent and reliable responses in the current experiments. Surprisingly, only 17 of these genes were found regulated by inorganic N signals in both studies (Table 4). Among these, we found nitrite reductase and several high affinity nitrate transporters. The majority, 58 of these 80 genes (73%), belonged to the C, D or E classes in the present studies suggesting that many previously described nitrate-responsive genes may respond to organic N signals (Table 4).

TABLE 4

| Regulated by | PUB LOCUS | Gene Name |
|---|---|---|
| Inorganic N | At4g19170 | 9-cis-epoxycarotenoid dioxygenase, putative/neoxanthin cleavage enzyme, putative/carotenoid cleavage dioxygenase, putative similar to 9-cis-epoxycarotenoid dioxygenase [Phaseolus vulgaris][GI:6715257]; neoxanthin cleavage enzyme, Lycopersicon esculentum, PATX:E325797 (68417.m02829) |
| Inorganic N | At3g61820 | aspartyl protease family protein contains Pfam domain, PF00026: eukaryotic aspartyl protease (68416.m06939) |
| Inorganic N | At4g30190 | ATPase 2, plasma membrane-type, putative/proton pump 2, putative/proton-exporting ATPase, putative strong similarity to SP |
| Inorganic N | At4g31500 | cytochrome P450 83B1 (CYP83B1) Identical to Cytochrome P450 (SP:O65782)[Arabidopsis thaliana] (68417.m04474) |
| Inorganic N | At1g05340 | expressed protein (68414.m00541) |
| Inorganic N | At1g19020 | expressed protein (68414.m02367) |
| Inorganic N | At1g32920 | expressed protein (68414.m04055) |
| Inorganic N | At2g41730 | expressed protein (68415.m05158) |
| Inorganic N | At1g14870 | expressed protein similar to PGPS/D12 [Petunia x hybrida] GI:4105794; contains Pfam profile PF04749: Protein of unknown function, DUF614 (68414.m01778) |
| Inorganic N | At5g25350 | F-box family protein contains Pfam PF00646: F-box domain and Pfam PF00560: Leucine Rich Repeat (6 copies); similar to F-box protein FBL6 (GI:4432860) [Homo sapiens] (68418.m03007) |
| Inorganic N | At2g15620 | ferredoxin--nitrite reductase, putative strong similarity to ferredoxin--nitrite reductase [Nicotiana tabacum] GI:19893; contains Pfam profiles PF03460: Nitrite/Sulfite reductase ferredoxin-like half domain, PF01077: Nitrite and sulphite reductase 4Fe—4S domain (68415.m01789) |
| Inorganic N | At5g55050 | GDSL-motif lipase/hydrolase family protein similar to family II lipases EXL3 GI:15054386, EXL1 GI:15054382, EXL2 GI:15054384 from [Arabidopsis thaliana]; contains Pfam profile PF00657: GDSL-like Lipase/Acylhydrolase (68418.m06861) |
| Inorganic N | At5g18600 | glutaredoxin family protein contains glutaredoxin domain, INTERPRO:IPR002109 (68418.m02201) |

TABLE 4-continued

| Regulated by | PUB LOCUS | Gene Name |
|---|---|---|
| Inorganic N | At1g49860 | glutathione S-transferase, putative similar to GI:860955 from [*Hyoscyamus muticus*] (Plant Physiol. 109 (1), 253-260 (1995)) (68414.m05590) |
| Inorganic N | At1g08090 | high-affinity nitrate transporter (ACH1) identical to trans-membrane nitrate transporter protein AtNRT2:1 [*Arabidopsis thaliana*] GI:3747058, high-affinity nitrate transporter ACH1 [*Arabidopsis thaliana*] GI:3608362 (68414.m00885) |
| Inorganic N | At1g12940 | high-affinity nitrate transporter, putative similar to trans-membrane nitrate transporter protein AtNRT2:1 [*Arabidopsis thaliana*] GI:3747058, high-affinity nitrate transporter ACH1 [*Arabidopsis thaliana*] GI:3608362 (68414.m01503) |
| Inorganic N | At1g12110 | nitrate/chlorate transporter (NRT1.1) (CHL1) identical to nitrate/chlorate transporter SP:Q05085 from [*Arabidopsis thaliana*]; contains Pfam profile: PF00854 POT family (68414.m01402) |
| Organic and Inorganic N | At1g55920 | serine O-acetyltransferase, putative identical to GI:608677 from [*Arabidopsis thaliana*] (68414.m06414) |
| Organic and Inorganic N | At2g16660 | nodulin family protein similar to nodulin-like protein [*Arabidopsis thaliana*] GI:3329368, nodule-specific protein Nlj70 [*Lotus japonicus*] GI:3329366 (68415.m01912) |
| Organic and Inorganic N | At3g45140 | lipoxygenase (LOX2) identical to SP |
| Organic and Inorganic N | At5g64410 | oligopeptide transporter OPT family protein similar to SP |
| Organic and Inorganic N | At5g65010 | asparagine synthetase 2 (ASN2) identical to asparagine synthetase (ASN2) [*Arabidopsis thaliana*] GI:3859536 (68418.m08178) |
| Organic N | At1g14780 | expressed protein (68414.m01767) |
| Organic N | At1g22160 | senescence-associated protein-related similar to senescence-associated protein SAG102 (GI:22331931) [*Arabidopsis thaliana*] (68414.m02770) |
| Organic N | At1g31770 | ABC transporter family protein contains Pfam profile: PF00005: ABC transporter (68414.m03899) |
| Organic N | At1g32450 | proton-dependent oligopeptide transport (POT) family protein contains Pfam profile: PF00854 POT family (68414.m04005) |
| Organic N | At1g47128 | cysteine proteinase (RD21A)/thiol protease identical to SP |
| Organic N | At1g49500 | expressed protein (68414.m05548) |
| Organic N | At1g56150 | auxin-responsive family protein similar to SP:P33082 Auxin-induced protein X15. [Soybean] {*Glycine max*} (68414.m06450) |
| Organic N | At1g67910 | expressed protein (68414.m07755) |
| Organic N | At1g74090 | sulfotransferase family protein similar to SP |
| Organic N | At1g74710 | isochorismate synthase 1 (ICS1)/isochorismate mutase identical to GI:17223087 and GB:AF078080; contains Pfam profile PF00425: chorismate binding enzyme; contains TIGRfam profile TIGR00543: isochorismate synthases; identical to cDNA isochorismate synthase 1 precursor (ICS1) nuclear gene for plastid product GI:17223086 (68414.m08655) |
| Organic N | At1g77760 | nitrate reductase 1 (NR1) identical to SP |
| Organic N | At1g78000 | sulfate transporter (Sultr1; 2) identical to sulfate transporter Sultr1; 2 [*Arabidopsis thaliana*] GI:7768660; contaisn Pfam profiles PF00916: Sulfate transporter family and PF01740: STAS domain; contains TIGRfam profile TIGR00815: sulfate permease (68414.m09090) |
| Organic N | At2g15970 | cold-acclimation protein, putative (FL3-5A3) similar to cold acclimation WCOR413-like protein gamma form [*Hordeum vulgare*] gi |
| Organic N | At2g27830 | expressed protein (68415.m03374) |
| Organic N | At2g28550 | AP2 domain-containing transcription factor RAP2.7 (RAP2.7) nearly identical to AP2 domain transcription factor RAP2.7 (GI:2281639) [*Arabidopsis thaliana*] (68415.m03469) |
| Organic N | At2g30040 | protein kinase family protein contains protein kinase domain, Pfam: PF00069 (68415.m03653) |
| Organic N | At2g31790 | UDP-glucoronosyl/UDP-glucosyl transferase family protein contains Pfam profile: PF00201 UDP-glucoronosyl and UDP-glucosyl transferase (68415.m03881) |
| Organic N | At2g33710 | AP2 domain-containing transcription factor family protein similar to RAP2.6 (GI:17065542) {*Arabidopsis thaliana*} (68415.m04132) |
| Organic N | At2g33830 | dormancy/auxin associated family protein contains Pfam profile: PF05564 dormancy/auxin associated protein (68415.m04151) |
| Organic N | At2g35930 | U-box domain-containing protein similar to immediate-early fungal elicitor protein CMPG1 [*Petroselinum crispum*] GI:14582200; contains Pfam profile PF04564: U-box domain (68415.m04410) |
| Organic N | At2g39200 | seven transmembrane MLO family protein/MLO-like protein 12 (MLO12) identical to SP |
| Organic N | At2g39570 | ACT domain-containing protein contains Pfam ACT domain PF01842 (68415.m04854) |
| Organic N | At2g40140 | zinc finger (CCCH-type) family protein contains Pfam domain, PF00642: Zinc finger C-x8-C-x5-C-x3-H type (and similar) and Pfam domain, PF00023: Ankyrin repeat (68415.m04937) |
| Organic N | At2g43100 | aconitase C-terminal domain-containing protein contains Pfam profile PF00694: Aconitase C-terminal domain (68415.m05350) |
| Organic N | At3g02910 | expressed protein contains Pfam domain PF03674: Uncharacterised protein family (UPF0131) (68416.m00286) |

TABLE 4-continued

| Regulated by | PUB LOCUS | Gene Name |
|---|---|---|
| | | zinc finger (C3HC4-type RING finger) family protein (ATL6) contains Pfam profile: PF00097: Zinc finger, C3HC4 type (RING finger) |
| Organic N | At3g05200 | (68416.m00567) |
| Organic N | At3g10520 | non-symbiotic hemoglobin 2 (HB2) (GLB2) identical to SP dihydrolipoamide S-acetyltransferase, putative similar to dihydrolipoamide S-acetyltransferase [Zea mays] GI:5669871; contains Pfam profiles PF00198: 2-oxo acid dehydrogenases acyltransferase (catalytic domain), PF00364: Biotin-requiring enzyme, PF02817: e3 binding domain |
| Organic N | At3g13930 | (68416.m01759) |
| Organic N | At3g14940 | phosphoenolpyruvate carboxylase, putative/PEP carboxylase, putative strong similarity to SP |
| Organic N | At3g15630 | expressed protein (68416.m01982) |
| | | malate dehydrogenase [NAD], chloroplast (MDH) identical to chloroplast NAD-malate dehydrogenase [Arabidopsis thaliana] GI:3256066; contains InterPro entry IPR001236: Lactate/malate dehydrogenase; contains Pfam profiles PF00056: lactate/malate dehydrogenase, NAD |
| Organic N | At3g47520 | binding domain and PF02866: lactate/malate dehydrogenase, alpha/beta C-terminal domain (68416.m05168) |
| Organic N | At3g48740 | nodulin MtN3 family protein similar to MtN3 GI:1619602 (root nodule development) from [Medicago truncatula] (68416.m05322) |
| | | AMP-dependent synthetase and ligase family protein similar to peroxisomal-coenzyme A synthetase (FAT2) [gi:586339] from Saccharomyces cerevisiae; contains Pfam AMP-binding enzyme domain PF00501; identical to cDNA; identical to cDNA adenosine monophosphate binding |
| Organic N | At3g48990 | protein 3 AMPBP3 (AMPBP3)GI:20799714 (68416.m05351) |
| Organic N | At3g49940 | LOB domain protein 38/lateral organ boundaries domain protein 38 (LBD38) identical to SP |
| Organic N | At3g58990 | aconitase C-terminal domain-containing protein contains Pfam profile PF00694: Aconitase C-terminal domain (68416.m06575) |
| | | transketolase, putative strong similarity to transketolase 1 [Capsicum annuum] GI:3559814; contains Pfam profiles PF02779: Transketolase, pyridine binding domain, PF02780: Transketolase, C-terminal domain, PF00456: Transketolase, thiamine diphosphate binding domain |
| Organic N | At3g60750 | (68416.m06796) |
| | | BON1-associated protein 1 (BAP1) identical to BON1-associated protein 1 [Arabidopsis thaliana] GI:15487384; contains Pfam profile PF00168: |
| Organic N | At3g61190 | C2 domain; supporting cDNA gi |
| | | homeobox-leucine zipper protein 12 (HB-12)/HD-ZIP transcription factor 12 identical to homeobox-leucine zipper protein ATHB-12 |
| Organic N | At3g61890 | (GI:6899887) [Arabidopsis thaliana] (68416.m06951) |
| Organic N | At4g12280 | copper amine oxidase family protein contains Pfam domain, PF01179: Copper amine oxidase, enzyme domain (68417.m01946) |
| Organic N | At4g13510 | ammonium transporter 1, member 1 (AMT1.1) identical to SP |
| Organic N | At4g13770 | cytochrome P450 family protein (68417.m02136) |
| | | glucose-6-phosphate isomerase, putative similar to glucose-6-phosphate isomerase [Spinacia oleracea] GI:3413511; contains Pfam profile |
| Organic N | At4g24620 | PF00342: glucose-6-phosphate isomerase (68417.m03526) |
| | | cinnamoyl-CoA reductase-related similar to cinnamoyl-CoA reductase from Pinus taeda [GI:17978649], Saccharum officinarum [GI:3341511] |
| Organic N | At4g30470 | (68417.m04326) |
| | | mannitol transporter, putative similar to mannitol transporter [Apium graveolens var. dulce] GI:12004316; contains Pfam profile PF00083: |
| Organic N | At4g36670 | major facilitator superfamily protein (68417.m05203) |
| Organic N | At4g37540 | LOB domain protein 39/lateral organ boundaries domain protein 39 (LBD39) identical to SP |
| | | TAZ zinc finger family protein/BTB/POZ domain-containing protein contains Pfam PF00651: BTB/POZ domain; contains Pfam PF02135: |
| Organic N | At4g37610 | TAZ zinc finger; similar to Speckle-type POZ protein (SP:O43791) [Homo sapiens] (68417.m05321) |
| | | protein kinase family protein similar to protein kinase [gi:170047] from Glycine max; contains Pfam protein kinase domain PF00069 |
| Organic N | At4g38470 | (68417.m05436) |
| Organic N | At4g39800 | inositol-3-phosphate synthase isozyme 1/myo-inositol-1-phosphate synthase 1/MI-1-P synthase 1/IPS 1 identical to SP |
| | | nicotianamine synthase, putative similar to nicotianamine synthase [Lycopersicon esculentum][GI:4753801], nicotianamine synthase 2 |
| Organic N | At5g04950 | [Hordeum vulgare][GI:4894912] (68418.m00524) |
| | | urophorphyrin III methylase (UPM1) identical to urophorphyrin III methylase (GI:1146165) [Arabidopsis thaliana]; similar to s-adenosyl-L-methionine-dependent uroporphyrinogen III methyltransferase (GI:1490606) [Arabidopsis thaliana]; similar to Diphthine synthase (Diphtamide biosynthesis methyltransferase) (DPH5) (SP:P32469) [Saccharomyces cerevisiae]; contains Pfam PF00590: Tetrapyrrole (Corrin/Porphyrin) |
| Organic N | At5g40850 | Methylases domain; contains TIGRFAM PF00590: Tetrapyrrole (Corrin/Porphyrin) Methylases (68418.m04960) |
| | | 6-phosphogluconate dehydrogenase family protein contains Pfam profiles: PF00393 6-phosphogluconate dehydrogenase C-terminal domain, |

TABLE 4-continued

| Regulated by | PUB LOCUS | Gene Name |
|---|---|---|
| Organic N | At5g41670 | PF03446 NAD binding domain of 6-phosphogluconate (68418.m05063) |
| Organic N | At5g45340 | cytochrome P450 family protein similar to SP |
| Organic N | At5g46050 | proton-dependent oligopeptide transport (POT) family protein contains Pfam profile: PF00854 POT family (68418.m05663) |
| Organic N | At5g48370 | thioesterase family protein similar to SP sodium-inducible calcium-binding protein (ACP1)/sodium-responsive calcium-binding protein (ACP1) identical to NaCl-inducible Ca2+-binding |
| Organic N | At5g49480 | protein GI:2352828 from [Arabidopsis thaliana] (68418.m06123) |
| Organic N | At5g51830 | pfkB-type carbohydrate kinase family protein contains Pfam profile: PF00294 pfkB family carbohydrate kinase (68418.m06426) |
| Organic N | At5g54170 | expressed protein weak similarity to SP protein kinase family protein/non phototropic hypocotyl 1-like protein (NPL1) contains Pfam domains, PF00069: Protein kinase domain and PF00785: PAC motif; similar to SP:O48963 Nonphototropic hypocotyl protein 1 (Phototropin) [Mouse-ear cress] {Arabidopsis thaliana}; |
| Organic N | At5g58140 | identical to cDNA non phototropic hypocotyl 1-like (NPL1) GI:5391441 (68418.m07277) |

This table contains a list of genes that were previously identified as regulated by inorganic N (Wang et al., 2004 Plant Physiol 136:2512-2522) and that were found regulated in the current study. The first column summarizes the regulatory pattern observed in this study.

Nitrogen signals control amino acid metabolism in *Arabidopsis* seedlings. To evaluate the biological significance of the observed patterns of response to the treatments, the distribution of functional categories in the six classes defined in Table 3 were analyzed using the BioMaps program (Gutierrez et al., 2007, Genome Biol. 8:R7). To focus on the most prominent biological processes affected, over-represented functional terms (p≤0.01) with 5 or more genes (Table 5) were analyzed. This analysis indicated that inorganic N represses amino acid biosynthesis, and in particular a subset of genes related to the metabolism of S-containing amino acids. In addition, increased levels of internal Glu appears to induce the expression of genes involved in cell wall biosynthesis, especially genes in the xyloglucan:xyloglucosyl transferase family. Internal Glu also appears to repress genes involved in several aspects of metabolism, most prominently amino acid and carbohydrate metabolism. This analysis also showed that genes involved in secondary metabolism are repressed by both internal and external organic N sources. These results indicate that the balance between organic and inorganic N controls the expression of genes involved in N-reduction, N-assimilation and amino acid metabolism in *Arabidopsis* plants and coordinates N-assimilation with cellular processes including for example, cell wall biosynthesis.

TABLE 5

| Response | MIPS Functional Term | p-value | Genes |
|---|---|---|---|
| Inorganic nitrogen repression (100) | amino acid biosynthesis (12) | 0.00322 | At3g54640, At4g13890, At3g01120, At5g37600, At3g23810, At2g36880, At4g39980, At4g15560, At5g23020, At3g17390, At5g16570, At3g03780 |
| Internal Glu induction (89) | cell wall (7) | 0.00933 | At5g64570, At1g03870, At1g32170, At2g01850, At1g11545, At3g23730, At3g14310 |
| Internal Glu repression (246) | METABOLISM (98) | 6.95E−05 | At3g61190, At5g65620, At5g64440, At5g37990, At3g02360, At1g08920, At5g49720, At1g75680, At2g44160, At2g30490, At5g35170, At1g77760, At4g00370, At1g51680, At1g15130, At3g19420, At4g33580, At1g17840, At3g60750, At2g30870, At3g54690, At1g15950, At2g47180, At5g01820, At5g20070, At4g24620, At2g46830, At5g05730, At4g21850, At1g06640, At5g20980, At5g48370, At4g36640, At4g34050, At2g38010, At4g19810, At3g48690, At2g27860, At5g03555, At1g22610, At2g36690, At3g63010, At3g21240, At4g29900, At2g39210, At1g37130, At4g33680, At1g79380, At4g39800, At4g36250, At5g63850, At1g02400, At1g53500, At1g66900, At5g01800, At4g14440, At1g11840, At3g44720, At2g20360, At2g22240, At5g54960, At4g12280, At5g55910, At1g03590, At2g38700, At5g54160, At1g65960, At2g16430, At5g11110, At2g30040, At4g11570, At3g21230, At5g58140, At4g39640, At5g37510, At4g00360, At3g01560, At4g30440, At2g40890, At2g47880, At3g48560, At5g49630, At1g76670, At5g43370, At4g30470, At4g25300, At2g29450, At2g40140, At4g39330, At1g07890, At4g30280, At1g12000, At2g36290, At5g53370, At1g74710, At3g45640, At3g23820, At3g17820 |
| | amino acid metabolism (28) | 0.00017 | At3g61190, At5g64440, At5g63850, At4g39640, At5g05730, At4g21850, At1g06640, At5g20980, At1g02400, At2g44160, At3g48560, At5g49630, At2g30490, At1g11840, At1g77760, At3g44720, At1g22610, At4g25300, At5g54960, At3g60750, At2g36690, At1g07890, At3g54690, At1g37130, At1g65960, At1g74710, At4g33680, At3g17820 |
| | complex cofactor binding (13) | 0.00235 | At4g36250, At3g60750, At5g37510, At4g36640, At1g15950, At2g44160, At3g48560, At1g53500, At2g30490, At2g27860, At4g33680, At5g54960, At4g12280 |

TABLE 5-continued

| Response | MIPS Functional Term | p-value | Genes |
|---|---|---|---|
| | C-compound and carbohydrate utilization (36) | 0.00673 | At4g36250, At3g02360, At5g49720, At1g75680, At2g44160, At1g53500, At1g11840, At2g20360, At2g22240, At5g54960, At4g33580, At3g60750, At3g54690, At1g15950, At5g11110, At2g47180, At4g11570, At4g24620, At3g21230, At5g37510, At5g20980, At4g30440, At3g48560, At3g48690, At2g27860, At1g76670, At4g30470, At4g39330, At4g30280, At3g21240, At3g63010, At2g36290, At1g12000, At5g53370, At3g23820, At4g39800 |
| Internal/External Glu repression (102) | secondary metabolism (19) | 0.0036 | At3g16150, At1g13110, At4g15390, At3g58990, At1g06000, At4g39950, At4g22710, At4g30210, At1g20510, At2g05710, At5g48010, At5g26030, At1g02500, At5g40850, At1g10360, At1g05010, At2g34460, At5g47990, At5g45340 |

Network analysis reveals a metabolic gene network connected to regulatory transcription factors regulated by organic N. To uncover the mechanism underlying gene regulation in response to sensing Glu or a Glu-derived product, network analysis was used to identify the subnetwork of genes regulated by organic N (FIG. 3). The subnetwork of N-regulated genes using an *Arabidopsis* multinetwork was generated as described previously (Gutierrez et al., 2007, Genome Biol 8:R7). Cytoscape was used to visualize the resulting subnetworks wherein genes were represented as nodes connected by edges that represented distinct interactions (e.g., metabolic reactions, regulatory interactions). In addition to the interactions described previously (Gutierrez et al., 2007, Genome Biol 8:R7), regulatory connections were predicted between genes and associated transcription factors (see, Materials and Methods). In order to identify putative "master regulators" that control the expression of genes regulated by organic N, the transcription factors regulated in these experiments were ranked based on the number of regulatory connections in the subnetwork (Table 6). At the top of the list, were a Myb family transcription factor (At1g74840), the central clock gene CCA1 (At2g46830) and a golden 2-related transcription factor (GLK1; At2g20570). Interestingly, both CCA1 and GLK1 were predicted to positively affect the expression of a gene for glutamine synthetase (GLN1.3) (which uses Glu in a biosynthetic reaction), and to negatively affect the expression of a glutamate dehydrogenase gene (GDH1) (which catabolizes Glu) (FIG. 3). Moreover, the analysis suggests that both CCA1 and GLK1 block the expression of a bZIP transcription factor (bZIP1) which is predicted to induce the expression of the Gln-dependent ASN1 gene. Thus, Glu regulation of the GLK1 and CCA1 transcription factors appears to coordinate the expression of genes involved in making Gln (GLN1.3) vs. those involved in metabolizing Gln into Glu (ASN1, GDH1). In addition, another gene in this gene subnetwork encodes a putative asparaginase gene (ANS) that controls the degradation of Asn (to Asp and Glu) (FIG. 3). The ASN1 (Asn biosynthesis) and ANS (Asn degradation) genes had inverse expression patterns (correlation=-0.51), suggesting that Glu coordinates the reciprocal regulation of Asn synthesis and degradation by coordinating an antiregulation of the cognate.

TABLE 6

| Number of connections | PUB LOCUS | Annotation |
|---|---|---|
| 51 | At1g74840 | myb family transcription factor. |
| 47 | At2g46830 | myb-related transcription factor (CCA1) |
| 46 | At2g20570 | golden2-like transcription factor (GLK1) |
| 31 | At4g37260 | myb family transcription factor (MYB73) |

TABLE 6-continued

| Number of connections | PUB LOCUS | Annotation |
|---|---|---|
| 30 | At5g24800 | bZIP1 transcription factor family protein contains |
| 30 | At5g49450 | bZIP1 family transcription factor |
| 29 | At5g14540 | proline-rich family protein contains proline rich extensin domains. |
| 29 | At5g48655 | zinc finger (C3HC4-type RING finger) family protein |
| 24 | At1g22070 | bZIP1 family transcription factor (TGA3) |
| 23 | At3g01560 | proline-rich family protein contains proline rich extensin domains. |
| 20 | At2g22430 | homeobox-leucine zipper protein 6 (HB-6) |
| 19 | At5g44190 | myb family transcription factor (GLK2) |
| 16 | At1g43160 | AP2 domain-containing protein RAP2.6 (RAP2.6) |
| 15 | At3g61890 | homeobox-leucine zipper protein 12 (HB-12) |
| 14 | At5g61890 | AP2 domain-containing transcription factor family protein similar to RAP2.6 |
| 12 | At3g61150 | homeobox-leucine zipper family protein |
| 11 | At2g38470 | WRKY family transcription factor |
| 11 | At4g17500 | ethylene-responsive element-binding protein 1 (ERF1) |
| 10 | At2g25000 | WRKY family transcription factor |

Validation of network model predictions highlights the regulatory role of CCA1 in the N-assimilatory pathway. The model in FIG. 3 predicts that CCA1 and/or GLK1 genes are important regulators of genes involved in N-assimilation and over-expression of either one of these genes would repress the expression of ASN1 and GDH1 and induce the expression of the GLN1.3 gene. Conversely, a knockout of the CCA1 or GLK1 gene should increase ASN1 and GDH1 expression levels and diminish GLN1.3 mRNA levels. To test these hypotheses, we used previously characterized CCA1 overexpressor (CCA1-ox) (Wang et al., 1998, Cell 93:1207-1217) and GLK1 gene knockout (glk1) (Fitter et al., 2002, Plant J 31:713-727) lines. A stronger phenotype for the overexpressor lines was anticipated as compared to the knockout, as the model predicts redundancy in the function of CCA1 and GLK1 in regulating ASN1, GDH1 and GLN1.3 gene expression. CCA1-ox, glk1 and wild-type plants were grown for two weeks as above, and samples were collected in the morning (3 h after dawn). Total RNA was extracted from whole seedlings and RT-qPCR was performed to determine mRNA levels for ASN1, GLN1.3 and GDH1 in the three genotypes. As shown in FIG. 4, all three genes tested showed altered expression patterns in the mutant lines utilized (as determined by analysis of variance, $p \leq 0.05$) which were consistent with the predicted network model shown in FIG. 1. In addition, bZIP1 mRNA level was also repressed in CCA1-ox (FIG. 10). ASN1, GDH1 and GLN1.3 mRNA levels were not altered in the glk1 line, with the exception of a small increase in GDH1 mRNA levels. This is probably due to the redundant function of GLK1 and CCA1 in regulating the expression of the tested genes. In contrast, and as predicted by the model shown in FIG. 3, ASN1 and GDH1 levels were decreased in the CCA1-ox line. Also consistent with the predictions of the model, GLN1.3 mRNA levels were increased as compared to wild-type in the CCA1-ox.

The network model predicts that the effect of CCA1 on the expression of the target genes will be direct. To test this hypothesis, ChIP assays were used using a CCA1 antibody (FIG. 4B). As controls, it was demonstrated that the ChIP assays could detect binding of CCA1 protein to a region of the TOC1 promoter, a known target of CCA1, but was not able to detect the ZTL promoter which has no circadian oscillation at the mRNA level. Consistent with the model for CCA1, ChIP assays in both wild-type and CCA1-ox lines were able to confirm binding of CCA1 to the promoter regions of GLN1.3, GDH1 and bZIP1 promoters. These results support the model, and indicate that CCA1 regulates expression of bZIP1, GDH1 and GLN1.3 genes directly, and indirectly for ASN1 through bZIP1.

N-nutrient signals act as input to the *Arabidopsis* circadian clock. CCA1 is a key component of a negative feedback loop at the center of the *Arabidopsis* circadian clock (Mc-Clung, 2006, Plant Cell 18:792-803; Millar, 2004, J. Exp. Bot. 55:277-283). Because the results showed that N-treatments affected CCA1 expression, it was hypothesized that N might serve as an input capable of affecting the circadian clock function. To test this hypothesis, pulses of inorganic or organic N were provided at intervals spanning a circadian cycle and determined the effects on the phase of the oscillation in CCA1::LUC expression. Each treatment resulted in stable phase shifts indicating that N status serves as an input to the circadian clock (FIG. 5 and FIG. 11). Inorganic N and 10 mM Glu treatments conferred slight phase advances whereas 10 mM Gln conferred only delays. The Nms and Glu pulses did not affect the period but the Gln pulse shortened the period as determined by one-way analysis of variance and Dunn's multiple comparison tests. Thus, the clock regulates a number of steps in N metabolism, such as NR expression and activity (Pilgrim et al., 1993, Plant Mol Biol 23:349-64) and ASN1 expression as demonstrated herein (see also Harmer et al., 2000, Science 290:2110-2113). In turn, N status feeds back to the clock, at least in part through its effect on CCA1 expression.

7.4 Discussion

In the present study, genomic and pharmacological approaches were used to distinguish organic from inorganic N responses in *Arabidopsis* seedlings. The majority of the genes regulated by the N-treatments used in this study (81%) are responding to organic N signals. Among the genes regulated by organic N, we distinguished two classes of genes: (i) genes that responded only to external Glu application and (ii) genes that responded to internal and external sources of Glu (Table 3). The difference in these two expression patterns raises the possibility that there are different mechanisms for sensing internally produced cellular Glu vs. extra cellular Glu that is transported between cells. The other possibility is that the differences in internal vs. external Glu responses observed in this study reflect distinct threshold responses to Glu levels. There is precedence for internal and external Glu sensing mechanisms in other organisms. Bacteria regulate ammonium assimilation via a mechanism involving PII, a sensor that measures levels of α-ketoglutarate and Glu (Arcondeguy et al., 2001, Microbiol Mol Biol Rev 65:80-105). Plants contain a PII protein that is localized to chloroplasts (Hsieh et al., 1998, Proc Natl Acad Sci USA 95:13965-13970), a potential sensor of internal levels of Glu. By contrast, extracellular Glu is sensed by Glu receptors in animal brains (Sykova, 2004, Neuroscience 129:861-876). The presence of Glu receptor genes in plants (Lacombe et al., 2001, Science 292:1486-1487) raises the possibility that Glu receptors in plants may serve to sense levels of external apoplastic transported Glu.

Analysis of the genes regulated by N, identified a gene network with transcription factors that appear to regulate the expression of N-assimilatory genes. New to this study is the finding that the NR genes (NIA1, NIA2) are repressed by organic N, as is GLN1.3, which is involved in Gln biosynthesis. Within this N-regulated network we also found genes involved in N uptake and metabolism including an ammonium transporter (AMT1.1), genes involved in assimilating N into and out of Asn (ASN1, ANS), as well as amino acid transporter genes. Organic N negatively regulated AMT1.1 and ANS, but induced the ASN1 gene. It was therefore hypothesized that in the presence of Glu, or a Glu-derived metabolite, Asn production is optimized and regulated at the level of transcription by increasing levels of ASN1 and decreasing levels of ANS transcripts. These results are consistent with Asn serving as a major N storage compound (Lam et al., 1994, Plant Physiol 106:1347-1357) controlled by the ASN1 gene, and suggest a mechanism to maximize Asn production, degradation and distribution depending on levels of internal sources of organic N.

The network analysis proposed a mechanism for transcriptional regulation of N-assimilation. ASN1 was a predicted target of the transcription factor bZIP1; GDH1, GLN1.3 and bZIP1 were predicted targets of GLK1 and CCA1. Because bZIP1 is also regulated by carbon (Gutierrez et al., 2007, Genome Biol 8:R7), this gene may be an integrator of C and N signaling for regulation of N-assimilation in *Arabidopsis*. This our network model was validated by measuring mRNA levels of the target genes in CCA1-ox and glk1 knockout lines. As predicted, ASN1 and GDH1 mRNA levels were down regulated and GLN1.3 mRNA was elevated in the CCA1-ox line. In contrast, mRNA levels for these three genes were not affected in the glk1 knockout line. The lack of a molecular phenotype in the glk1 knockout may be explained by the fact that CCA1 and GLK1 are predicted to have the same regulatory function in the subnetwork. The predictions that CCA1 directly targets a number of genes in the network was validated using CCA1 antibodies in ChIP experiments. Because CCA1 is one of the central components of the circadian clock in *Arabidopsis*, regulation of CCA1 expression in response to organic N suggests that the circadian clock may receive N nutritional inputs in plants. Thus, in addition to light and temperature (Millar, 2004, J. Exp. Bot. 55:277-283; McClung, 2001, Ann. Rev. Plant Physiol Plant Mol. Biol. 52:139-162), nutrients—such as N—may act as input for the clock. The phase response curve analysis results presented herein are consistent with weak (type 1) resetting similar to those observed in response to light pulses in *Lemna gibba* (Kondo, 1983, Plant Cell Physiol. 24:659-665), KCl or ethanol pulses in *Phaseolus coccineus* (Bunning and Moser, 1973, Proc Natl Acad Sci USA 70:3387-3389) and cAMP or imidazole pulses in *Trifolium repens* (Bollig et al., 1978, Planta 141:225-230), strengthening the hypothesis that N status feeds back to the clock, at least in part through its effect on CCA1 expression. In *Arabidopsis*, light pulses evoke strong delays (~8 h) in the early night and strong advances (5-10 h) later in the night (Covington et al., 2001, Plant Cell 13:1305-1315). Although the molecular basis of these phase shifts is not definitively established, they may involve induction of CCA1 by light (Wang et al., 1998, Cell 93:1207-1217). In the above-experiments, N treatment would decrease CCA1 mRNA abundance. That this elicits only small phase shifts suggests that posttranscriptional regulation buffers against CCA1 activity changes from reduced mRNA, at least over the time frames tested with our 4-h N pulses. Alternatively, N treatment may also modulate other clock components either at the mRNA, protein abundance or protein activity level in ways that reduce the magnitude of the phase shifts in response to CCA1 mRNA decrease. The emerging view of the circadian clock is as a key integrator of multiple metabolic and physiologic processes (Lam et al., 1994, Plant Physiol 106:1347-1357; Kondo, 1983, Plant Cell Physiol. 24:659-665). As such it receives input not only from environmental stimuli but also from multiple metabolic pathways, many of which are subject to circadian regulation. Thus, the clock regulates a number of steps in N metabolism, such as NR expression and activity (Bunning and Moser, 1973, Proc Natl Acad Sci USA 70:3387-3389) and ASN1 expression. In turn, N status feeds back to the clock, at least in part through its effect on CCA1 expression. This feedback is more subtle than the effects of saturating light pulses and our results are consistent with N status fine tuning clock function rather than conferring large changes such as those observed in response to light (FIG. 6).

Oscillations in the mRNA of genes that code for metabolic enzymes could have an impact on metabolite levels, as recently shown (Gibon et al., 2006, Genome Biology 7:R76). Predicting time of food availability is key for the survival in most animals (Stephan, 2002, J Biol Rhythms 17:284-292). The data presented herein suggest that this may also be the case in *Arabidopsis*, e.g., anticipating the availability of carbon skeletons produced by photosynthesis to assimilate inorganic N into amino acids. Moreover, this data provides a plausible molecular mechanism for how this could happen in plants via CCA1. The present study thus provides evidence that plant nutrition, like in animals, is tightly linked to circadian functions as previously hypothesized (Harmer et al., 2000, Science 290:2110-2113). Recently, it was shown that the central clock gene Per2 is necessary for food anticipation in mice (Feillet et al., 2006, Curr Biology 16:2016-2022). The present data indicates that the central clock gene CCA1 plays a role in circadian regulation of N-assimilation in plants (FIG. 12). This data is consistent with a model in which the N-assimilatory pathway is a downstream target of the clock with CCA1 being the direct regulatory factor. Moreover, Glu or other Glu-derived signal act as input to the circadian clock providing a link between plant N-nutrition and circadian rhythms.

8. EQUIVALENTS

Although the invention is described in detail with reference to specific embodiments thereof, it will be understood that variations which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims. Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference in their entireties.

What is claimed is:

1. A transgenic plant that exhibits increased nitrogen-assimilation capacity as compared to a wild-type plant, the transgenic plant having a first gene construct comprising a polynucleotide encoding *Arabidopsis* Basic Leucine Zipper 1 (bZIP1) operatively linked to a first promoter with activity in plants, and a second gene construct comprising a polynucleotide encoding *Arabidopsis* Golden 2-like 1 (GLK1) operatively linked to a second promoter with activity in plants, wherein the first and second promoters are optionally (a) a constitutive, tissue-specific, or inducible promoter or (b) associated with a constitutive or inducible regulatory element, and wherein the first and second promoters can be the same or different.

2. The transgenic plant of claim 1, wherein the plant is a species of woody, ornamental, decorative, crop, cereal, fruit, or vegetable.

3. The transgenic plant of claim 1, wherein the plant is a species of one of the following genuses: *Acorus, Aegilops, Allium, Amborella, Antirrhinum, Apium, Arachis, Beta, Betula, Brassica, Capsicum, Ceratopteris, Citrus, Cryptomeria, Cycas, Descurainia, Eschscholzia, Eucalyptus, Glycine, Gossypium, Hedyotis, Helianthus, Hordeum, Ipomoea, Lactuca, Linum, Liriodendron, Lotus, Lupinus, Lycopersicon, Medicago, Mesembryanthemum, Nicotiana, Nuphar, Pennisetum, Persea, Phaseolus, Physcomitrella, Picea, Pinus, Poncirus, Populus, Prunus, Robinia, Rosa, Saccharum, Schedonorus, Secale, Sesamum, Solanum, Sorghum, Stevia, Thellungiella, Theobroma, Triphysaria, Triticum, Vitis, Zea,* or *Zinnia*.

4. A method of producing a plant-derived commercial product using the transgenic plant according to claim 1.

5. The method of producing a plant-derived commercial product of claim 4, wherein said transgenic plant is a tree, and said commercial product is pulp, paper, a paper product, or lumber.

6. The method of producing a plant-derived commercial product of claim 4, wherein said transgenic plant is tobacco, and said commercial product is a cigarette, cigar, or chewing tobacco.

7. The method of producing a plant-derived commercial product of claim 4, wherein said transgenic plant is a crop, and said commercial product is a fruit or vegetable.

8. The method of producing a plant-derived commercial product of claim 4, wherein said transgenic plant is a grain, and said commercial product is bread, flour, cereal, oat meal, or rice.

9. The transgenic plant of claim 1, wherein the plant is a species of the genus *Arabidopsis*.

10. The transgenic plant of claim 1, wherein the first and second promoters are constitutive promoters.

11. The transgenic plant of claim 1, wherein the first and second promoters are inducible promoters.

12. The transgenic plant of claim 1, wherein the first promoter is a seed-specific promoter.

13. The transgenic plant of claim 1, wherein the second promoter is a leaf-specific promoter.

14. The transgenic plant of claim 12, wherein the second promoter is a leaf-specific promoter.

15. The transgenic plant of claim 3, wherein the first and second promoters are inducible promoters.

16. The transgenic plant of claim 3, wherein the first promoter is a seed-specific promoter.

17. The transgenic plant of claim 3, wherein the second promoter is a leaf-specific promoter.

18. The transgenic plant of claim 17, wherein the second promoter is a leaf-specific promoter.

19. A method of producing a plant-derived commercial product using the transgenic plant according to claim 3.

20. The method of producing a plant-derived commercial product of claim 19, wherein said transgenic plant is a crop, and said commercial product is a fruit or vegetable.

* * * * *